US010776453B2

(12) United States Patent
Fallon et al.

(10) Patent No.: US 10,776,453 B2
(45) Date of Patent: Sep. 15, 2020

(54) SYSTEMS AND METHODS EMPLOYING REMOTE DATA GATHERING AND MONITORING FOR DIAGNOSING, STAGING, AND TREATMENT OF PARKINSONS DISEASE, MOVEMENT AND NEUROLOGICAL DISORDERS, AND CHRONIC PAIN

(75) Inventors: Joan M. Fallon, White Plains, NY (US); James J. Fallon, Armonk, NY (US); Matthew Heil, Sherman, CT (US); Stephen J. Weiss, New Rochelle, NY (US)

(73) Assignee: GALENAGEN, LLC, Rye Brook, NY (US)

( * ) Notice: Subject to any disclaimer, the term of this patent is extended or adjusted under 35 U.S.C. 154(b) by 0 days.

(21) Appl. No.: 12/535,676

(22) Filed: Aug. 4, 2009

(65) Prior Publication Data
US 2010/0169409 A1 Jul. 1, 2010

Related U.S. Application Data

(60) Provisional application No. 61/086,136, filed on Aug. 4, 2008.

(51) Int. Cl.
*G06F 15/16* (2006.01)
*G06F 17/30* (2006.01)
(Continued)

(52) U.S. Cl.
CPC ......... *G06F 19/3418* (2013.01); *G16H 50/20* (2018.01); *Y02A 90/26* (2018.01)

(58) Field of Classification Search
CPC ............... H04L 29/08072; H04L 29/06; H04L 29/0809; G06F 19/3418; Y02A 90/26; G16H 50/20
See application file for complete search history.

(56) References Cited

U.S. PATENT DOCUMENTS 3,002,883 A 10/1961 Butt et al.
3,223,594 A 12/1965 Serge
(Continued)

FOREIGN PATENT DOCUMENTS

CA 2198317 A1 2/1997
CA 2263703 A1 8/1999
(Continued)

OTHER PUBLICATIONS

We Move, PD Workbook, The WEMOVE Clinician's Guide to Parkinson's Disease, 2006.*
(Continued)

*Primary Examiner* — Abdullahi E Salad
(74) *Attorney, Agent, or Firm* — Wilson Sonsini Goodrich & Rosati

(57) ABSTRACT

This disclosure relates to early diagnosis and assessment tools for Parkinson's disease, movement disorder, neurological disease, and/or chronic pain, designed to drive innovation and to accelerate best Parkinson's disease, movement disorders, neurological disease, and chronic pain research. The present disclosure facilitates improved access to Parkinson's disease, movement disorders, neurological disease, and chronic pain patients along with innovative data capture methods that are designed to leading to improved therapies and assisting in finding a cure for Parkinson's disease, movement disorders, neurological diseases, and/or chronic pain. In addition the present disclosure is broadly applicable as a diagnosis and assessment tool to all movement disorders and many neurological diseases and/or chronic pain.

90 Claims, 30 Drawing Sheets

(51) Int. Cl.
*G06F 19/00* (2018.01)
*G16H 50/20* (2018.01)

(56) References Cited

U.S. PATENT DOCUMENTS

| | | | |
|---|---|---|---|
| 3,322,626 A | 5/1967 | D'Argento | |
| 3,357,894 A | 12/1967 | Jose et al. | |
| 3,515,642 A | 6/1970 | Mima et al. | |
| 3,574,819 A | 4/1971 | Gross et al. | |
| 3,860,708 A | 1/1975 | Prout | |
| 3,940,478 A | 2/1976 | Kurtz | |
| 4,079,125 A | 3/1978 | Sipos | |
| 4,145,410 A | 3/1979 | Sears | |
| 4,241,046 A | 12/1980 | Papahadjopoulos et al. | |
| 4,280,971 A | 7/1981 | Wischniewski et al. | |
| 4,447,412 A | 5/1984 | Bilton | |
| 4,456,544 A | 6/1984 | Lupova et al. | |
| 4,500,515 A | 2/1985 | Libby | |
| 4,623,624 A | 11/1986 | Schultze | |
| 4,826,679 A | 5/1989 | Roy | |
| 5,023,108 A | 6/1991 | Bagaria et al. | |
| 5,190,775 A | 3/1993 | Klose | |
| 5,227,166 A | 7/1993 | Ueda et al. | |
| 5,250,418 A | 10/1993 | Moller et al. | |
| 5,324,514 A | 6/1994 | Sipos | |
| 5,378,462 A | 1/1995 | Boedecker et al. | |
| 5,436,319 A | 7/1995 | Kung et al. | |
| 5,437,319 A | 8/1995 | Garuglieri | |
| 5,439,935 A | 8/1995 | Rawlings et al. | |
| 5,460,812 A | 10/1995 | Sipos | |
| 5,476,661 A | 12/1995 | Pillai et al. | |
| 5,527,678 A | 7/1996 | Blaser et al. | |
| 5,585,115 A | 12/1996 | Sherwood et al. | |
| 5,607,863 A | 3/1997 | Chandler | |
| 5,648,335 A | 7/1997 | Lewis et al. | |
| 5,674,532 A | 10/1997 | Atzl et al. | |
| 5,686,311 A | 11/1997 | Shaw | |
| 5,750,104 A | 5/1998 | Sipos | |
| 5,753,223 A | 5/1998 | Shibahara et al. | |
| 5,776,917 A | 7/1998 | Blank et al. | |
| 5,858,758 A | 1/1999 | Hillman et al. | |
| 5,952,178 A | 9/1999 | Lapidus et al. | |
| 5,958,875 A | 9/1999 | Longo et al. | |
| 5,977,175 A | 11/1999 | Lin | |
| 5,985,891 A | 11/1999 | Rowe | |
| 6,011,001 A | 1/2000 | Navia et al. | |
| 6,013,286 A | 1/2000 | Klose | |
| 6,020,310 A | 2/2000 | Beck et al. | |
| 6,020,314 A | 2/2000 | McMichael | |
| 6,096,338 A | 8/2000 | Lacy et al. | |
| 6,100,080 A | 8/2000 | Johansen | |
| 6,149,585 A * | 11/2000 | Gray | 600/300 |
| 6,153,236 A | 11/2000 | Wu et al. | |
| 6,168,569 B1 * | 1/2001 | McEwen et al. | 600/557 |
| 6,187,309 B1 | 2/2001 | McMichael et al. | |
| 6,197,746 B1 | 3/2001 | Beck et al. | |
| 6,210,950 B1 | 4/2001 | Johnson et al. | |
| 6,238,727 B1 | 5/2001 | Takemoto et al. | |
| 6,251,478 B1 | 6/2001 | Pacifico et al. | |
| 6,261,602 B1 | 7/2001 | Calanchi et al. | |
| 6,261,613 B1 | 7/2001 | Narayanaswamy et al. | |
| 6,280,726 B1 | 8/2001 | Weinrauch et al. | |
| 6,287,585 B1 | 9/2001 | Johansen | |
| 6,309,669 B1 | 10/2001 | Setterstrom et al. | |
| 6,399,101 B1 | 6/2002 | Frontanes et al. | |
| 6,482,839 B1 | 11/2002 | Thornfeldt | |
| 6,498,143 B1 | 12/2002 | Beck et al. | |
| 6,534,063 B1 | 3/2003 | Fallon | |
| 6,534,259 B1 | 3/2003 | Wakefield | |
| 6,632,429 B1 | 3/2003 | Fallon | |
| 6,558,708 B1 | 5/2003 | Lin | |
| 6,562,629 B1 | 5/2003 | Lin et al. | |
| 6,569,463 B2 | 5/2003 | Patel et al. | |
| 6,660,831 B2 | 12/2003 | Fallon | |
| 6,699,885 B2 | 3/2004 | Phillips | |
| 6,727,073 B1 | 4/2004 | Moore et al. | |
| 6,743,447 B2 | 6/2004 | Labergerie et al. | |
| 6,764,447 B2 * | 7/2004 | Iliff | 600/300 |
| 6,783,757 B2 | 8/2004 | Brudnak | |
| 6,790,825 B2 | 9/2004 | Beck et al. | |
| 6,797,291 B2 | 9/2004 | Richardson | |
| 6,808,708 B2 | 10/2004 | Houston | |
| 6,821,514 B2 | 11/2004 | Houston | |
| 6,827,688 B2 * | 12/2004 | Goto et al. | 600/485 |
| 6,835,397 B2 | 12/2004 | Lee et al. | |
| 6,852,487 B1 | 2/2005 | Barany et al. | |
| 6,861,053 B1 | 3/2005 | Lin et al. | |
| 6,890,561 B1 | 5/2005 | Blatt et al. | |
| 6,899,876 B2 | 5/2005 | Houston | |
| 6,923,988 B2 | 8/2005 | Patel et al. | |
| 6,980,958 B1 * | 12/2005 | Surwit et al. | 705/2 |
| 7,048,906 B2 | 5/2006 | Lin et al. | |
| 7,081,239 B2 | 7/2006 | Lin | |
| 7,091,182 B2 | 8/2006 | Beck et al. | |
| 7,101,573 B2 | 9/2006 | Szymczak et al. | |
| 7,122,357 B2 | 10/2006 | Sander et al. | |
| 7,129,053 B1 | 10/2006 | Reiter et al. | |
| 7,138,123 B2 | 11/2006 | Fallon | |
| 7,232,670 B2 | 6/2007 | D'Azzo et al. | |
| 7,244,412 B2 | 7/2007 | Lin | |
| 7,285,633 B2 | 10/2007 | Wu et al. | |
| 7,381,698 B2 | 6/2008 | Fein et al. | |
| 7,395,216 B2 * | 7/2008 | Rosenfeld et al. | 705/2 |
| 7,479,378 B2 | 1/2009 | Potthoff et al. | |
| 7,483,747 B2 * | 1/2009 | Gliner et al. | 607/45 |
| 7,588,757 B2 * | 9/2009 | Ozawa et al. | 424/93.2 |
| 7,608,245 B2 | 10/2009 | Lin | |
| 7,630,913 B2 * | 12/2009 | Kay | 705/4 |
| 7,658,918 B1 | 2/2010 | Ortenzi et al. | |
| 7,718,169 B2 | 5/2010 | Margolin et al. | |
| 7,736,622 B2 | 6/2010 | Lin et al. | |
| 7,935,799 B2 | 5/2011 | Lin et al. | |
| 7,945,451 B2 * | 5/2011 | Cosentino et al. | 705/2 |
| 8,008,036 B2 | 8/2011 | Fallon | |
| 8,012,710 B2 | 9/2011 | Fallon | |
| 8,012,930 B2 | 9/2011 | Fallon | |
| 8,030,002 B2 | 10/2011 | Fallon | |
| 8,055,516 B2 * | 11/2011 | Iliff | 705/3 |
| 8,066,636 B2 * | 11/2011 | Iliff | 600/300 |
| 8,084,025 B2 | 12/2011 | Fallon | |
| 8,105,584 B2 | 1/2012 | Fallon | |
| 8,163,278 B2 | 4/2012 | Fallon | |
| 8,187,209 B1 * | 5/2012 | Giuffrida | A61B 5/0488 600/595 |
| 8,211,661 B2 | 7/2012 | Fallon | |
| 8,221,747 B2 | 7/2012 | Ortenzi et al. | |
| 8,318,158 B2 | 11/2012 | Fallon | |
| 8,437,689 B2 * | 5/2013 | Mazar | 455/1 |
| 8,486,390 B2 | 7/2013 | Fallon | |
| 8,580,522 B2 | 11/2013 | Fallon | |
| 8,613,918 B2 | 12/2013 | Fallon | |
| 8,658,163 B2 | 2/2014 | Fallon | |
| 8,673,877 B2 | 3/2014 | Fallon et al. | |
| 8,778,335 B2 | 7/2014 | Fallon | |
| 8,815,233 B2 | 8/2014 | Fallon | |
| 8,921,054 B2 | 12/2014 | Fallon | |
| 8,980,252 B2 | 3/2015 | Fallon | |
| 9,017,665 B2 | 4/2015 | Fallon | |
| 9,023,344 B2 | 5/2015 | Fallon | |
| 9,056,050 B2 | 6/2015 | Fallon et al. | |
| 9,061,033 B2 | 6/2015 | Fallon | |
| 9,084,784 B2 | 7/2015 | Fallon et al. | |
| 9,107,419 B2 | 8/2015 | Fallon et al. | |
| 9,233,146 B2 | 1/2016 | Fallon | |
| 9,320,780 B2 | 4/2016 | Fallon | |
| 9,345,721 B2 | 5/2016 | Fallon et al. | |
| 9,408,895 B2 | 8/2016 | Fallon | |
| 10,098,844 B2 | 10/2018 | Fallon et al. | |
| 2001/0006644 A1 | 7/2001 | Bova et al. | |
| 2001/0023360 A1 * | 9/2001 | Nelson et al. | 607/60 |
| 2001/0024660 A1 | 9/2001 | Ullah et al. | |
| 2002/0001575 A1 | 1/2002 | Foreman | |
| 2002/0037284 A1 | 3/2002 | Fallon | |
| 2002/0061302 A1 | 5/2002 | Sander-Struckmeier et al. | |

(56) References Cited

U.S. PATENT DOCUMENTS

| | | |
|---|---|---|
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1* | 8/2002 | Vanelli ............................ 705/3 |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1 | 2/2005 | Bodor |
| 2005/0036950 A1 | 2/2005 | Jones et al. |
| 2005/0079594 A1 | 4/2005 | Marion |
| 2005/0137134 A1* | 6/2005 | Gill et al. ................... 514/12 |
| 2005/0170479 A1 | 8/2005 | Weaver et al. |
| 2005/0187130 A1 | 8/2005 | Booker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1* | 11/2006 | Coifman ............... A61B 5/0871 600/538 |
| 2006/0258599 A1 | 11/2006 | Childers |
| 2006/0259995 A1 | 11/2006 | Cayouette et al. |
| 2006/0294108 A1* | 12/2006 | Adelson ............... G06F 19/3456 |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1* | 8/2007 | Kover et al. ................... 600/558 |
| 2007/0250119 A1* | 10/2007 | Tyler .................. A61N 1/36014 607/2 |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1* | 7/2008 | Zakim ................. G06F 19/325 705/3 |
| 2008/0187525 A1 | 8/2008 | Porubcon |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1* | 12/2008 | Slotman ............................ 435/4 |
| 2008/0317731 A1 | 12/2008 | Gramatikova et al. |
| 2009/0004285 A1 | 1/2009 | Yu et al. |
| 2009/0018407 A1* | 1/2009 | Jung ...................... A61B 3/113 600/301 |
| 2009/0063402 A1* | 3/2009 | Hayter ............... A61B 5/14532 |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0171696 A1* | 7/2009 | Allard ................... G06Q 50/24 705/3 |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1* | 2/2011 | Hoffberg et al. ............. 715/811 |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0027848 A1 | 2/2012 | Fallon et al. |
| 2012/0070504 A1 | 3/2012 | Fallon |
| 2012/0114562 A1 | 5/2012 | Fallon |
| 2012/0114626 A1 | 5/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2012/0258149 A1 | 10/2012 | Fallon et al. |
| 2013/0059001 A1 | 3/2013 | Fallon |
| 2013/0095152 A1 | 4/2013 | Fallon |
| 2013/0113129 A1 | 5/2013 | Fallon et al. |
| 2013/0195833 A1 | 8/2013 | Fallon |
| 2013/0202581 A1 | 8/2013 | Fallon et al. |
| 2013/0224172 A1 | 8/2013 | Fallon et al. |
| 2013/0323223 A1 | 12/2013 | Fallon et al. |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0140550 A1 | 5/2015 | Fallon |
| 2015/0147308 A1 | 5/2015 | Fallon et al. |
| 2015/0150955 A1 | 6/2015 | Fallon et al. |
| 2015/0151198 A1* | 6/2015 | Dugan ................. A61B 5/0002 463/29 |
| 2015/0174219 A1 | 6/2015 | Fallon |
| 2015/0174220 A1 | 6/2015 | Fallon |
| 2015/0182607 A1 | 7/2015 | Jolly et al. |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon et al. |
| 2016/0213697 A1 | 7/2016 | Fallon et al. |
| 2018/0243282 A1 | 8/2018 | Fallon |
| 2018/0360759 A1 | 12/2018 | Fallon |
| 2019/0175704 A1 | 6/2019 | Fallon |
| 2019/0183990 A1 | 6/2019 | Fallon et al. |
| 2019/0201507 A1 | 7/2019 | Fallon |
| 2019/0209667 A1 | 7/2019 | Fallon |

(56) References Cited

U.S. PATENT DOCUMENTS

| | | |
|---|---|---|
| 2019/0275066 A1 | 9/2019 | Fallon et al. |
| 2019/0275128 A1 | 9/2019 | Fallon et al. |

FOREIGN PATENT DOCUMENTS

| | | |
|---|---|---|
| CA | 2667976 A1 | 5/2008 |
| CA | 2719102 A1 | 9/2009 |
| CN | 1031562 A | 3/1989 |
| CN | 1329923 A | 1/2002 |
| CN | 1552836 A | 12/2004 |
| CN | 1791430 A | 6/2006 |
| CN | 101039667 A | 9/2007 |
| CN | 101208092 A | 6/2008 |
| DE | 3738599 A1 | 5/1989 |
| DE | 4332985 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 6/2008 |
| EP | 2258837 A1 | 12/2010 |
| EP | 2318035 A1 | 5/2011 |
| EP | 2373791 A1 | 10/2011 |
| GB | 669782 A | 4/1952 |
| GB | 2347742 A | 9/2000 |
| GB | 2480772 A | 11/2011 |
| GB | 2506537 A | 4/2014 |
| JP | H 04-364119 A | 12/1992 |
| JP | 62230714 A | 9/2000 |
| JP | 2003517831 A | 6/2003 |
| JP | 2004500591 A | 1/2004 |
| JP | 2005515223 A | 5/2005 |
| JP | 2006512091 A | 4/2006 |
| JP | 2007523664 A | 8/2007 |
| JP | 2008512468 A | 4/2008 |
| JP | 2008283895 A | 11/2008 |
| JP | 2013517251 A | 5/2013 |
| KR | 20050084485 A | 8/2005 |
| RU | 2356244 C1 | 5/2009 |
| TW | 310277 B | 7/1997 |
| WO | WO 84/02846 A1 | 8/1984 |
| WO | WO-8908694 A1 | 9/1989 |
| WO | WO 90/02562 A1 | 3/1990 |
| WO | WO 94/19005 A1 | 9/1994 |
| WO | WO 95/22344 A1 | 8/1995 |
| WO | WO 97/32480 A1 | 9/1997 |
| WO | WO 98/22499 A2 | 5/1998 |
| WO | WO-9826807 A1 | 6/1998 |
| WO | WO 98/22499 A3 | 7/1998 |
| WO | WO-9832336 A2 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 00/21504 A1 | 4/2000 |
| WO | WO 01/27612 A2 | 4/2001 |
| WO | WO 01/45835 A1 | 6/2001 |
| WO | WO 2001/043764 A2 | 6/2001 |
| WO | WO 01/27612 A3 | 10/2001 |
| WO | WO 2001/043764 A3 | 11/2001 |
| WO | WO 2002/014537 A2 | 2/2002 |
| WO | WO-0219828 A1 | 3/2002 |
| WO | WO 2002/014537 A3 | 5/2002 |
| WO | WO 02/051352 A2 | 7/2002 |
| WO | WO 02/051436 A2 | 7/2002 |
| WO | WO 03/051345 A2 | 6/2003 |
| WO | WO 03/059088 A1 | 7/2003 |
| WO | WO 2004/060074 A1 | 7/2004 |
| WO | WO 2007/074454 A2 | 7/2004 |
| WO | WO-2004093883 A2 | 11/2004 |
| WO | WO-2005092370 A1 | 10/2005 |
| WO | WO 2005/115445 A1 | 12/2005 |
| WO | WO 2006/031554 A2 | 3/2006 |
| WO | WO 2006/044529 A1 | 4/2006 |
| WO | WO-2006060414 A2 | 6/2006 |
| WO | WO 2006/031554 A3 | 9/2006 |
| WO | WO 2007/002572 A2 | 1/2007 |
| WO | WO 2007/147714 A1 | 12/2007 |
| WO | WO-2008013747 A2 | 1/2008 |
| WO | WO 2008/021987 A2 | 2/2008 |
| WO | WO 2008/102264 A2 | 8/2008 |
| WO | WO 2009/114757 A2 | 9/2009 |
| WO | WO 2009/155689 A1 | 12/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2010/120781 A1 | 10/2010 |
| WO | WO 2011/000924 A1 | 1/2011 |
| WO | WO-2011050135 A1 | 4/2011 |
| WO | WO 2011/114225 A1 | 9/2011 |
| WO | WO-2012067621 A1 | 5/2012 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |

OTHER PUBLICATIONS

German et al., Apple iPhone Review: Apple iPhone, Jun. 30, 2007; C|NET.*

U.S. Appl. No. 13/144,286, filed Jul. 12, 2011, Fallon et al.

U.S. Appl. No. 13/144,290, filed Jul. 12, 2011, Fallon et al.

U.S. Appl. No. 13/204,881, filed Aug. 8, 2011, Fallon et al.

U.S. Appl. No. 13/208,963, filed Aug. 12, 2011, Fallon.

Amendment dated Mar. 24, 2010 in Reply to Final Office Action dated Sep. 24, 2009 for U.S. Appl. No. 12/046,252.

Axcan Pharma Inc. Cdn Prescribing Information on VIOKASE Pancrelipase, USP tablets, powder. 2000: 1-3.

Cichoke, et al. The complete book of enzyme therapy. Penguin. 1998: 39, 42, 47, 50, and 53.

Derwent. Abstract for RU 2286785 Nov. 10, 2006. Downloaded from the Derwent file Jul. 13, 2011.

Heijerman, et al. Omeprazole enhances the efficacy of pancreatin (pancrease) in cystic fibrosis. Ann Intern Med. Feb. 1, 1991;114(3):200-1.

Kachrimanis, et al. Tensile strength and disintegration of tableted silicified microcrystalline cellulose: influences of interparticle bonding. J Pharm Sci. Jul. 2003;92(7):1489-501.

Levy, et al. Relationship of dietary intake to gastrointestinal symptoms in children with autistic spectrum disorders. Biol Psychiatry. Feb. 15, 2007;61(4):492-7.

Liyanage, et al. Bioavailability of iron from micro-encapsulated iron sprinkle supplement. Food and Nutrition bulletin. 2002; 23(3):133-137.

Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.

Notice of Allowance dated Apr. 15, 2011 for U.S. Appl. No. 12/487,868.

Notice of Allowance dated Apr. 29, 2011 for U.S. Appl. No. 12/046,402.

Notice of Allowance dated May 23, 2011 for U.S. Appl. No. 09/990,909.

Notice of Allowance dated Jun. 27, 2011 for U.S. Appl. No. 12/238,415.

Notice of Allowance dated Jun. 28, 2011 for U.S. Appl. No. 12/487,868.

Notice of Allowance dated Jun. 30, 2011 for U.S. Appl. No. 09/990,909.

Notice of Allowance dated Jul. 8, 2011 for U.S. Appl. No. 12/046,402.

(56) References Cited

OTHER PUBLICATIONS

Notice of Allowance dated Aug. 8, 2011 for U.S. Appl. No. 12/426,794.
Notice of Allowance dated Sep. 20, 2011 for U.S. Appl. No. 12/283,090.
Office Action dated Mar. 29, 2011 for U.S. Appl. No. 12/054,343.
Office Action dated Mar. 30, 2011 for U.S. Appl. No. 12/786,739.
Office Action dated Apr. 27, 2011 for U.S. Appl. No. 10/681,018.
Office Action dated Apr. 28, 2011 for U.S. Appl. No. 12/283,090.
Office Action dated May 24, 2011 for U.S. Appl. No. 12/487,864.
Office action dated Jun. 29, 2011 for U.S. Appl. No. 11/555,697.
Office action dated Oct. 19, 2011 for U.S. Appl. No. 12/386,051.
Smith, et al. Fecal chymotrypsin and trypsin determinations. Canadian Medical Association Journal. 1971; 104(8):691-4 and 697.
Sturmey. Secretin is an ineffective treatment for pervasive developmental disabilities: a review of 15 double-blind randomized controlled trials. Res Dev Disabil. Jan.-Feb. 2005;26(1):87-97.
U.S. Appl. No. 13/193,346, filed Jul. 28, 2011, Fallon.
U.S. Appl. No. 13/271,783, filed Oct. 12, 2011, Fallon.
Final Offce Action dated Jan. 3, 2012 for U.S. Appl. No. 10/681,018.
Office action dated Jan. 12, 2012 for U.S. Appl. No. 12/047,818.
Office action dated Dec. 15, 2011 for U.S. Appl. No. 12/493,147.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Tran, et al. Treatment of complex regional pain syndrome: a review of the evidence. Can J Anaesth. Feb. 2010;57(2):149-66.
Final Offce Action dated Jan. 26, 2012 for U.S. Appl. No. 12/487,864.
Isaksson, et al. Pain reduction by an oral pancreatic enzyme preparation in chronic pancreatitis. Digestive Dis. Sci. 1983; 28(2):97-102.
Lashkari, et al. Williams-Beuren syndrome: An update and review for the primary physician. Clinical Pediatrics. 1999; 38(4):189-208.
Meyer-Lindenberg, et al. Neural mechanisms in Williams syndrome: a unique window to genetic influences on cognition and behaviour. Nat. Rev. Neurosci. 200617(5):380-93.
Offce Action dated Feb. 1, 2012 for U.S. Appl. No. 12/493,122.
U.S. Appl. No. 13/002,136, filed Dec. 30, 2010, Fallon.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 22, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Jul. 2, 2010 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aal-a376-6e519a5a0f80.
Barlow. A comparison of the blood pressure, kidney volume and the pancreatic secretory response following the vein administration of various secretin preparations. Am J Phys. 1927;81:182-188.
Belmonte et al. Fragile X syndrome and autism at the intersection of genetic and neural networks. Nat Neurosci. Oct. 2006; 9(10):1221-5 (abstract only).
Blackmer. Parkinson disease: treatment and medication. Mar. 10, 2009., retrieved from the internet on Sep. 15, 2009, http://emedicine.medscape.com/article/312519-treatment.
Bode et al. Usefulness of a simple photometric determination of chymotrypsin activity in stools—results of a multicentre study. Clin Biochem. 1986; 19:333-37.
Brudnak et al. Enzyme-based therapy for autism spectrum disorders—is it worth another look? Med Hypoth. 2002; 58:422-428.
Campbell et al. A genetic variant that disrupts MET transcription is associated with autism. Proc Natl Acad Sci USA. 2006; 103(45):16834-16839.
Carlton. Autism and malnutrition: the milk connection. Retrieved from the internet on Feb. 18, 2008, http://www.mercola.com/2004/autism_malnutrition.htm.
Cruse et al. Illustrated dictionary of immunology. CRC Press, New York. 1995.
Darman. An introduction to alternative medicine for psychiatric conditions. Oct. 22, 2007, retrieved on Sep. 18, 2009, http://web.archive.org/web/20071022104238/http://altp[therapies4bipolar.info/ortho/html.
Digestive Enzyme, retrieved from the internet Sep. 10, 2009, http://en.wikipedia.org/wiki/Digestive_enzyme.

(56) References Cited

OTHER PUBLICATIONS

Dobbs et al. Link between helicobacter pylori infection and idiopathic parkinsonism. Medical Hypothsis. 200; 55(2):93-98.
Dockter et al. Determination of chymotrypsin in the feces by a new photometric method. Padiatr Padol. 1985; 20(3):257-265.
Filipek et al. The screening and diagnosis of autistic spectrum disorders. J. of Autism and Dev Disorders. 1999; 29(6).
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Happe et al. The neuropsychology of autism. Brain. 1996; 119:1377-1400.
Happe et al. Time to give up on a simple explanation for autism. Nat Neurosci. Oct. 2006; 9(10):1218-20.
Hendren et al. Mechanistic biomarkers for autism treatment. Medical Hypotheses. 2009; 73:950-954.
Horvath et al. Improved social and language skills after secretin administration in patients with autistic spectrum disorders. Journal of the Association for Academic Minority Physicians. Jan. 1998; 9(1):9-15.
Hoshiko et al. The effect of the gastrointestinal hormones on colonic muscosal blood flow. Acta Medica Nagasakiensia. 1994; 39(4):125-130.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Kaspar et al. New photometric assay for chymotrypsin in stool. Clinical Chemistry. 1984; 30(11):1753-1757.
Koster et al. Evidence based medicine and extradigestive manifestations of helocobacter pylori. Acta Gastro-Enterologica Belgica. 200; 63(4):388-392.
Layer et al. Pancreatin enzyme replacement therapy. Current Gastroenterology Reports. 2001; 3:101-108.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
MacReady. Parkinson's Diseasne Treatment: what you should know. Retrieved from the internet on Sep. 15, 2009, http://www.everydayhealth.com/parkinsons-disease-treatment-overview.aspx.

Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (Not in English).
Marsh. Neuropsychiatric aspects of parkinson's disease. Psychosomatics. 2000; 41(1):15-23.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
Medsafe. Data sheet for alpha-lactose, Jul. 21, 1999, http://www.medsafe.govt.nz/Profs/Datasheet/a/Alphalactulosesyrup.htm.
Merck. Autism, Merck manual online medical library home addition, retrieved from the internet Mar. 10, 2008, http://www.mercl.com/mmhge/sec23/ch286/ch286b.html.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Michell et al. Biomarkers and parkinson's disease. Brain. 2004; 127(8):1693-1705.
Munasinghe et al. Digestive enzyme supplementation for autism spectrum disorders: a double-blind randomized controlled trial. J Autism Dev Disord. Mar. 5, 1010; Epub ahead of print.
Nachaegari et al. Coprocessed excipients for solid dosage forms. Pharmaceutical Technology. 2004; p. 52, 54, 56 ,58, 60, 64.
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
NINDS Dysautonimia Information Page, retrieved from the internet Sep. 10, 2009, http://www.ninds.nih.gov/disorders/dysautonomia/dysautonomia.htm.
NINDS Guillain-Barre Syndrome Information Page, retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.

(56) References Cited

OTHER PUBLICATIONS

Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.
Perman et al. Role of ph in production of hydrogen from carbohydrates by colonic bacterial flora. J Clin Invest. 1981; 24(4):684-685.
Peters et al. Prevalence of enteric parasites in homosexual patients attending an outpatient clinic. J of Clin Micro. 1986; 24(4):684-685.
Preliminary Amendment dated May 18, 2009 for U.S. Appl. No. 12/046,252.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Rogers, No more heartburn: Stop the pain in 30 days—naturally. 2000; 172.
Sandler et al. Short term benefit from oral vancomycin treatment of regressive-onset autism. J of Child Neuro. 2000; 15(7):42-435.
Schiller. Review article: the therapy of constipation. Aliment Pharmacol Ther. 2001; 15:749-763.
Schreck et al. Food preferences and factors influecing food selectivity for children with autism spectrum disorders. Res Develop Disabil. 2006; 27:353-363.
Seneca et al. Enhancement of brain 1-dopa concetration with a-chymotrypsm. J American Geriatrics Society. 1973; 256-258.
Sherwood et al. A new class of high-functionality excipients: silicified microcrystalline cellulose. Pharm Tech. 1998; 22(10):78-88.
Skeels et al. Crytosporidium infection in Oregon public health clinic patients 1985-88: the value of statewide laboratory surveillance. AJPH. 1990; 80(3):305-308.
Stein, et a. Nitrogen Metabolism in normal and hyperkinetic boys. Am J Clin Nutr. 1984; 39:520-524.
Supplemental Amendment and Response dated Jun. 8, 2010 to Restriction Requirement dated Oct. 7, 2009 for U.S. Appl. No. 12/283,090.
The Alzheimer's Association. Basics of Alzheimer's Disease. 2005, http://www.alz.org/national/documents/brochure_Basicsofalz_low/pdf.
Tsang et al. Extragastroduodenal conditions associated with Heliobacter pylori infection. Hong Kong Medical Journal. 1999; 5(2):169-174.
USP (32)—NF(27) 2009, Pancreatin, V.3, pp. 3194-3195.
Wender et al. Prevalence of attention deficit disorder, residual type, and other psychiatric disorders in patients with irritable colon syndrome. Am J Psychiatry. 1983; 140(12):1579-82 Abstract only.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Zhang et al. Lactulose-mannitol intestinal permeability test in children with diarrhea caused by rotavirus abd cryptosporidium. J of Pediatric Gastro & Nutrition. 2000; 31(1):16-21.
Final Office Action dated Nov. 8, 2011 for U.S. Appl. No. 12/054,343.
Final Office Action dated Nov. 8, 2011 for U.S. Appl. No. 12/786,739.
Thefreedictionary. Term Sprinkles. Www.thefreedictionary.com. Accessed Nov. 2, 2011. 1 page.
U.S. Appl. No. 13/836,135, filed Mar. 15, 2013, Fallon et al.
Chen, et al. Medicinal Functions of Bromelain and Its Application Prospect in Animal Husbandry, China Animal Husbandry & Veterinary Medicine, vol. 32, No. 1, p. 14-16. (in Chinese with English translation).
Millipore EMD catalog (online). Papain, unit definition, EMD Millipore Corp, 2013. Downloaded May 13, 2013.
Office action dated May 9, 2013 for U.S. Appl. No. 13/204,881.
Office action dated May 15, 2013 for U.S. Appl. No. 13/502,989.
Roxas, et al. Colds and influenza: a review of diagnosis and conventional, botanical, and nutritional considerations. Alternative Medicine Review. 2007; 12(1):25-48.
UK search and examination report dated Mar. 26, 2013 for GB 1111565.6.
UK search and examination report dated Mar. 27, 2013 for GB 1111566.4.
UK search and examination report dated Apr. 18, 2013 for GB 1117669.0.
U.S. Appl. No. 13/733,873, filed Jan. 3, 2012, Fallon et al.
U.S. Appl. No. 13/737,225, filed Jan. 9, 2012, Fallon.
Bray, et al. Effect of dietary protein content on weight gain, energy expenditure, and body composition during overeating. A randomized controlled trial. JAMA. Jan. 4, 2012; 307(1):47-55.
Ferrone, et al. Pancreatic enzyme pharmacotherapy. Pharmacotherapy. 2007; 27:910-920.
Information of Papain from Worthington Enzymes webpage http://www.worthington-biochem.com/pap/default.html Downloaded Jan. 17, 2013.
International search report and written opinion dated Feb. 21, 2013 for PCT/US2013/020183.

(56) References Cited

OTHER PUBLICATIONS

International search report and written opinion dated Nov. 12, 2012 for PCT/US2012/034489.
Office action dated Jan. 22, 2013 for U.S. Appl. No. 13/562,999.
Office action dated Jan. 25, 2013 for U.S. Appl. No. 13/208,963.
Office action dated Feb. 14, 2013 for U.S. Appl. No. 13/193,346.
Office action dated Feb. 14, 2013 for U.S. Appl. No. 13/407,408.
Office action dated Feb. 21, 2013 for U.S. Appl. No. 12/047,818.
Olivar-Parra, et al. Training referential communicative skills to individuals with autism spectrum disorder: a pilot study. Psychological Reports. 2011; 109:921-939.
Patel, et al. Formulation and evaluation of mucoadhesive glipizide microspheres. AAPS PharmSciTech. 2005; 6(1):E49-E55.
Serna, et al. Pathogenesis and treatment of Shiga toxin-producing *Escherichia coli* infections. Curr Opin Gastroenterol. Jan. 2008;24(1):38-47.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
U.S. Appl. No. 13/705,763, filed Dec. 5, 2012, Fallon et al.
Bowers. Endocrine secretions of the pancreas. Jul. 5, 2006. Accessed online at www.vivo.colostate.edu/hbooks/pathphys/digestion/pancreas/exocrine.html.
Office action dated Sep. 13, 2012 for U.S. Appl. No. 13/481,087.
Office action dated Oct. 10, 2012 for U.S. Appl. No. 13/201,881.
Office action dated Oct. 25, 2012 for U.S. Appl. No. 13/144,286.
Office action dated Oct. 25, 2012 for U.S. Appl. No. 13/144,290.
Office action dated Dec. 6, 2012 for U.S. Appl. No. 13/002,136.
Walsh, et al. Reduced violent behavior following chemical therapy. Physiology and behavior. 2004; 82:835-839.
U.S. Appl. No. 13/757,412, filed Feb. 1, 2013, Fallon et al.
Mitsui, et al. Role of aminopepridases in the blood pressure regulation. Biological and Pharmaceutical Bulletin of Japan, Pharmaceutical Sociey of Japan. 2004; 27(6):768-771.
Office action dated Mar. 5, 2013 for U.S. Appl. No. 12/493,122.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3):261-267.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
U.S. Appl. No. 13/313,629, filed Dec. 7, 2011, Fallon.
U.S. Appl. No. 13/313,708, filed Dec. 7, 2011, Fallon.
U.S. Appl. No. 13/407,408, filed Feb. 28, 2012, Fallon et al.
U.S. Appl. No. 13/481,087, filed May 25, 2012, Fallon.
U.S. Appl. No. 13/502,989, filed Apr. 19, 2012, Heil et al.
U.S. Appl. No. 13/503,844, filed Apr. 24, 2012, Fallon et al.
U.S. Appl. No. 13/562,999, filed Jul. 31, 2012, Fallon.
Dajcs, et al. Lysostaphin is effective in treating methicillin-resistant *Staphylococcus aureus* endophthalmitis in the rabbit. Curr Eye Res. Jun. 2001;22(6):451-7.
Dupiereux, et al. Creutzfeldt-jakob, Parkinson, lewy body dementia and Alzheimer diseases: from diagnosis to therapy. Cent Nerv Syst Agents Med Chem. Mar. 2009;9(1):2-11.
Elkashef, et al. Biological markers of cocaine addiction: implications for medications development. Addict Biol. Jun. 2003;8(2):123-39.
Fallon. Could one of the most widely prescribed antibiotics amoxicillin/clavulanate "augmentin" be a risk factor for autism? Med Hypotheses. 2005;64(2):312-5.
Horvath, et al. Autism and gastrointestinal symptoms. Curr Gastroenterol Rep. Jun. 2002;4(3):251-8.
Jenkins, et al. Management of gastroenteritis. Archives of Disease in Childhood. 1990; 65:939-941.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.

Martin, et al. A rapid and sensitive spectrophotometric method for the assay of chymotrypsin. Biol Chem. Feb. 1959;234(2):294-8.
Notice of Allowance dated Feb. 17, 2012 for U.S. Appl. No. 10/681,018.
Notice of Allowance dated Mar. 21, 2012 for U.S. Appl. No. 12/487,864.
Notice of allowance dated Jul. 3, 2012 for U.S. Appl. No. 13/271,783.
Office Action dated Mar. 19, 2012 for U.S. Appl. No. 13/204,881.
Office Action dated Mar. 23, 2012 for U.S. Appl. No. 13/271,783.
Office Action dated Apr. 5, 2012 for U.S. Appl. No. 11/555,697.
Office Action dated Apr. 9, 2012 for U.S. Appl. No. 13/208,963.
Office action dated Jun. 13, 2012 for U.S. Appl. No. 12/493,122.
Office action dated Jun. 27, 2012 for U.S. Appl. No. 12/493,147.
Office action dated Jul. 11, 2012 for U.S. Appl. No. 12/573,353.
Office action dated Jul. 18, 2012 for U.S. Appl. No. 12/047,818.
Office action dated Aug. 13, 2012 for U.S. Appl. No. 13/208,963.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Schumann. Medical, nutritional and technological properties of lactulose. An update. Eur J Nutr. Nov. 2002;41 Suppl 1:I17-25.
Sillanaukee, et al. Improved diagnostic classification of alcohol abusers by combining carbohydrate-deficient transferrin and gamma-glutamyltransferase. Clin Chem. Apr. 2001;47(4):681-5.
Wisniewski, et al. Therapeutic approaches for prion and Alzheimer's diseases. FEBS J. Aug. 2007;274(15):3784-98. Epub Jul. 6, 2007.
U.S. Appl. No. 14/087,930, filed Nov. 22, 2013, Fallon et al.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Childhood Autism Rating Scale (CARS), Wikipedia, downloaded May 5, 2014.
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Curemark press release. Curemark Receives Investigational New Drug Clearance for CM-AT for Autism. Mar. 26, 2009. http://www.medicalnewstoday.com/releases/143723.php.
Digestive Enzyme Preparation: Pancreatin listed in Japanese Pharmacopoeia, Aug. 2008, <URL:http://database.japic.or.jp/pdf/newPINS/00009938.pdf> (in Japanese with English translation).
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Lebenthal, et al. Enzyme therapy for pancreatic insufficiency: present status and future needs. Pancreas. Jan. 1994;9(1):1-12.
MacDonald. Thyrotoxicosis treated with pancreatic extract and iodine. Lancet. 1943; 244(6251):788.
Notice of allowance dated Jan. 2, 2014 for U.S. Appl. No. 13/204,881.
Office action dated Jan. 15, 2014 for U.S. Appl. No. 13/836,135.
Office action dated Jan. 16, 2014 for U.S. Appl. No. 12/046,252.
Office action dated Jan. 24, 2014 for U.S. Appl. No. 12/054,343.
Office action dated Jan. 24, 2014 for U.S. Appl. No. 12/786,739.
Office action dated Mar. 11, 2014 for U.S. Appl. No. 11/533,818.
Office action dated Apr. 10, 2014 for U.S. Appl. No. 13/502,989.
Office action dated Apr. 16, 2014 for U.S. Appl. No. 13/705,763.
Office action dated May 12, 2014 for U.S. Appl. No. 13/733,873.
Office action dated May 13, 2014 for U.S. Appl. No. 13/313,629.
Office action dated May 15, 2014 for U.S. Appl. No. 13/448,061.
Office action dated May 16, 2014 for U.S. Appl. No. 13/313,708.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Okahata, et al. Lipid-coated enzymes as efficient catalysts in organic media. Trends in Biotechnology. 1997; 15(2):50-54.

(56) References Cited

OTHER PUBLICATIONS

Pancreatin 8X USP Powder. Product Specification. Jul. 2000. In: Product Manual. American Laboratories Incorporated. Omaha, NE. p. 1.
Williams, et al. Intravenous secretin for autism spectrum disorders (ASD). Cochrane Database Syst Rev. Apr. 18, 2012;4:CD003495. doi: 10.1002/14651858.CD003495.pub3.
U.S. Appl. No. 13/926,822, filed Jun. 25, 2013, Fallon.
U.S. Appl. No. 14/007,793, filed Sep. 26, 2013, Fallon.
U.S. Appl. No. 14/037,652, filed Sep. 26, 2013, Fallon.
U.S. Appl. No. 14/037,696, filed Sep. 26, 2013, Fallon.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Carroccio, et al. Pancreatic enzyme therapy in childhood celiac disease. A double-blind prospective randomized study. Dig Dis Sci. Dec. 1995;40(12):2555-60.
Creon. Full prescribing information. Last edited Mar. 2013. Abbvie Inc 2012. www.rxabbvie.com/pdf/creon_PI.pdf.
Eaves, et al. The criterion-related validity of the Childhood Autism Rating Scale and the Autism Behavior Checklist. J Abnorm Child Psychol. Oct. 1993;21(5):481-91. abstract only.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
International search report and written opinion dated Aug. 27, 2013 for PCT/US2013/043444.
King, et al. Effects of bacterial microflora of the lower digestive tract of free-range waterfowl on influenza virus activation. Appl Environ Microbiol. Jun. 2011;77(12):4119-25. doi: 10.1128/AEM. 02578-10. Epub Apr. 29, 2011.
Leeds, et al. Is exocrine pancreatic insufficiency in adult coeliac disease a cause of persisting symptoms? Aliment Pharmacol Ther. Feb. 1, 2007;25(3):265-71.
Notice of Allowance dated May 29, 2013 for U.S. Appl. No. 13/481,087.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Oct. 29, 2013 for U.S. Appl. No. 13/204,881.
Office action dated Jun. 25, 2013 for U.S. Appl. No. 13/144,286.
Office action dated Jun. 25, 2013 for U.S. Appl. No. 13/144,290.
Office action dated Jul. 15, 2013 for U.S. Appl. No. 13/002,136.
Office action dated Jul. 31, 2013 for U.S. Appl. No. 13/757,412.
Office action dated Aug. 14, 2013 for U.S. Appl. No. 13/448,061.
Office action dated Aug. 28, 2013 for U.S. Appl. No. 13/313,629.
Office action dated Sep. 9, 2013 for U.S. Appl. No. 13/502,989.
Office action dated Oct. 24, 2013 for U.S. Appl. No. 13/313,708.
Office action dated Nov. 29, 2013 for U.S. Appl. No. 13/193,346.
Pancrease. Patient information leaflet. Pancrease HL Capsules. Last updated Apr. 30, 2013. Janssen-cilag LTD. www.medicines.org.uk/EMC/medicine/7326.
Petrolatum: Pharmaceutical Excipients. London: Pharmaceutical Press. 2006. 1-6.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Xu. Pancreatin therapy in chronic pancreatitis. Clin J Dig, May 2005; 25(5):313-315. (in Chinese with English translation).
U.S. Appl. No. 14/296,091, filed Jun. 4, 2014, Fallon.
U.S. Appl. No. 14/493,734, filed Sep. 23, 2014, Fallon.
U.S. Appl. No. 14/528,715, filed Oct. 30, 2014, Fallon.
Cichoke. Celiac disease. The complete book of enzyme therapy. Penguin. New York, NY. 1999; 174-177.
Curepark Trademark/Service mark application, Principal Register. Serial No. 77527223. Filing date: Jul. 21, 2008.
eMedExpert, Antibiotics:Cephalosporins, Available online at: www.emedexpert.com/compare/ cephalosporins.shtml, available as early as Jun. 2, 2007 per Internet Archive Wayback Machine.
GM Chemie 2010 "Products: Hypromellose Phthalate" accessed from www.gmchemie.com on Sep. 22, 2014.
International preliminary report on patentability dated Jul. 17, 2014 for PCT/US2013/020183.
Merriam-Webster 2014 "Definition: Precipitate" accessed from www.mirriam-webster.com on Sep. 22, 2014.
Munasinghe et al. Digestive enzyme supplementation for autism spectrum disorders: a double-blind randomized controlled trial. J Autism Dev Disord. Sep. 2010;40(9):1131-8.
Notice of allowance dated Jun. 12, 2014 for U.S. Appl. No. 13/448,061.
Notice of allowance dated Aug. 11, 2014 for U.S. Appl. No. 13/193,346.
Notice of allowance dated Sep. 15, 2014 for U.S. Appl. No. 14/037,652.
Notice of allowance dated Dec. 23, 2014 for U.S. Appl. No. 14/007,793.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 27, 2014 for U.S. Appl. No. 14/007,793.
Office action dated Aug. 7, 2014 for U.S. Appl. No. 13/836,135.
Office action dated Aug. 29, 2014 for U.S. Appl. No. 13/144,286.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office action dated Nov. 7, 2014 for U.S. Appl. No. 12/786,739.
Office action dated Nov. 21, 2014 for U.S. Appl. No. 13/926,822.
Office action dated Dec. 18, 2014 for U.S. Appl. No. 14/037,696.
Office action dated Dec. 19, 2014 for U.S. Appl. No. 13/733,873.
Sundstrom, et al. A deadly prion disease: fatal familial insomnia. J Neurosci Nurs. Dec. 2003;35(6):300-5. Abstract only.
U.S. Appl. No. 14/612,580, filed Feb. 3, 2015, Fallon et al.
U.S. Appl. No. 14/612,604, filed Feb. 3, 2015, Fallon et al.
Fliri, et al. Drug effects viewed from a signal transduction network perspective. J Med Chem. Dec. 24, 2009;52(24):8038-46. doi: 10.1021/jm901001p.
Notice of allowance dated Feb. 2, 2015 for U.S. Appl. No. 13/926,822.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Office action dated Mar. 6, 2015 for U.S. Appl. No. 13/757,412.
Office action dated Apr. 6, 2015 for U.S. Appl. No. 14/493,734.
U.S. Appl. No. 14/921,896, filed Oct. 23, 2015, Fallon et al.
Block, et al. A rapid food screener to assess fat and fruit and vegetable intake. Am J Prev Med. May 2000;18(4):284-8.
Brinkley, et al. Factor analysis of the aberrant behavior checklist in individuals with autism spectrum disorders. J Autism Dev Disord. Nov. 2007;37(10):1949-59. Epub Dec. 21, 2006.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
Creon digestive enzymes. Celic.com/ Jun. 2009. http://www.celiac.com/gluten-free/topic/59195-creon-digestive-enzymes.
Emc, Creon 10000 Capsules, May 18, 2015, Available Online at: www.medicines.org.uk/emc/medicine/2068.
Holten, et al. Appropriate prescribing of oral beta-lactam antibiotics. Am Fam Physician. Aug. 1, 2000;62(3):611-20.

(56) References Cited

OTHER PUBLICATIONS

International search report and written opinion dated May 9, 2013 for PCT/US2013/024453.
NIH, "Celiac Disease", National Digestive Diseases Information Clearinghouse: Bethesda, MD, 2008; 12 pages.
Notice of allowance dated Sep. 9, 2015 for U.S. Appl. No. 13/193,346.
Notice of allowance dated Nov. 16, 2015 for U.S. Appl. No. 14/493,734.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office action dated Apr. 27, 2015 for U.S. Appl. No. 12/054,343.
Office action dated May 6, 2015 for U.S. Appl. No. 12/493,122.
Office action dated May 7, 2015 for U.S. Appl. No. 13/705,763.
Office action dated May 27, 2015 for U.S. Appl. No. 13/502,989.
Office action dated Jun. 3, 2015 for U.S. Appl. No. 13/002,136.
Office action dated Jul. 17, 2015 for U.S. Appl. No. 13/733,873.
Office action dated Aug. 24, 2015 for U.S. Appl. No. 13/733,873.
Office action dated Sep. 8, 2015 for U.S. Appl. No. 11/533,818.
Office action dated Sep. 10, 2015 for U.S. Appl. No. 13/313,629.
Office action dated Sep. 11, 2015 for U.S. Appl. No. 13/313,708.
Office action dated Oct. 30, 2015 for U.S. Appl. No. 14/528,715.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Dec. 10, 2015 for U.S. Appl. No. 13/836,135.
Office action dated Dec. 15, 2015 for U.S. Appl. No. 14/087,930.
Office action dated Dec. 18, 2015 for U.S. Appl. No. 14/640,385.
Richards, et al. Diagnosis, management, and treatment of Alzheimer disease: a guide for the internist. Arch Intern Med. Apr. 26, 1999;159(8):789-98.
Seltzer, et al. The Symptoms of Autism Spectrum Disorders in Adolescence and Adulthood. Journal of Autism and Developmental Disorders. 2003; 33(6):565-581.
Shelby, et al. Enzymatic debridement with activated whole pancreas. American Journal of Surgery. Oct. 1958; 96(4):545-549.
Swayne, et al. Pathobiology of H5N2 Mexican avian influenza virus infections of chickens. Vet Pathol. Nov. 1997;34(6):557-67.
ABCnews. Changing Face of Autism: Numbers Rise as More Behaviors Included. ABCnews. Nov. 1, 2007.
Aman, et al. Outcome measures for clinical drug trials in autism. CNS Spectr. Jan. 2004;9(1):36-47.
Ang, et al. Biological role and regulation of the universally conserved heat shock proteins. J Biol Chem. Dec. 25, 1991;266(36):24233-6.
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Ash. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.

Autism Society of America. Incidence Numbers from Other Countries. www.autism-society.org. Accessed: Jul. 14, 2008.
Awazuhara, et al. Antigenicity of the proteins in soy lecithin and soy oil in soybean allergy. Clin Exp Allergy. Dec. 1998;28(12):1559-64.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Birnbaum, et al. Heat shock or stress proteins and their role as autoantigens in multiple sclerosis. Ann N Y Acad Sci. Dec. 19, 1997;835:157-67. Abstract only.
Blog. Acid Phosphatase Research (blog). Acid-phosphatase.blogspot.com. 2008.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Brown. Background to Parkinson's Disease. biomed.brown.edu. Jul. 14, 2008.
Brudnak, Mark et al., Guide to intestinal health in autism spectrum disorder, Kirkman Laboratories, (Oct. 2001).
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Buie, et al. Evaluation, diagnosis, and treatment of gastrointestinal disorders in individuals with ASDs: a consensus report. Pediatrics. Jan. 2010;125 Suppl 1:S1-18.
Calderon-Garciduenas, et al. Immunotoxicity and environment: immunodysregulation and systemic inflammation in children. Toxicol Pathol. 2009;37(2):161-9.
Campbell, et al. Distinct genetic risk based on association of MET in families with co-occurring autism and gastrointestinal conditions. Pediatrics. Mar. 2009;123(3):1018-24.
Caronna, et al. Autism spectrum disorders: clinical and research frontiers. Arch Dis Child. Jun. 2008;93(6):518-23.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.

(56) References Cited

OTHER PUBLICATIONS

CDC. Attention-Deficit/Hyperactivity Disorder (ADHD). Www.cdc.org. 2005.
Cdc. Autism Information Center/FAQs. Dept of Health and Human Services/CDC. Jan. 30, 2008.
CDC. High Blood Pressure. Division for Heart Disease Stroke Prevention. Jul. 15, 2003.
Chazalette, A double-bind placebo-controlled trial of a pancreatic enzyme formulation (Panzytrat 25000) in the treatment of impaired lipid digestion in patients with cystic fibrosis RUG Invest., 5(5):274-280 (1993) Abstract Only.
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ The Complete Book of Enzyme Therapy, Penguin (1999) pp. 206-208 and 38.
Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Co-pending U.S. Appl. No. 15/164,493, filed May 25, 2016.
Co-pending U.S. Appl. No. 15/185,511, filed Jun. 17, 2016.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Croonenberghs, et al. Peripheral markers of serotonergic and noradrenergic function in post-pubertal, caucasian males with autistic disorder. Neuropsychopharmacology. Mar. 2000;22(3):275-83.
Cuervo, et al. Cathepsin A regulates chaperone-mediated autophagy through cleavage of the lysosomal receptor. EMBO J. Jan. 2, 2003;22(1):47-59.
Curemark Trademark/Service mark application, Principal Register. Serial No. 77527223. Filing date: Jul. 21, 2008.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Diaz-Hernandez, et al. Neuronal induction of the immunoproteasome in Huntington's disease. J Neurosci. Dec. 17, 2003;23(37):11653-61.
Ding, et al. Proteasome inhibition in oxidative stress neurotoxicity: implications for heat shock proteins. J Neurochem. May 2001;77(4):1010-7.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Durkin, et al. Socioeconomic inequality in the prevalence of autism spectrum disorder: evidence from a U.S. cross-sectional study. PLoS One. Jul. 12, 2010;5(7):e11551.
Edelson, et al. 3-Cyclohexene-1-glycine, an Isoleucine Antagonist. J. Am. Chem. Soc. 1958; 80(11):2698-2700.
Elphick, et al. Impaired luminal processing of human defensin-5 in Crohn's disease: persistence in a complex with chymotrypsinogen and trypsin. Am J Pathol. Mar. 2008;172(3):702-13.
Ethridge, et al. Acute pancreatitis results in induction of heat shock proteins 70 and 27 and heat shock factor-1. Pancreas. Oct. 2000;21(3):248-56.
European Application No. 15 200616.9 Extended Search Report dated Jun. 22, 2016.
European Application No. 16150552.4-1455 Extended European Search Report dated Jun. 24, 2016.
Exocrine Pancreatic Insufficiency (Enzymes) Document downloaded online on Jan. 8, 2016 at: http://www.epi4dogs.com/enzyme.htm <http:></http:>.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Family Caregiver Alliance. Fact Sheet: Parkinson's Disease. Caregiver. org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Fitzsimmons, et al. High-dose pancreatic-enzyme supplements and fibrosing colonopathy in children with cystic fibrosis. N Engl J Med. May 1, 1997;336(18):1283-9.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in *E. coli* stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Analysis of data gaps pertaining to enterotoxigenic *Escherichia coli* in low and medium human development index countries, 1984-2005. Epidemiol Infect. 2008; 136:721-738.
Gupta, et al. Th1- and Th2-like cytokines in CD4+ and CD8+ T cells in autism. J Neuroimmunol. May 1, 1998;85(1):106-9.

(56) References Cited

OTHER PUBLICATIONS

Hadjivassiliou, et al. Does cryptic gluten sensitivity play a part in neurological illness? Lancet. Feb. 10, 1996;347(8998):369-71.

Health.com. Who is affected by Parkinson's disease. www.health.com. Jul. 14, 2008.

Hitti. Allergy, celiac disease, and ileal lymphonodular. WebMD. 2005. 1-2.

Holquist et al. FDA safety page Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.

Horvath, et al. Autistic disorder and gastrointestinal disease. Curr Opin Pediatr. Oct. 2002; 14(5):583-7.

Horvath, et al. Gastrointestinal abnormalities in children with autistic disorder. J Pediatr. Nov. 1999;135(5):559-63.

Houston. Autism—One Conference. May 2006. 1-83.

Hsiao, et al. The microbes of the intestine: an introduction to their metabolic and signaling capabilities. Endocrinol Metab Clin North Am. Dec. 2008;37(4):857-71.

Huang, et al. Apoptotic cell death in mouse models of GM2 gangliosidosis and observations on human Tay-Sachs and Sandhoff diseases. Hum Mol Genet. Oct. 1997;6(11):1879-85.

Huang, et al. Mapping of the human APOB gene to chromosome 2p and demonstration of a two-allele restriction fragment length polymorphism. Proc Natl Acad Sci U S A. Feb. 1986;83(3):644-8.

James, et al. Thimerosal neurotoxicity is associated with glutathione depletion: protection with glutathione precursors. Neurotoxicology. 2004; 26(1):1-8.

Jeffrey. Global burden of hypertension may reach 1.5 billion by 2025. Medscape Medical News. Jul. 14, 2008.

Juhl. Fibromyalgia and the serotonin pathway. Altern Med Rev. 1998; 3(5):367-375.

Jyonouchi, et al. Dysregulated innate immune responses in young children with autism spectrum disorders: their relationship to gastrointestinal symptoms and dietary intervention. Neuropsychobiology. 2005;51(2):77-85.

Jyonouchi, et al. Evaluation of an association between gastrointestinal symptoms and cytokine production against common dietary proteins in children with autism spectrum disorders. J Pediatr. May 2005;146(5):605-10.

Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.

Kaemmerer, et al. Effects of lipid peroxidation-related protein modifications on RPE lysosomal functions and POS phagocytosis. Invest Ophthalmol Vis Sci. Mar. 2007;48(3):1342-7.

Kaminski, et al. Polymorphism of bovine beta-casein and its potential effect on human health. J Appl Genet. 2007;48(3):189-98.

Katritos. New finding may have implications for schizophrenia, autism. Autism/Schizophrenia findings relating to protein, etc. Feb. 10, 2011. e-mail.

Kearney, et al. Global burden of hypertension: analysis of worldwide data. Lancet. Jan. 15-21, 2005;365(9455):217-23. Abstract only.

Knivsberg, et al. A randomised, controlled study of dietary intervention in autistic syndromes. Nutr Neurosci. Sep. 2002;5(4):251-61.

Koller, et al. Falls and Parkinson's Disease (Abstract). Clin Neuropharmacol. 1989; 12(2):98-105.

Koplin, et al. Soy consumption is not a risk factor for peanut sensitization. J Allergy Clin Immunol. Jun. 2008;121(6):1455-9.

Kronenberg, et al. Folate deficiency induces neurodegeneration and brain dysfunction in mice lacking uracil DNA glycosylase. J Neurosci. Jul. 9, 2008;28(28):7219-30.

Kujoth, et al. Mitochondrial DNA mutations, oxidative stress, and apoptosis in mammalian aging. Science. Jul. 15, 2005;309(5733):481-4.

Kumar. Neurologic presentations of nutritional deficiencies. Neurol Clin. Feb. 2010;28(1):107-70.

Larimore. How Common Is ADHD? Facts About ADHD. Jul. 15, 2008.

Leyfer, et al. Comorbid psychiatric disorders in children with autism: interview development and rates of disorders. J Autism Dev Disord. Oct. 2006;36(7):849-61.

Life Plus Somazyne accessed Jun. 10, 2016, Online at www.lifeplus.com/media/pdf/piSheets/US/ 6141-PI_EN.pdf.

Lloyd. Lysosome membrane permeability: implications for drug delivery. Adv Drug Deliv Rev. Mar. 30, 2000;41(2):189-200.

Loh, et al. Highly tolerated amino acid substitutions increase the fidelity of *Escherichia coli* DNA polymerase I. J Biol Chem. Apr. 20, 2007;282(16):12201-9.

Lord, et al. Diagnostic Instruments in Autistic Spectrum Disorders. info.med.yale.edu. 2005; 11:730-771.

Luedtke, et al. Cathepsin A is expressed in a cell- and region-specific manner in the testis and epididymis and is not regulated by testicular or pituitary factors. J Histochem Cytochem. Aug. 2000;48(8):1131-46.

MacFabe, et al. Neurobiological effects of intraventricular propionic acid in rats: possible role of short chain fatty acids on the pathogenesis and characteristics of autism spectrum disorders. Behav Brain Res. 2006;176(1):149-69.

Mannino, et al. Surveillance for asthma—United States, 1960-1995. MMWR CDC Surveill Summ. Apr. 24, 1998;47(1):1-27.

Marcus, et al. A placebo-controlled, fixed-dose study of aripiprazole in children and adolescents with irritability associated with autistic disorder. J Am Acad Child Adolesc Psychiatry. Nov. 2009;48(11):1110-19.

Matikainen, et al. Autonomic dysfunction in long-standing alcoholism. Alcohol Alcohol. 1986;21(1):69-73. Abstract only.

Maurin, et al. Cellular adaptation to amino acid availability: mechanisms involved in the regulation of gene expression. 2006; 319-326.

McAlonan, et al. Brain anatomy and sensorimotor gating in Asperger's syndrome. ain. Jul. 2002;125(Pt 7):1594-606.

McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.

McCracken, et al. Risperidone in children with autism and serious behavioral problems. N Engl J Med. Aug. 1, 2002;347(5):314-21.

Medscape. Burden of Hypertension in the United States Greater Than Ever. www.medscape.com. Jul. 14, 2004.

Melmed, et al. Metabolic markers and gastrointestinal symptoms in children with autism and related disorders. J Pediatr Gast Nutr. 2000; 31:S31-S32. Abstract only.

Michael's Naturopathic Programs, Digestive Enzymes, Product #011161, Accessed on Jun. 10, 2016, online at: www.michaelshealth.com/retail/digestive-enzymes-659.html.

Minamino, et al. Vascular cell senescence: contribution to atherosclerosis. Circ Res. Jan. 5, 2007;100(1):15-26.

Ming, et al. Autism spectrum disorders: concurrent clinical disorders. J Child Neurol. Jan. 2008;23(1):6-13.

Mizutani, et al. Effects of placental proteases on maternal and fetal blood pressure in normal pregnancy and preeclampsia. Am J Hypertens. Jun. 1996;9(6):591-7.

Mononen, et al. Aspartylglycosaminuria in the Finnish population: identification of two point mutations in the heavy chain of glycoasparaginase. Proc Natl Acad Sci U S A. Apr. 1, 1991;88(7):2941-5.

Moretti, et al. Acute pancreatitis: hypertonic saline increases heat shock proteins 70 and 90 and reduces neutrophil infiltration in lung injury. Pancreas. Jul. 2009;38(5):507-14. Abstract only.

Mosqueira, et al. Chronic hypoxia impairs muscle function in the *Drosophila* model of Duchenne's muscular dystrophy (DMD). PLoS One. Oct. 20, 2010;5(10):e13450.

Nagamoto. Jacobson: Psychiatric Secrets, 2nd ed. 2001. Ch 28 Antipsychotic meds.

Neuer, et al. The role of heat shock proteins in reproduction. Hum Reprod Update. Mar.-Apr. 2000;6(2):149-59.

Newhorizons. ADD/ADHD: New Perspectives on Attentional Priority Disorders. New Horizons for Learning. Jul. 15, 2008.

(56) References Cited

OTHER PUBLICATIONS

NIH. National Institutes of Health. National Diabetes Statistics 2007. diabetes.niddk.nih.gov. Jun. 1, 2008.
Notice of allowance dated Mar. 1, 2016 for U.S. Appl. No. 14/087,930.
Notice of allowance dated Apr. 22, 2016 for U.S. Appl. No. 14/528,715.
Notice of allowance dated Dec. 23, 2015 for U.S. Appl. No. 12/493,122.
O'Connell. Hypertension Guide. cmbi.bjmu.edu. Jul. 14, 2008.
Office action dated Jan. 15, 2016 for U.S. Appl. No. 13/502,989.
Office action dated Jan. 26, 2016 for U.S. Appl. No. 12/054,343.
Office action dated Jan. 29, 2016 for U.S. Appl. No. 12/786,739.
Office action dated Feb. 1, 2016 for U.S. Appl. No. 13/503,844.
Office action dated Feb. 17, 2016 for U.S. Appl. No. 14/713,178.
Office action dated Mar. 2, 2016 for U.S. Appl. No. 14/693,711.
Office action dated Mar. 22, 2016 for U.S. Appl. No. 13/733,873.
Office action dated Mar. 30, 2016 for U.S. Appl. No. 14/296,091.
Office action dated Apr. 4, 2016 for U.S. Appl. No. 13/313,629.
Office action dated Apr. 5, 2016 for U.S. Appl. No. 14/713,242.
Office action dated Apr. 6, 2016 for U.S. Appl. No. 13/313,708.
Office action dated Apr. 13, 2016 for U.S. Appl. No. 14/612,604.
Office action dated Dec. 24, 2015 for U.S. Appl. No. 13/757,412.
Office Action dated May 11, 2016 U.S. Appl. No. 14/713,242.
Owley, et al. Multisite, double-blind, placebo-controlled trial of porcine secretin in autism. J Am Acad Child Adolesc Psychiatry. Nov. 2001;40(11):1293-9.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
PDTALKS. Motivational & Inspirational Speaking From a Parkinson's Patient Perspective. pdtalks.com/Parkinson_s_Disease.html. Jul. 14, 2008.
Persico, et al. Searching for ways out of the autism maze: genetic, epigenetic and environmental clues. Trends Neurosci. Jul. 2006;29(7):349-58.
Pisani, et al. Levodopa-induced dyskinesia and striatal signaling pathways. Proc Natl Acad Sci U S A. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatitis and pancreatic cancer from disease controls. Clin Gastroenterol Hepatol. Sep. 2003;1(5):397-403.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Reeves, G. et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Revolution health. Enzyme therapy. revolutionhealth.com/drugs-treatments/enzyme-therapy. Sep. 2, 2008.
Rider, et al. Perspective of biochemical research in the neuronal ceroid-lipofuscinosis. Am J Med Genet. Feb. 15, 1992;42(4):519-24.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes. raysahelian.com/enzymes.html. Sep. 2, 2008.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schizophreniform disorder. Merck Manuals Online Medical Library. Nov. 2005. (in Japanese with English translation).
Schneider, et al. Oral human immunoglobulin for children with autism and gastrointestinal dysfunction: a prospective, open-label study. J Autism Dev Disord. Nov. 2006;36(8):1053-64.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Skinner, et al. Treatment of Prion Disease with Heterologous Prion Proteins. PLoS One. Jul. 2, 2015;10(7):e0131993. doi: 10.1371/journal.pone.0131993. eCollection 2015.
Sousa, et al. Polymorphisms in leucine-rich repeat genes are associated with autism spectrum disorder susceptibility in populations of European ancestry. Mol Autism. Mar. 25, 2010;1(1):7.
Statemaster. Number of Children with Autism (most recent) by state. Statemaster.com Jul. 14, 2008.
Statemaster. Number of Children with Autism (most recent w/graph) by state. Statemaster.com Jul. 14, 2003.
Statemaster. Number of Children with Autism (per capita)(most recent) by state. Statemaster.com Jul. 14, 2003.
Steinherz, et al. Patterns of amino acid efflux from isolated normal and cystinotic human leucocyte lysosomes. J Biol Chem. Jun. 10, 1982;257(11):6041-9.

(56) References Cited

OTHER PUBLICATIONS

Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of ß-adrenergic receptor function. FASEB J. May 1989;3(7):1825-32.
Tager-Flusberg, et al. Language disorders: autism and other pervasive developmental disorders. Pediatr Clin North Am. Jun. 2007;54(3):469-81, vi.
Terrie, et al. Understanding Pancreatic Enzyme Products. Dec. 15, 2008.
Therapeutic research center. Approved Pancreatic Enzyme Products. Pharmacist's Letter/Prescriber's Letter 2010. Oct. 2010. 1-3.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Uhlmann, et al. Potential viral pathogenic mechanism for new variant inflammatory bowel disease. Mol Pathol. Apr. 2002;55(2):84-90.
Ultresa—FDA Prescribing Information Side Effects and Uses. Revised Sep. 2014.
Ultresa. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif. students triples. United Press International. Jul. 12, 2008.
U.S. Appl. No. 11/533,818 Final Office Action dated Jun. 7, 2016.
U.S. Appl. No. 13/002,136 Final Office Action dated Jun. 24, 2016.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/705,763 Final Office Action dated May 24, 2016.
U.S. Appl. No. 13/757,412 Final Office Action dated Jun. 30, 2016.
U.S. Appl. No. 13/836,135 Office Action dated Jul. 22, 2016.
U.S. Appl. No. 14/612,604 Notice of Allowance dated Jul. 20, 2016.
U.S. Appl. No. 14/639,425 Office Action dated Jul. 14, 2016.
U.S. Appl. No. 14/640,385 Supplemental Notice of Allowability dated May 26, 2016.
U.S. Appl. No. 14/713,221 Final Office Action dated Jun. 16, 2016.
U.S. Appl. No. 15/074,115, filed Mar. 18, 2016.
U.S. Appl. No. 15/089,842, filed Apr. 4, 2016.
U.S. Appl. No. 14/612,580 Office Action dated Dec. 24, 2015.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuro inflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Viokace—FDA Prescribing Information, Side Effects and Uses. Revised Mar. 2012.
Viokace. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Climical Perspectives in Autism. 2002; 74-81.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Wang, et al. Activation of Ras/Erk pathway by a novel MET-interacting protein RanBPM. J Biol Chem. Sep. 27, 2002;277(39):36216-22.
Wang, et al. Effect of chymotrypsin C and related proteins on pancreatic cancer cell migration. Acta Biochim Biophys Sin (Shanghai). May 2011;43(5):362-71. Epub Apr. 2, 2011. Jan. 7, 2011. Abstract only.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Witmer. ADD and ADHD Statistics—CDC Report Looks at Attention-Deficit/Hyperactivity Disorder. About.com—Parenting of Adolescents. Jul. 15, 2008.
Wolfson, D., Making sense of digestive enzymes, Klaire Labs, Mar. 13, 2006.

(56) References Cited

OTHER PUBLICATIONS

Yahoo!.com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zenpep—FDA Prescribing Information, Side Effects and Uses. Revised Sep. 2014.
Zenpep. Highlights of prescribing information. Eurand Pharmaceuticals Inc. Revised Jul. 2011.
Anonymous: Emulsifiers for the preparation of active dry yeast, Research Disclosure, Mason Publications, Hampshire, GB, 236(6), Dec. 1983 (attached).
Button, KS et al. Power failure: why small sample size undermines the reliability of neuroscience. Nat. Rev. Neurosci. 14:365376 (2013).
Co-pending U.S. Appl. No. 15/265,415, filed Sep. 14, 2016.
Co-pending U.S. Appl. No. 15265620, filed Sep. 14, 2016.
Co-pending U.S. Appl. No. 15/354,940, filed Nov. 17, 2016.
Co-pending U.S. Appl. No. 15/440,942, filed Feb. 23, 2017.
Riedel, L et al. Limitations of faecal chymotrypsin as a screening test for chronic pancreatitis. Gut, 32:321-324 (1991).
U.S. Appl. No. 12/054,343 Office Action dated Aug. 19, 2016.
U.S. Appl. No. 12/786,739 Office Action dated Sep. 20, 2016.
U.S. Appl. No. 13/002,136 Non-Final Office Action dated Feb. 27, 2017.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.
U.S. Appl. No. 13/503,844 Office Action dated Aug. 25, 2016.
U.S. Appl. No. 13/757,412 Office Action dated Feb. 10, 2017.
U.S. Appl. No. 14/296,091 Final Office Action dated Jan. 3, 2017.
U.S. Appl. No. 14/612,580 Office Action dated Sep. 21, 2016.
U.S. Appl. No. 14/693,711 Final Office Action dated Dec. 15, 2016.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,221 Non-Final Office Action dated Dec. 30, 2016.
U.S. Appl. No. 14/713,242 Office Action dated Dec. 7, 2016.
U.S. Appl. No. 14/639,425 Notice of Allowance dted Mar. 10, 2017.
Alexrod FB et al. Hereditary sensory an autonomic neuropathies: types II, III and IV. Orphanet Journal of Rare Diseases, 2:39 (2007).
Anderson, George M., et al. Determination of serotonin in whole blood, platelet-rich plasma, platelet-poor plasma and plasma ultrafiltrate. Life Sciences 40(11):1063-1070 (Mar. 16, 1987). (Abstract Only).
Arnold, GL et al. Plasma amino acids profiles in children with autism: potential risk of nutritional deficiencies. J. Autism Dev. Disord. 33(4):449-454 (Aug. 2003) (Abstract Only).
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Bouhnik, et al. Lactulose ingestion increases faecal bifidobacterial counts: A randomized double-blind study in healthy humans. European Journal of Clinical Nutrition 58:462-466 (2004).
Co-pending U.S. Appl. No. 15/840,883, filed Dec. 13, 2017.
Co-pending U.S. Appl. No. 15/889,917, filed Feb. 6, 2018.
Co-pending U.S. Appl. No. 16/010,850, filed Jun. 18, 2018.
Coutinho, AM et al. Variants of the serotonin transporter gene (SLC6A4) significantly contribute to hyperserotonemia in autism. Mol Psychiatry. Mar. 2004;9(3):264-71.
Fafournoux, P. et al. Amino acid regulation of gene expression. Biochemical Journal, 351:1-12(2000).
Girella, E. et al. The assay of chymotrypsin in stool as a simple and effective test of exocrine pancreatic activity in cystic fibrosis. Pancreas, 3(3):254-262 (1988).
Hamel, E. et al. Effects of Cocaine on Rat Pancreatic Enzyme Secretion and Protein Synthesis, Digestive Diseases, 23(3):264-268 (Mar. 1978).
International Application No. PCT/US18/26841 International Search Report and Written Opinion dated Jul. 3, 2018.
Nestler, et al. Delta-FosB: A sustained molecular switch for addiction. PNAS 98(20): 11042-11046 (Sep. 25, 2001).
Felig, P. Amino acid metabolism in man. Annual Review of Biochemistry, 44(1):933-955 (1975). (Abstract Only).
Chez, M. et al. Secretin and autism: A two-part clinical investigation. Journal of Autism and Developmental Disorders, 30(2), 87-94 (Apr. 2000).
Evans, C. et al. Altered amino acid excretion in children with autism. Nutritional Neuroscience, 11(1):9-17 (Feb. 2008).
First, M. Structured clinical interview for DSM-IV-TR axis I disorders, research version, patient edition. (SCID-I/P) New York: Biometrics Research, New York State Psychiatric Institute. (2002).
Guesnet, P. et al. Docosahexaenoic acid (DHA) and the developing central nervous system (CNS)—Implications for dietary recommendations. Biochem., 93(1):7-12(2011). (Abstract Only).
Heil, M., et al. Low endogenous fecal chymotrypsin: a possible biomarker for autism. Poster presented at the annual IMFAR Conference on Autism, Atlanta, GA.(May 2014) p. 1.
Matthews, D. Intestinal absorption of amino acids and peptides. Proceedings of the Nutrition Society, 31(2):171-177(1972).
McClung, C.A. et al. DeltaFosB: A molecular switch for long-term adaptation in the brain. Molecular Brain Research, 132(2):146-154 (Dec. 20, 2004). (Abstract Only).
Morimoto, R. The heat shock response: Systems biology of proteotoxic stress in aging and disease. Cold Spring Harbor Symposia on Quantitative Biology, 76:91-99 (2011) (Epub: Feb. 27, 2012). (Abstract Only).
Munasinghe, S.A. et al. Digestive enzyme supplementation for autism spectrum disorders: A double-blind randomized controlled trial. Journal of Autism and Developmental Disorders, 40(9):1131-1138 (Sep. 2010). (Abstract Only).
Naushad, Shaik Mohammad et al. Autistic children exhibit distinct plasma amino acid profile. Indian Journal of Biochemistry and Biophysics, 50(5):474-478 (Oct. 2013).
Nestler, E. et al. DeltaFosB: A sustained molecular switch for addiction. Proceedings of the National Academy of Sciences, 98(20):11042-11046 (Sep. 25, 2001).
Patton, J. et al. Factor structure of the barratt impulsiveness scale. Journal of Clinical Psychology, 51(6): 768-774 (Nov. 1995).
Robinson, T. et al. Incentive-sensitization and addiction. Addiction, 96(1):103-114 (Jan. 2001). (Abstract Only).
Schedl, H. et al. Absorption of l-methionine from the human small intestine. Journal of Clinical Investigation, 47(2): 417-425 (1968).
P.Ya. Grigoryev et al., Reference Guide on Gastroenterology, Moscow, MIA—2003, pp. 454,460,465.
Rivest, J. et al. A dynamic model of protein digestion in the small intestine of pigs. Journal of Animal Science, 78(2):328-240 (Feb. 2000) (Abstract Only).
Singh, Manjit. Alcoholic pancreatitis in rats fed ethanol in a nutritionally adequate liquid diet. International Journal of Pancreatology, 2:311-324 (1978).
Avruch, J., et al. Amino acid regulation of TOR complex 1. AJP: Endocrinology and Metabolism, Am. J. Physiol. Endocrinol. Metab. 296(4):E592-E602 (Apr. 2009).
Daly, E., et al. Response inhibition and serotonin in autism: A functional MRI study using acute tryptophan depletion. Brain, 137(9), 2600-2610 (Sep. 2014).

(56) References Cited

OTHER PUBLICATIONS

Drabkin, H., et al. Initiation of protein synthesis in mammalian cells with codons other than AUG and amino acids other than methionine. Molecular and Cellular Biology, 18(9): 5140-5147 (Sep. 1998).
Fairclough, P. et al. Comparison of the absorption of two protein hydrolysates and their effects on water and electrolyte movements in the human jejunum. Gut, 21(10):829-834 (1980).
McClung, C., et al. Regulation of gene expression and cocaine reward by CREB and DeltaFosB. Nature Neuroscience, 6(11):1208-1215 (2003). (Abstract Only).
Nestler, E.J. Molecular basis of long-term plasticity underlying addiction. Nature Reviews Neuroscience, 2(2):119-128 (Feb. 2001). (Abstract Only).
Norton, L. et al. Leucine regulates translation initiation of protein synthesis in skeletal muscle after exercise. The Journal of Nutrition, 136(2):533S-537S (Feb. 2006).
Schain, RJ et al. Studies on 5-hydroxyindole metabolism in autistic and other mentally retarded children. J. Pediatr. 58:315-320 (1961). (Summary Only).
Tang, G. et al. Loss of mTOR-dependent macroautophagy causes autistic-like synaptic pruning deficits. Neuron, 83(5):1131-1143 (Sep. 3, 2014).
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). (Abstract Only).
Tuohy, K.M. et al. Using probiotics and prebiotics to improve gut health. Reviews, Therapeutic Focus, DDT 8(15) Aug. 2003.
U.S. Appl. No. 12/054,343 Non-Final Office Action dated Dec. 26, 2017.
U.S. Appl. No. 12/786,739 Non-Final Office Action dated Jan. 4, 2018.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/503,844 Final Office Action dated Nov. 30, 2017.
U.S. Appl. No. 13/733,873 Final Office Action dated Feb. 21, 2018.
U.S. Appl. No. 13/836,135 Non-Final Office Action dated Mar. 15, 2018.
U.S. Appl. No. 14/296,091 Non-Final Office Action dated Mar. 22, 2018.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/713,221 Notice of Allowance dated Oct. 19, 2017.
U.S. Appl. No. 14/713,242 Non-Final Office Action dated Mar. 29, 2018.
U.S. Appl. No. 14/921,896 Final Office Action dated Jan. 25, 2018.
U.S. Appl. No. 14/921,896 Notice of Allowance dated Jul. 18, 2018.
U.S. Appl. No. 15/089,842 Non-Final Office Action dated Jun. 26, 2018.
U.S. Appl. No. 15/089,842 Office Action dated Dec. 8, 2017.
U.S. Appl. No. 15/164,493 Non-Final Office Action dated Feb. 27, 2018.
U.S. Appl. No. 15/185,511 Notice of Allowance dated Nov. 16, 2017.
U.S. Appl. No. 15/265,415 Non-Final Office Action dated Apr. 11, 2018.
U.S. Appl. No. 15/265,620 Non-Final Office Action dated Jun. 20, 2018.
U.S. Appl. No. 15/593,121 Non-Final Office Action dated Mar. 8, 2018.
Cgaignon et al. Susceptibility of staphylococcal biofilms to enzymatic treatments depends on their chemical compositions. Appl. Microbiol. Appl. Microbiol. 75:125-132 (2007).
Co-pending U.S. Appl. No. 15/593,121, filed May 11, 2017.
Co-pending U.S. Appl. No. 15/593,124, filed May 11, 2017.
Co-pending U.S. Appl. No. 15/593,129, filed May 11, 2017.
DeMasi, Carl B. The Role of Enzymatic Detergents in Washing Medical Devices and Removing Contaminants from Them, National Diet 73:28-35 (May 2002).
Kidd, P.M., Autism, an extreme challenge to integrative medicine. Part 2: medical management. Altern. Med. Rev., 7(6):172-499 (Dec. 2002).
Marion et al., A New Procedure Allowing the Complete Removal and Prevention of Hemodialysis. Blood Purification, 23:339-348 (2005).
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
U.S. Appl. No. 12/054,343 Final Office Action dated May 10, 2017.
U.S. Appl. No. 12/786,739 Final Office Action dated Jun. 23, 2017.
U.S. Appl. No. 13/503,844 Office Action dated Mar. 27, 2017.
U.S. Appl. No. 13/733,873 Non-Final Office Action dated May 25, 2017.
U.S. Appl. No. 13/836,135 Final Office Action dated May 15, 2017.
U.S. Appl. No. 14/296,091 Final Office Action dated Aug. 23, 2017.
U.S. Appl. No. 14/612,580 Final Office Action dated Aug. 10, 2017.
U.S. Appl. No. 14/693,711 Notice of Allowability dated May 26, 2017.
U.S. Appl. No. 14/693,711 Notice of Allowance dated Apr. 21, 2017.
U.S. Appl. No. 14/713,178 Notice of Allowance dated Apr. 12, 2017.
U.S. Appl. No. 14/713,242 Final Office Action dated Jul. 21, 2017.
U.S. Appl. No. 14/921,896 Office Action dated Apr. 26, 2017.
American Family Physician. Cuts, Scrapes, and Stitches. Am Fam Physician 69(11):2647-2648 (Jun. 1, 2004).
Beliaev, O.A. The therapeutic efficacy of the triase preparation in experimental pancreatic exocrine insufficiency. Eksp Lin Farmakiol. 57:38-40 (1994) (Abstract Only—English Translation).
Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013).
Carroccio et al. Effectiveness of Enteric-coated Preparations on Nutritional Parameters in Cystic Fibrosis. Digestion 41:201-206 (1988).
Carroccio et al. Role of pancreatic impairment in growth recovery during gluten-free diet in childhood celiac disease. Gastroenterology 112:1839-1844 (1997).
Cichoke. Influenza. In: The Complete Book of Enzyme Therapy. Anthony J. Cichoke. Avery, a member of Penguin Putnam, Inc., publisher. Ed.: Dara Stewart, pp. 37, 40-45 (1999).
Cornish. A balanced approach towards healthy eating in autism, Journal of Human Nutrition and Dietetics 11:501-509 (1998).
Cox, RJ et al. Influenza Virus: Immunity and Vaccination Strategies. Comparison of the Immune Response to Inactivated and Live, Attenuated Influenza Vaccines. Scandinavian Journal of Immunology 59, 1-15 (2004).
Diagnostic and Statistical Manual of Mental Disorders, Fourth Edition, Primary Care Version, Chapter 6, American Psychiatric Association (2000).
Diagnostic and Statistical Manual of Mental Disorders, Fourth Edition, Text Revision, DSM-IV-TR, American Psychiatric Association (2000).
Dudzinska. Dissertation. Development of lipid-based enteric coatings. Oct. 18, 1988. Martin Luther University, Halle-Wittenberg. pp. 1-125.
Durie et al. Uses and abuses of enzyme therapy in cystic fibrosis. Journal of the Royal Society of Medicine. 91:(Suppl. 34):2-13 (1998).
Flament, M.P. et al. Development of 400 μm Pellets by Extrusion-Spheronization Application with Gelucire 50/02 to Produce a "Sprinkle" Form, Drug Development and industrial Pharmacy, 30:1, 43-51, DOI: 10.1081/DDC-120027510 (2004).
Ijuin, H. Evaluation of pancreatic exocrine function and zinc absorption in alcoholism. The Kurume Medical Journal 45.1 (1998): 1-5.

(56) References Cited

OTHER PUBLICATIONS

International Preliminary Report on Patentability dated Oct. 15, 2019 for PCT/US2018/026841.
Johnson et al. Eating Habits and Dietary Status in Young Children with Autism. J Dev Phys Disabil 20:437-448 (2008).
Keeley et al., Gradual vs. abrupt withdrawal of methylphenidate in two older dependent males. Journal of Substance Abuse Treatment. 2(2):123-125 (1985).
Keller, et al. Pancreatic enzyme supplementation therapy. Current Treatment Options in Gastroenterology 6.5 (2003): 369-374.
Klopfleisch et al. Encephalitis in a stone marten (Martes foina) after natural infection with highly pathogenic avian influenza virus subtype H5N1. Journal of Comparative Pathology 137:155-159 (2007).
Koh et al. Inflammation and wound healing: The role of the macrophage. Expert Rev Mol Med. 13:e23 (Author manuscript).
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Lockner et al. Dietary intake and parents' perception of mealtime behaviors in preschool-age children with autism spectrum disorder and in typically developing children. J Am Diet Assoc 108(8):1360-1363 (2008).
Medori et al. Fatal Familial Insomnia, A Prion Disease With a Mutation At Condon 178 of The Prion Protein Case. N Engl J Med 326:444-449 (1992).
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Naver.com entry for Rare Disease Information: Osteopenia—Osteopsathyrosis, Fragilitasossium, Fragilitasossium (accessed Sep. 25, 2019).
No Author. RSDSA, 2015: Telltale signs and symptoms of CRPS/RSD on the web at rsds.org/telltale-signs-and-symptoms-of-crpsrsd. [Accessed: Sep. 5, 2018].
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Pending U.S. Appl. No. 16/499,988, filed Oct. 1, 2019.
Qi, et al. Solubility and emulsifying properties of soy protein isolates modified by pancreatin. Journal of Food Science 62.6 (1997): 1110-1115.
Salpekar, et al. Bipolar Spectrum Disorder Comorbid With Autism Spectrum Disorder; NADD Bulletin, vol. X, 2007. No. 6, Article 1, pp. 1-5, downloaded from http://www.thenadd.org/nadd-bulletin/archive/volunne-x/ on Dec. 11, 2018.
Singh et al. Past, Present, and Future Technologies for Oral Delivery of Therapeutic Proteins. J Pham Sci 97(7):2497-2523 (2008).
U.S. Appl. No. 12/786,739 Final Office Action dated Sep. 25, 2018.
U.S. Appl. No. 13/002,136 Non-Final Office Action dated Dec. 18, 2018.
U.S. Appl. No. 13/757,412 Final Office Action dated Sep. 12, 2017.
U.S. Appl. No. 13/757,412 Office Action dated Apr. 16, 2019.
U.S. Appl. No. 13/836,135 Final Office Action dated Dec. 14, 2018.
U.S. Appl. No. 13/836,135 Notice of Allowance dated Apr. 25, 2019.
U.S. Appl. No. 14/296,091 Final Office Action dated Oct. 1, 2018.
U.S. Appl. No. 14/713,242 Final Office Action dated Jan. 9, 2019.
U.S. Appl. No. 14/921,896 Notice of Allowability dated Sep. 12, 2018.
U.S. Appl. No. 15/089,842 Final Office Action dated Dec. 4, 2018.
U.S. Appl. No. 15/164,493 Notice of Allowance dated Nov. 15, 2018.
U.S. Appl. No. 15/265,620 Non-Final Office Action dated Jan. 22, 2019.
U.S. Appl. No. 15/354,940 Non-Final Office Action dated Nov. 2, 2018.
U.S. Appl. No. 15/593,129 Office Action dated Jan. 3, 2019.
U.S. Appl. No. 16/103,192 Office Action dated Nov. 4, 2019.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/265,415 Notice of Allowance dated Dec. 26, 2018.
U.S. Appl. No. 15/354,940 Final Office Action date Aug. 21, 2019.
U.S. Appl. No. 15/593,121 Notice of Allowance dated Dec. 26, 2018.
U.S. Appl. No. 15/840,883 Office Action dated Aug. 8, 2019.
U.S. Appl. No. 13/002,136 Office Action dated Jun. 21, 2019.
U.S. Appl. No. 15/074,115 Notice of Allowance dated Dec. 11, 2019.
U.S. Appl. No. 15/089,842 Notice of Allowance dated Mar. 29, 2019.
Yang, Xinyi et al. Advances in anti-staphylococcal agent lysostaphin. Chinese Journal of New Drugs 14(9):1113-1117 (2005).
U.S. Appl. No. 15/889,917 Final Office Action dated Feb. 13, 2020.
U.S. Appl. No. 15/074,115 Notice of Allowance dated Feb. 11, 2020.
U.S. Appl. No. 16/296,546 Non-Final Office Action dated Feb. 14, 2020.

\* cited by examiner

UNIFIED PARKINSON'S DISEASE RATING SCALE

---

*I. MENTATION, BEHAVIOR AND MOOD*

1. Intellectual Impairment
0 = None.
1 = Mild. Consistent forgetfulness with partial recollection of events and no other difficulties.
2 = Moderate memory loss, with disorientation and moderate difficulty handling complex problems. Mild but definite impairment of function at home with need of occasional prompting.
3 = Severe memory loss with disorientation for time and often to place. Severe impairment in handling problems.
4 = Severe memory loss with orientation preserved to person only. Unable to make judgements or solve problems. Requires much help with personal care. Cannot be left alone at all.

2. Thought Disorder (Due to dementia or drug intoxication)
0 = None.
1 = Vivid dreaming.
2 = "Benign" hallucinations with insight retained.
3 = Occasional to frequent hallucinations or delusions; without insight; could interfere with daily activities.
4 = Persistent hallucinations, delusions, or florrid psychosis. Not able to care for self.

3. Depression
1 = Periods of sadness or guilt greater than normal, never sustained for days or weeks.
2 = Sustained depression (1 week or more).
3 = Sustained depression with vegetative symptoms (insomnia, anorexia, weight loss, loss of interest).
4 = Sustained depression with vegetative symptoms and suicidal thoughts or intent.

4. Motivation/Initiative
0 = Normal.
1 = Less assertive than usual; more passive.
2 = Loss of initiative or disinterest in elective (nonroutine) activities.
3 = Loss of initiative or disinterest in day to day (routine) activities.
4 = Withdrawn, complete loss of motivation.

---

*II. ACTIVITIES OF DAILY LIVING (for both "on" and "off")*

5. Speech
0 = Normal.
1 = Mildly affected. No difficulty being understood.
2 = Moderately affected. Sometimes asked to repeat statements.
3 = Severely affected. Frequently asked to repeat statements.
4 = Unintelligible most of the time.

6. Salivation
0 = Normal.
1 = Slight but definite excess of saliva in mouth; may have nighttime drooling.
2 = Moderately excessive saliva; may have minimal drooling.
3 = Marked excess of saliva with some drooling.
4 = Marked drooling, requires constant tissue or handkerchief.

7. Swallowing
0 = Normal.
1 = Rare choking.
2 = Occasional choking.
3 = Requires soft food.
4 = Requires NG tube or gastrotomy feeding.

8. Handwriting
0 = Normal.
1 = Slightly slow or small.
2 = Moderately slow or small; all words are legible.
3 = Severely affected; not all words are legible.
4 = The majority of words are not legible.

9. Cutting food and handling utensils
0 = Normal.
1 = Somewhat slow and clumsy, but no help needed.
2 = Can cut most foods, although clumsy and slow; some help needed.
3 = Food must be cut by someone, but can still feed slowly.
4 = Needs to be fed.

10. Dressing
0 = Normal.
1 = Somewhat slow, but no help needed.
2 = Occasional assistance with buttoning, getting arms in sleeves.
3 = Considerable help required, but can do some things alone.
4 = Helpless.

11. Hygiene
0 = Normal.
1 = Somewhat slow, but no help needed.
2 = Needs help to shower or bathe; or very slow in hygienic care.
3 = Requires assistance for washing, brushing teeth, combing hair, going to bathroom.
4 = Foley catheter or other mechanical aids.

12. Turning in bed and adjusting bed clothes
0 = Normal.
1 = Somewhat slow and clumsy, but no help needed.
2 = Can turn alone or adjust sheets, but with great difficulty.
3 = Can initiate, but not turn or adjust sheets alone.
4 = Helpless.

13. Falling (unrelated to freezing)
0 = None.
1 = Rare falling.
2 = Occasionally falls, less than once per day.
3 = Falls an average of once daily.
4 = Falls more than once daily.

14. Freezing when walking
0 = None.
1 = Rare freezing when walking; may have starthesitation.
2 = Occasional freezing when walking.
3 = Frequent freezing. Occasionally falls from freezing.
4 = Frequent falls from freezing.

15. Walking
0 = Normal.
1 = Mild difficulty. May not swing arms or may tend to drag leg.
2 = Moderate difficulty, but requires little or no assistance.
3 = Severe disturbance of walking, requiring assistance.
4 = Cannot walk at all, even with assistance.

16. Tremor (Symptomatic complaint of tremor in any part of body.)
0 = Absent.
1 = Slight and infrequently present.
2 = Moderate; bothersome to patient.
3 = Severe; interferes with many activities.
4 = Marked; interferes with most activities.

17. Sensory complaints related to parkinsonism
0 = None.
1 = Occasionally has numbness, tingling, or mild aching.
2 = Frequently has numbness, tingling, or aching; not distressing.
3 = Frequent painful sensations.
4 = Excruciating pain.

---

*III. MOTOR EXAMINATION*

18. Speech
0 = Normal.
1 = Slight loss of expression, diction and/or volume.
2 = Monotone, slurred but understandable; moderately impaired.
3 = Marked impairment, difficult to understand.
4 = Unintelligible.

19. Facial Expression
0 = Normal.
1 = Minimal hypomimia, could be normal "Poker Face".
2 = Slight but definitely abnormal diminution of facial expression
3 = Moderate hypomimia; lips parted some of the time.
4 = Masked or fixed facies with severe or complete loss of facial expression; lips parted 1/4 inch or more FIGURE 6c

20. Tremor at rest (head, upper and lower extremities)
0 = Absent.
1 = Slight and infrequently present.
2 = Mild in amplitude and persistent. Or moderate in amplitude, but only intermittently present.
3 = Moderate in amplitude and present most of the time.
4 = Marked in amplitude and present most of the time.

21. Action or Postural Tremor of hands
0 = Absent.
1 = Slight; present with action.
2 = Moderate in amplitude, present with action.
3 = Moderate in amplitude with posture holding as well as action.
4 = Marked in amplitude; interferes with feeding.

22. Rigidity (Judged on passive movement of major joints with patient relaxed in sitting position. Cogwheeling to be ignored.)
0 = Absent.
1 = Slight or detectable only when activated by mirror or other movements.
2 = Mild to moderate.
3 = Marked, but full range of motion easily achieved.
4 = Severe, range of motion achieved with difficulty.

23. Finger Taps (Patient taps thumb with index finger in rapid succession.)
0 = Normal.
1 = Mild slowing and/or reduction in amplitude.
2 = Moderately impaired. Definite and early fatiguing. May have occasional arrests in movement.
3 = Severely impaired. Frequent hesitation in initiating movements or arrests in ongoing movement.
4 = Can barely perform the task.

24. Hand Movements (Patient opens and closes hands in rapid succesion.)
0 = Normal.
1 = Mild slowing and/or reduction in amplitude.
2 = Moderately impaired. Definite and early fatiguing. May have occasional arrests in movement.
3 = Severely impaired. Frequent hesitation in initiating movements or arrests in ongoing movement.
4 = Can barely perform the task.

25. Rapid Alternating Movements of Hands (Pronation-supination movements of hands, vertically and horizontally, with as large an amplitude as possible, both hands simultaneously.)
0 = Normal.
1 = Mild slowing and/or reduction in amplitude.
2 = Moderately impaired. Definite and early fatiguing. May have occasional arrests in movement.
3 = Severely impaired. Frequent hesitation in initiating movements or arrests in ongoing movement.
4 = Can barely perform the task.

26. Leg Agility (Patient taps heel on the ground in rapid succession picking up entire leg. Amplitude should be at least 3 inches.)
0 = Normal.
1 = Mild slowing and/or reduction in amplitude.
2 = Moderately impaired. Definite and early fatiguing. May have occasional arrests in movement.
3 = Severely impaired. Frequent hesitation in initiating movements or arrests in ongoing movement.
4 = Can barely perform the task.

27. Arising from Chair (Patient attempts to rise from a straightbacked chair, with arms folded across chest.)
0 = Normal.
1 = Slow; or may need more than one attempt.
2 = Pushes self up from arms of seat.
3 = Tends to fall back and may have to try more than one time, but can get up without help.
4 = Unable to arise without help.

28. Posture
0 = Normal erect.
1 = Not quite erect, slightly stooped posture; could be normal for older person.
2 = Moderately stooped posture, definitely abnormal; can be slightly leaning to one side.
3 = Severely stooped posture with kyphosis; can be moderately leaning to one side.
4 = Marked flexion with extreme abnormality of posture.

29. Gait
0 = Normal.
1 = Walks slowly, may shuffle with short steps, but no festination (hastening steps) or propulsion.
2 = Walks with difficulty, but requires little or no assistance; may have some festination, short steps, or propulsion.
3 = Severe disturbance of gait, requiring assistance.
4 = Cannot walk at all, even with assistance.

30. Postural Stability (Response to sudden, strong posterior displacement produced by pull on shoulders while patien erect with eyes open and feet slightly apart. Patient is prepared.)
0 = Normal.
1 = Retropulsion, but recovers unaided.
2 = Absence of postural response; would fall if not caught by examiner.
3 = Very unstable, tends to lose balance spontaneously.
4 = Unable to stand without assistance.

31. Body Bradykinesia and Hypokinesia (Combining slowness, hesitancy, decreased armswing, small amplitude, and poverty of movement in general.)
0 = None.
1 = Minimal slowness, giving movement a deliberate character; could be normal for some persons. Possibly reduced amplitude.
2 = Mild degree of slowness and poverty of movement which is definitely abnormal. Alternatively, some reduced amplitude.
3 = Moderate slowness, poverty or small amplitude of movement.
4 = Marked slowness, poverty or small amplitude of movement.

---

IV. COMPLICATIONS OF THERAPY (In the past week)

A. DYSKINESIAS

32. Duration: What proportion of the waking day are dyskinesias present? (Historical information.)
0 = None
1 = 1-25% of day.
2 = 26-50% of day.
3 = 51-75% of day.
4 = 76-100% of day.

33. Disability: How disabling are the dyskinesias? (Historical information; may be modified by office examination.)
0 = Not disabling.
1 = Mildly disabling.
2 = Moderately disabling.
3 = Severely disabling.
4 = Completely disabled.

34. Painful Dyskinesias: How painful are the dyskinesias?
0 = No painful dyskinesias.
1 = Slight.
2 = Moderate.
3 = Severe.
4 = Marked.

35. Presence of Early Morning Dystonia (Historical information.)
0 = No
1 = Yes

B. CLINICAL FLUCTUATIONS

36. Are "off" periods predictable?
0 = No
1 = Yes

37. Are "off" periods unpredictable?
0 = No
1 = Yes

38. Do "off" periods come on suddenly, within a few seconds?
0 = No
1 = Yes

39. What proportion of the waking day is the patient "off" on average?
0 = None
1 = 1-25% of day.
2 = 26-50% of day.
3 = 51-75% of day.
4 = 76-100% of day.

C. OTHER COMPLICATIONS

40. Does the patient have anorexia, nausea, or vomiting?
0 = No
1 = Yes

FIGURE 6d

41. Any sleep disturbances, such as insomnia or hypersomnolence?
0 = No
1 = Yes

42. Does the patient have symptomatic orthostasis?
( Record the patient's blood pressure, height and weight on the scoring form)
0 = No
1 = Yes

V. MODIFIED HOEHN AND YAHR STAGING

STAGE 0 = No signs of disease.
STAGE 1 = Unilateral disease.
STAGE 1.5 = Unilateral plus axial involvement.
STAGE 2 = Bilateral disease, without impairment of balance.
STAGE 2.5 = Mild bilateral disease, with recovery on pull test.
STAGE 3 = Mild to moderate bilateral disease; some postural instability; physically independent.
STAGE 4 = Severe disability; still able to walk or stand unassisted.
STAGE 5 = Wheelchair bound or bedridden unless aided.

VI. SCHWAB AND ENGLAND ACTIVITIES OF DAILY LIVING SCALE

100% = Completely independent. Able to do all chores without slowness, difficulty or impairment. Essentially normal. Unaware of any difficulty.
90% = Completely independent. Able to do all chores with some degree of slowness, difficulty and impairment. Might take twice as long. Beginning to be aware of difficulty.
80% = Completely independent in most chores. Takes twice as long. Conscious of difficulty and slowness.
70% = Not completely independent. More difficulty with some chores. Three to four times as long in some. Must spend a large part of the day with chores.
60% = Some dependency. Can do most chores, but exceedingly slowly and with much effort. Errors; some impossible.
50% = More dependent. Help with half, slower, etc. Difficulty with everything.
40% = Very dependent. Can assist with all chores, but few alone.
30% = With effort, now and then does a few chores alone or begins alone. Much help needed.
20% = Nothing alone. Can be a slight help with some chores. Severe invalid.
10% = Totally dependent, helpless. Complete invalid.
0% = Vegetative functions such as swallowing, bladder and bowel functions are not functioning. Bedridden.

FIGURE 6e

UNIFIED PARKINSON'S DISEASE DATA FORM

| Name: | | | | | | | | | | | | Unit Number: | | | | | | |
|---|---|---|---|---|---|---|---|---|---|---|---|---|---|---|---|---|---|---|
| | | Date: | | | | | | | | | | | | | | | | |
| | DOPA mg/day | hrs DOPA lasts | | | | | | | | | | | | | | | | |
| | | | On | Off | On | Off | On | Off | On | Off | On | Off | On | Off | On | Off | On | Off |
| 1 | Mentation | | | | | | | | | | | | | | | | | |
| 2 | Thought Disorder | | | | | | | | | | | | | | | | | |
| 3 | Depression | | | | | | | | | | | | | | | | | |
| 4 | Motivation/Initiative | | | | | | | | | | | | | | | | | |
| | Subtotal 1-4 (maximum=16) | | | | | | | | | | | | | | | | | |
| 5 | Speech | | | | | | | | | | | | | | | | | |
| 6 | Salivation | | | | | | | | | | | | | | | | | |
| 7 | Swallowing | | | | | | | | | | | | | | | | | |
| 8 | Handwriting | | | | | | | | | | | | | | | | | |
| 9 | Cutting food | | | | | | | | | | | | | | | | | |
| 10 | Dressing | | | | | | | | | | | | | | | | | |
| 11 | Hygiene | | | | | | | | | | | | | | | | | |
| 12 | Turning in bed | | | | | | | | | | | | | | | | | |
| 13 | Falling | | | | | | | | | | | | | | | | | |
| 14 | Freezing | | | | | | | | | | | | | | | | | |
| 15 | Walking | | | | | | | | | | | | | | | | | |
| 16 | Tremor | | | | | | | | | | | | | | | | | |
| 17 | Sensory symptoms | | | | | | | | | | | | | | | | | |
| | Subtotal 5-17 (maximum=52) | | | | | | | | | | | | | | | | | |
| 18 | Speech | | | | | | | | | | | | | | | | | |
| 19 | Facial expression | | | | | | | | | | | | | | | | | |
| 20 | Tremor at rest: face,lips,chin | | | | | | | | | | | | | | | | | |
| | Hands: right | | | | | | | | | | | | | | | | | |
| | left | | | | | | | | | | | | | | | | | |
| | Feet: right | | | | | | | | | | | | | | | | | |
| | left | | | | | | | | | | | | | | | | | |
| 21 | Action tremor: right | | | | | | | | | | | | | | | | | |
| | left | | | | | | | | | | | | | | | | | |
| 22 | Rigidity: neck | | | | | | | | | | | | | | | | | |
| | Upper extremity: right | | | | | | | | | | | | | | | | | |
| | left | | | | | | | | | | | | | | | | | |
| | Lower extremity: right | | | | | | | | | | | | | | | | | |
| | left | | | | | | | | | | | | | | | | | |

Figure 7A

| | Date: | | | | | | | | | | | | | | | |
|---|---|---|---|---|---|---|---|---|---|---|---|---|---|---|---|---|
| | | On | Off | On | Off | On | Off | On | Off | On | Off | On | Off | On | Off | On | Off |
| 23 | Finger taps: right | | | | | | | | | | | | | | | | |
| | left | | | | | | | | | | | | | | | | |
| 24 | Hand grips: right | | | | | | | | | | | | | | | | |
| | left | | | | | | | | | | | | | | | | |
| 25 | Hand pronate/supinate: right | | | | | | | | | | | | | | | | |
| | left | | | | | | | | | | | | | | | | |
| 26 | Leg agility: right | | | | | | | | | | | | | | | | |
| | left | | | | | | | | | | | | | | | | |
| 27 | Arise from chair | | | | | | | | | | | | | | | | |
| 28 | Posture | | | | | | | | | | | | | | | | |
| 29 | Gait | | | | | | | | | | | | | | | | |
| 30 | Postural stability | | | | | | | | | | | | | | | | |
| 31 | Body bradykinesis | | | | | | | | | | | | | | | | |
| | Sub-total:18-31(maximum=108) | | | | | | | | | | | | | | | | |
| | Total points:1-31(max=176) | | | | | | | | | | | | | | | | |
| 32 | Dyskinesia (duration) | | | | | | | | | | | | | | | | |
| 33 | Dyskinesia (disability) | | | | | | | | | | | | | | | | |
| 34 | Dyskinesia (pain) | | | | | | | | | | | | | | | | |
| 35 | Early morning dystonia | | | | | | | | | | | | | | | | |
| 36 | "Offs" (predictable) | | | | | | | | | | | | | | | | |
| 37 | "Offs" (unpredictable) | | | | | | | | | | | | | | | | |
| 38 | "Offs" (sudden) | | | | | | | | | | | | | | | | |
| 39 | "Offs" (duration) | | | | | | | | | | | | | | | | |
| 40 | Anorexia, nausea, vomiting | | | | | | | | | | | | | | | | |
| 41 | Sleep disturbance | | | | | | | | | | | | | | | | |
| 42 | Symptomatic orthostasis | | | | | | | | | | | | | | | | |
| | Blood Pressure: seated | | | | | | | | | | | | | | | | |
| | supine | | | | | | | | | | | | | | | | |
| | standing | | | | | | | | | | | | | | | | |
| | Weight | | | | | | | | | | | | | | | | |
| | Pulse: seated | | | | | | | | | | | | | | | | |
| | standing | | | | | | | | | | | | | | | | |
| Name of examiner | | | | | | | | | | | | | | | | | |
| | | Best | Worst | Best | Worst | Best | Worst | Best | Worst | Best | Worst | Best | Worst | Best | Worst | Best | Worst |
| | Hoehn & Yahr Stage | | | | | | | | | | | | | | | | |
| | % ADL Score (PD) | | | | | | | | | | | | | | | | |
| | % ADL (with dyskinesia) | | | | | | | | | | | | | | | | |

Fahn S, Elton R, Members of the UPDRS Development Committee.
In: Fahn S, Marsden CD, Calne DB, Goldstein M, eds. Recent Developments in Parkinson's Disease, Vol 2. Florham Park, NJ. Macmillan Health Care Information 1987; pp 153-163, 293-304

Figure 7B

IMPLEMENTATION OF UNIFIED PARKINSON'S DISEASE RATING SCALE

| No | Test Target | Description | Basic | Complex | Comprehensive |
|----|-------------|-------------|-------|---------|---------------|
| 1 | Mentation | Questionnaire, short term memory shapes, words, colors. | √ | | |
| 2 | Thought Disorder | Questionnaire | | | √ |
| 3 | Depression | Questionnaire | √ | | |
| 4 | Motivation/Initiative | Questionnaire | √ | | |
| 5 | Speech | Voice capture for later physician analysis (repeat standard phrases on screen prompt) Constant distance. | √ | | |
| 6 | Salivation | Questionnaire | | √ | |
| 7 | Swallowing | Questionnaire | √ | | |
| 8 | Handwriting | Use of commercial signature verification systems to digitize angle, pressure and direction of writing utensil on a surface using a standard sentence. Software needed to develop for analysis of test-to-test variations; Relay of visual copy to researcher for analysis. | | | |
| 9 | Cutting Food | Questionnaire | | √ | √ |
| 10 | Dressing | Questionnaire | √ | | |
| 11 | Hygiene | Questionnaire | √ | | |
| 12 | Turning in bed | Questionnaire | √ | | √ |
| 13 | Falling | Questionnaire | √ | | |
| 14 | Freezing | Questionnaire | √ | | |
| 15 | Walking | Commercial solution available for measure | | √ | |

FIGURE 8A

IMPLEMENTATION OF UNIFIED PARKINSON'S DISEASE RATING SCALE

| No | Test Target | Description | Level of Use - Basic | Level of Use - Complex | Level of Use - Comprehensive |
|---|---|---|---|---|---|
| | | of walking using a pad and sensors in patient's shoes. Video capture at standard distance. Relay to researcher for subsequent observation. Questionnaire | | | |
| 16 | Tremor (symptomatic tremor in any body part) | Upper extremity accelerometer | √ | | |
| 17 | Sensory Symptoms | Questionnaire | | √ | |
| 18 | Speech | Voice capture for later physician analysis (repeat standard phrases; on screen prompt) Constant distance. | √ | | |
| 19 | Facial Expressions | Video capture while interacting with test system; relay to researcher for subsequent analysis | | √ | |
| 20 | Tremor at rest: Face, lips, chin | Video capture review by researcher | √ | | |
| | Hands | Accelerometer band put over hand/wrist. Capture of video also. | | | |
| | Feet | Accelerometer band put over foot arch and ankle. Capture of video also. | | | |
| 21 | Action Tremor | Accelerometer band put over hand and arm. Capture of video also. | √ | | |
| 22 | Rigidity Upper Extremity | Force feedback armature; video capture | | √ | |
| | Lower Extremity | Force feedback leg lift armature Questionnaire | | | √ |
| 23 | Finger Taps | Adapted computer mouse; Video capture | | √ | |

FIGURE 8B

IMPLEMENTATION OF UNIFIED PARKINSON'S DISEASE RATING SCALE

| No | Test Target | Description | Basic | Complex | Comprehensive |
|---|---|---|---|---|---|
| 24 | Hand Grips | Handheld dynamometer; video capture | | ✓ | |
| 25 | Hand Pronate / Supinate | Hand strap accelerometer, worn around palm | ✓ | | |
| 26 | Leg Agility | Tested using pressure sensitive walking pad and built in gauge to show patient minimum height to raise leg | | ✓ | |
| 27 | Arise from chair | Video to be later analyzed by a professional | | ✓ | |
| 28 | Posture | Photos or videos to be later analyzed by a professional | | | ✓ |
| 29 | Gait | A commercial solution is available using a walking pad and sensors inserted into patient's shoes; video taping of test for later analysis by researcher | | | ✓ |
| 30 | Postural Stability | Shoulder accelerometer; video capture | | ✓ | |
| 31 | Body bradykinesia | Patient performs "walk to" tasks using walking pad and shoe sensors; concurrent video taping; timed video of patient's face for subsequent count of blinking in a unit time | | | ✓ |
| 32 | Dyskinesia (duration) | Questionnaire | ✓ | | |
| 33 | Dyskinesia (disability) | Questionnaire | | ✓ | |
| 34 | Dyskinesia (pain) | Questionnaire | | ✓ | |
| 35 | Early morning dystonia | Questionnaire | | ✓ | |
| 36 | "Offs" (predictable) | Questionnaire | | | ✓ |
| 37 | "Offs" (unpredictable) | Questionnaire | | | ✓ |

FIGURE 8C

IMPLEMENTATION OF UNIFIED PARKINSON'S DISEASE RATING SCALE

| No | Test Target | Description | Level of Use | | |
|---|---|---|---|---|---|
| | | | Basic | Complex | Comprehensive |
| 38 | "Offs" (Sudden) | Questionnaire | | | ✓ |
| 39 | "Offs" (duration) | Questionnaire | | | ✓ |
| 40 | Anorexia, nausea, vomiting | Questionnaire | ✓ | | |
| 41 | Sleep disturbance, insomnia, hypersmnolence | Questionnaire | ✓ | | |
| 42 | Symptomatic orthostasis | Blood pressure monitor while rising from chair (as in #27) | | | ✓ |
| | Blood pressure seated | Blood pressure monitor | | | |
| | Blood pressure supine | Blood pressure monitor | | | |
| | Blood pressure standing | Blood pressure monitor | | | |
| | Weight | Scale | | | |
| | Pulse seated | Blood pressure monitor | | | |
| | Pulse standing | Blood pressure monitor | | | |

FIGURE 8D

PRIMARY OUTCOME MEASURES FOR FIRST CUREPARK™ IMPLEMENTATION (BASIC)

| Category | Measure |
|---|---|
| Mentation | Touch screen Questionnaire; short term memory shapes, words, colors. |
| Depression | Touch screen Questionnaire |
| Motivation/Initiative | Touch screen Questionnaire |
| Speech | Live Voice capture for later physician analysis (repeat standard phrases, on screen prompt). Constant distance. |
| Swallowing | Touch screen Questionnaire |
| Dressing | Touch screen Questionnaire |
| Turning in bed | Touch screen Questionnaire |
| Falling | Touch screen Questionnaire |
| Freezing | Touch screen Questionnaire |

FIGURE 8e

| Tremor (at rest, hand, forearm) | Upper extremity accelerometer |
|---|---|
| Speech | Voice capture for later physician analysis (repeat standard phrases; on screen prompt) Constant distance. |
| Tremor at rest Face, lips, chin | Video capture review by researcher |
| Action Tremor | Accelerometer band put over hand and arm. Capture of video also. |
| Hand Pronate / Supinate | Hand strap accelerometer, worn around palm |
| Dyskinesia (duration) | Touch screen Questionnaire |
| Anorexia, nausea, vomiting | Touch screen Questionnaire |
| Sleep disturbance, insomnia, hypersomolence | Touch screen Questionnaire |

FIGURE 8f

Endpoints:

1) Successful remote data to be captured through the CurePark(TM)™ system, as measured by completion of all test tasks.

2) Demonstrating a significant, positive correlation between remote administration of the basic section of the UPDRS as described above both in the physician's office and an assessment arrived based on data collected using the CurePark(TM)™ system remotely. Scores should reflect a statistical correlation.

Protocol Summary

| | |
|---|---|
| Title: | Feasibility of the CurePark(TM) web based- assessment tool for the determination of baseline staging, data gathering and monitoring of early, middle, and late stage PD. |
| Clinical Phase: | Pilot Study |
| Sponsor: | Curemark |
| PI: | |
| Conducted by: | Multi-site (2-3) academic medical centers. |
| Sample Size: | N= 30<br>10 early, 10 middle and 10 late stage PD as determined on the Hoehn and Yahr staging scale. |
| Study Population: | Individuals between the ages of 30-60 years previously diagnosed with early, middle or late stage PD. |
| Accrual Period: | 12-18 months |
| Study Design: | A longitudinal prospective case-controlled study of 30 patients over 6 months. |
| Study Duration: | 6 months |
| Objectives: | The objectives of this clinical testing are to (1) To verify that the data obtained with the CurePark(TM) system allows a physician/researcher to reach the same patient assessments as can be obtained using an on-site test using the same portion of the UDPRS; (2) Verify that a PD patient can operate and interact with the CurePark(TM) system successfully as determined by completion of the testing, and that they find the interaction user friendly as determined by a survey questionnaire of the patients at the end of the project. |
| Methods: | This first implementation of the CurePark(TM) system incorporates a subset of the UDPRS designed to demonstrate the capture of motor as well as non-motor information and to show the feasibility of integrating various technologies and software to function in remote testing. Administration of the questions will |

FIGURE 9b employ data capture and storage solution including various plug-ins including an in-screen video capture and microphone for viewing the patient real-time and recorded voice data which will be standard to the CurePark(TM)™ device. Accelerometers will also be utilized to capture digital information on rest tremor in addition to video data for later analysis by the physician. Touch screen questionnaires will also be used as well as voice capture technology. This ability to provide digital information on some tests a test in addition to information traditionally captured and ranked using visual analysis has been intentionally included so as to provide new sources of information as well as a basis for developing a more objective basis for evaluations arrived at using the PUPDRS. Data will be relayed using web enabled data transfer and database storage methodology stored into a The Basic Test Module will provide the clinician and researcher a decisions regarding medications or treatment approaches. It consists of a number of relatively simple tests that can be performed as many times as necessary either daily or multi-times per day. The test gathers the data in both objective and subjective form as it relates to the UPDRS #'s 1, 3, 4, 5, 7, 10, 12, 13, 14, 15, 16, 18, 20, 21, 22, 25, 32, 34, 40 and 41, (representing a total of 20 tests).

In future implementations of the CurePark(TM) device additional sets of tests will be added. Complex tests, for future implementation, will allow the clinician and researcher to more closely examine a greater set of symptom parameters using more sophisticated technologies. The Complex Test Module includes UPDRS tests from the Basic Test Module along with those that correspond to the UPDRS #'s 6, 8, 17, 19, 22, 23, 26, 27, 33 and 35 (for a total of 30 tests).

The Comprehensive test, also for future implementation, incorporates all levels of the UPDRS including those of the Basic and Complex Test Modules along with those from the UPDRS corresponding to #'s 2, 9, 11, 28, 29, 30, 31, 35, 36, 37, 38, 42 (a total of 42 tests). The Comprehensive test, can be utilized for a remote baseline examination or an examination of one complete specific area of the body.

Study Description:

A longitudinal prospective study case controlled study of 30 patients over 6 months will be conducted. Patients will be selected who have previously been rated as stage 1 or 2 (early), 3 (middle), or 4/5 (late) stage disease on the Hoehm and Yahr staging scale. Ten (10) patients from each group will be selected for a total of 30 patients. Baseline UPDRS will be done in person for each patient followed by the use of the CurePark™. Two individuals, skilled in the FIGURE 9c administration and interpretation of the UPDRS will be selected from a group of investigators previously shown to have consistent and well correlated test interpretations. The traditional approach test administration of the basic questions selected from the UPDRS will be administered and rated by one investigator while a second and separate investigator will be used to evaluate the data obtained by the CurePark™ system. This is to prevent prior experience ratings bias by the individual scoring the two tests. The study will require 3 visits where the same basic section of the UPDRS will be administered to the patient. Following rating of the tests, the evaluations will be statistically analyzed using

Inclusion Criteria:

1) Male or females with previously diagnosed PD.

2) Patients must be willing to make three visits to the study site.

3) Patient must demonstrate an understanding of how to utilize the CurePark™ assessment tool following standardized in office instruction..

4) Patients must possess a minimum of task performing ability such as the ability to read a computer screen, press a button, put on an elastic wrist band (containing an accelerometer for tremor measurement), and sit in a chair.

Exclusion Criteria:

1) Ages under 30 or over 60 years of age.

2) patient that have a co-morbid neurologic or psychiatric disorder.

3) Patients who have another movement disorder.

4) Patients who have an inability to or unwillingness to utilize a computer or web-based capture mode.

5) Patient has an inability to perform tasks ( such as sit, read, put on wrist band, press buttons) or presence of dementia sufficient to impair understanding what is required in the UPDRS.

Outcome Measures:

We have selected the Basic Test module from the CurePark™ test suite for initial validation. In selecting the Basic Test module we feel that we have identified a group of UPDRS elements that will be most helpful to the clinician researcher in assessing the present status of PD, as well as to give an overall baseline assessment that can be repeated one or more times a day should the PD researcher desire to examine the PD patient with and without medication.

Once these basic elements are validated, other elements of the CurePark™ test suite can be validated. Since the CurePark™ data collection includes objective measures as well as subjective assessments, clinical correlation to the UPDRS must also be validated. For example in addition to the visual data capture that the PD researcher/clinician will have access to, objective measures of tremor: amplitude, direction and frequency will be collected graphically over a specified time period.

This will allow for researchers to investigate new relationships between symptoms and their changes under various conditions as well as to add a new dimension of digital precision not available previously.

FIGURE 9d

SYSTEMS AND METHODS EMPLOYING REMOTE DATA GATHERING AND MONITORING FOR DIAGNOSING, STAGING, AND TREATMENT OF PARKINSONS DISEASE, MOVEMENT AND NEUROLOGICAL DISORDERS, AND CHRONIC PAIN

RELATED U.S. APPLICATION DATA

This application claims the benefit of U.S. Provisional Patent Application No. 61/086,136 filed on Aug. 4, 2008, which is incorporated by reference herein in its entirety.

TECHNICAL FIELD

This disclosure relates to early diagnosis, staging, assessment and treatment tools for Parkinson's disease (PD), movement disorders, neurological diseases, and/or chronic pain, designed to drive innovation and to best accelerate research into Parkinson's disease, movement disorders, neurological diseases, and/or chronic pain. The present disclosure facilitates improved access to patients suffering from such disorders along with innovative data capture methods designed to lead to improved therapies and assist in finding a cure for these disorders. The present disclosure is broadly applicable as a diagnosis and assessment tool for Parkinson's disease, movement disorders and many neurological diseases and chronic pain.

BACKGROUND

Parkinson's disease (PD) is a chronic and progressive degenerative disease of the brain that impairs motor control, speech, and other functions. The disease is named after English physician James Parkinson, who gave a detailed description of it in an 1817 work titled, "An Essay on the Shaking Palsy".

Parkinson's disease belongs to a group of conditions called movement disorders. It is characterized by muscle rigidity, resting tremor (typically at about 5 Hz), slowing of movement (bradykinesia) and, in extreme cases, nearly complete loss of movement (akinesia). Secondary symptoms may include high level cognitive dysfunction, subtle language problems, and depression.

In contrast to many other neurological disorders, the nature of the brain degeneration that produces Parkinson's disease has been well understood for decades. The symptoms are caused by loss of nerve cells that secrete dopamine in a tiny midbrain area called the substantia nigra. These nerve cells, for reasons that are not fully understood, are especially vulnerable to damage of various sorts, including drugs, disease, and head trauma. The term Parkinsonism is used for any process that destroys large numbers of these cells and thereby causes the same characteristic symptoms. Parkinson's disease, or more fully, idiopathic Parkinson's disease, is diagnosed when no specific physical cause for the loss of dopamine cells can be identified. This is the most common situation.

The term Parkinsonism is used for symptoms of tremor, stiffness, and slowing of movement caused by loss of dopamine cells in the substantia nigra. "Parkinson's disease" is the synonym of "primary Parkinsonism", i.e. isolated Parkinsonism due to a neurodegenerative process without any secondary systemic cause. In some cases, it would be inaccurate to say that the cause is "unknown" because a small proportion is caused by identifiable genetic mutations.

It is possible for a patient to be initially diagnosed with Parkinson's disease but then to develop additional features requiring revision of the diagnosis.

There are other disorders called Parkinson-plus diseases. These include: multiple system atrophy (MSA), progressive supranuclear palsy (PSP), corticobasal degeneration (CBD), and dementia with Lewy bodies (DLB). Lewy bodies are abnormal aggregates of protein that develop inside nerve cells. Most idiopathic Parkinson's disease patients also have Lewy bodies in their brain tissue, but the distribution is denser and more widespread in DLB. Even so, the relationship between Parkinson's disease, Parkinson's disease with dementia, and dementia with Lewy bodies (DLB) might be most accurately conceptualized as a spectrum, with a discrete area of overlap between each of the three disorders. The natural history and role of Lewy bodies is little understood.

These Parkinson-plus diseases may progress more quickly than typical idiopathic Parkinson disease. If cognitive dysfunction occurs before or very early in the course of the movement disorder then DLB may be suspected. Early postural instability with minimal tremor especially in the context of ophthalmoparesis should suggest PSP. Early autonomic dysfunction including erectile dysfunction and syncope may suggest MSA. The presence of extreme asymmetry with patchy cortical cognitive defects such as dysphasia and apraxias especially with "alien limb" phenomena should suggest CBD.

The usual anti-Parkinson's medications are typically either less effective or not effective at all in controlling symptoms; patients may be exquisitely sensitive to neuroleptic medications like haloperidol. Additionally, the cholinesterase inhibiting medications have shown preliminary efficacy in treating the cognitive, psychiatric, and behavioral aspects of the disease, so correct differential diagnosis is important.

Essential tremor may be mistaken for Parkinson's disease but lacks all other features besides tremor, and has particular characteristics distinguishing it from Parkinson's, such as improvement with beta blockers and alcoholic beverages (see http://en.wikipedia.org/wiki/Parkinson's_disease—cite_note-Jankovic2008-0). Wilson's disease (hereditary copper accumulation) may present with Parkinsonian features; young patients presenting with Parkinsonism or any other movement disorder are frequently screened for this rare condition, because it may respond to medical treatment. Typical tests are liver function, slit lamp examination for Kayser-Fleischer rings, and serum ceruloplasmin levels.

Parkinson's disease affects movement (motor symptoms). Other typical symptoms include disorders of mood, behavior, thinking, and sensation (non-motor symptoms). Patients' individual symptoms may be quite dissimilar and progression of the disease is also distinctly individual.

The cardinal symptoms of Parkinson's disease are:
Tremor: normally 4-6 Hz tremor, maximal when the limb is at rest, and decreased with voluntary movement. It is typically unilateral at onset. This is the most apparent and well-known symptom though an estimated 30% of patients have little perceptible tremor; these are classified as akinetic-rigid.
Rigidity: stiffness; increased muscle tone. In combination with a resting tremor, this produces a ratchety, "cogwheel" rigidity when the limb is passively moved.
Akinesia/bradykinesia: absence of movement and slowness, respectively. Rapid, repetitive movements produce a dysrhythmic and decremental loss of amplitude.

Postural instability: failure of postural reflexes, which leads to impaired balance and falls.

Other motor symptoms include gait and posture disturbances:

Shuffling: gait is characterized by short steps with feet barely leaving the ground, producing an audible shuffling noise. Small obstacles tend to cause the patient to trip.

Decreased arm-swing.

Turning "en bloc": rather than the usual twisting of the neck and trunk and pivoting on the toes, Parkinson's disease patients keep their neck and trunk rigid, requiring multiple small steps to accomplish a turn.

Stooped, forward-flexed posture: In severe forms, the head and upper shoulders may be bent at a right angle relative to the trunk (camptocormia).

Festination: a combination of stooped posture, imbalance, and short steps. It leads to a gait that gets progressively faster and faster, often ending in a fall.

Gait freezing: "freezing" is a manifestation of akinesia (an inability to move). Gait freezing is characterized by an inability to move the feet which may worsen in tight, cluttered spaces or when attempting to initiate gait.

Dystonia (in about 20% of cases): abnormal, sustained, painful twisting muscle contractions, often affecting the foot and ankle (mainly toe flexion and foot inversion), which often interferes with gait.

Speech and swallowing disturbances:

Hypophonia: soft speech. Speech quality tends to be soft, hoarse, and monotonous. Some people with Parkinson's disease claim that their tongue is "heavy" or have cluttered speech.

Monotonic speech.

Festinating speech: excessively rapid, soft, poorly-intelligible speech.

Drooling: most likely caused by a weak, infrequent swallow and stooped posture.

Dysphagia: impaired ability to swallow; may lead to aspiration pneumonia.

Other motor symptoms:

Fatigue (up to 50% of cases).

Masked faces (a mask-like face also known as hypomimia), with infrequent blinking.

Difficulty rolling in bed or rising from a seated position.

Micrographia (small, cramped handwriting).

Impaired fine motor dexterity and motor coordination.

Impaired gross motor coordination.

Akathisia: the inability to sit still.

Parkinson's disease causes cognitive and mood disturbances, being in many cases related. Estimated prevalence rates of depression vary widely according to the population sampled and methodology used. Reviews of depression estimate its occurrence in anywhere from 20-80% of cases. Estimates from community samples tend to find lower rates than from specialist centres. Most studies use self-report questionnaires such as the Beck Depression Inventory, which may overinflate scores due to physical symptoms. Studies using diagnostic interviews by trained psychiatrists also report lower rates of depression. More generally, there is an increased risk for any individual with depression to develop Parkinson's disease at a later date. Seventy percent of individuals with Parkinson's disease diagnosed with pre-existing depression go on to develop anxiety. Ninety percent of Parkinson's disease patients with pre-existing anxiety subsequently develop depression, apathy or abulia.

Cognitive disturbances include:

Slowed reaction time: both voluntary and involuntary motor responses are significantly slowed.

Executive dysfunction, characterized by difficulties in: differential allocation of attention, impulse control, set shifting, prioritizing, evaluating the salience of ambient data, interpreting social cues, and subjective time awareness. This complex is present to some degree in most Parkinson's patients; it may progress to:

Dementia: a later development in approximately 20-40% of all patients, typically starting with slowing of thought and progressing to difficulties with abstract thought, memory, and behavioral regulation. Hallucinations, delusions and paranoia may develop.

Short term memory loss: procedural memory is more impaired than declarative memory. Prompting elicits improved recall.

Non-motor causes of speech/language disturbance in both expressive and receptive language: these include decreased verbal fluency and cognitive disturbance especially related to comprehension of emotional content of speech and of facial expression.

Difficulty deceiving others that links to prefrontal hypometabolism.

Medication effects: some of the above cognitive disturbances are improved by dopaminergic medications, while others are actually worsened.

Movement disorders are neurological conditions that affect the speed, fluency, quality, and ease of movement. Abnormal fluency or speed of movement (dyskinesia) may involve excessive or involuntary movement (hyperkinesia) or slowed or absent voluntary movement (hypokinesia).

Movement disorders include the following conditions:

Ataxia (lack of coordination, often producing jerky movements)

Dystonia (causes involuntary movement and prolonged muscle contraction)

Huntington's disease (also called chronic progressive chorea)

Multiple system atrophies (e.g., Shy-Drager syndrome)

Myoclonus (rapid, brief, irregular movement)

Parkinson's disease

Progressive supranuclear palsy (rare disorder that affects purposeful movement)

Restless leg syndrome (RSD) and periodic limb movement disorders (PLMD)

Tics (involuntary muscle contractions)

Tourette's syndrome

Tremor (e.g., essential tremor, resting tremor)

Wilson disease (inherited disorder that causes neurological and psychiatric symptoms and liver disease).

Common dystonias include spasmodic torticollis, which affects muscles of the head, face, and neck; and blepharospasm, which causes involuntary closing of the eyelids.

Tourette's syndrome is an inherited disorder characterized by multiple motor and vocal tics (repeated muscle contractions). Symptoms of Tourette's syndrome usually develop during childhood or early adolescence. Patients with the disorder often develop behavioral problems such as hyperactivity, inattention, impulsivity, obsessions, and compulsions. In most cases, symptoms vary in frequency and in severity.

Tics are involuntary muscle contractions that interrupt normal activities. They often are preceded by a strong sensation or urge that is temporarily relieved following the muscle contraction. Examples of common tics include the following: blinking, clearing the throat, facial twitching, grunting, shrugging the shoulders, and sighing.

Movement disorders occur as a result of damage or disease in a region located at the base of the brain (basal ganglia). The basal ganglia are comprised of clusters of nerve cells (neurons) that send and receive electrical signals and are responsible for involuntary movement. Movement disorders may result from at least one of the following: age-related changes, environmental toxins, genetic disorders (e.g., Huntington's disease, Wilson disease), medications (e.g., antipsychotic drugs), metabolic disorders (e.g., hyperthyroidism), Parkinson's disease, and stroke.

Neurologic Diseases are disorders of the brain, spinal cord and nerves throughout the body. Together they control all the workings of the body. When something goes wrong with a part of the nervous system, an individual may have trouble moving, speaking, swallowing, breathing or learning. The individual may also have problems with memory, senses or mood.

Currently there are more than 600 neurologic diseases. Thus, neurological disorders are disorders that can affect the central nervous system (brain and spinal cord), the peripheral nervous system, or the autonomic nervous system. Major conditions include:

behavioral/cognitive syndromes
headache disorders such as migraine, cluster headache and tension headache
epilepsy
traumatic brain injury
neurodegenerative disorders, including Alzheimer's disease, Parkinson's disease, Huntington's disease, and amyotrophic lateral sclerosis (Lou Gehrig's disease)
cerebrovascular disease, such as transient ischemic attack and stroke
sleep disorders
cerebral palsy
infections of the brain (encephalitis), brain meninges (meningitis), spinal cord (myelitis)
infections of the peripheral nervous system
neoplasms: tumors of the brain and its meninges (brain tumors); spinal cord tumors, tumors of the peripheral nerves (neuroma)
movement disorders, such as Parkinson's disease, Huntington's disease, hemiballismus, tic disorder, and Tourette's syndrome
demyelinating diseases of the central nervous system, such as multiple sclerosis, and of the peripheral nervous system, such as Guillain-Barré syndrome and chronic inflammatory demyelinating polyneuropathy (CIDP)
spinal cord disorders: tumors, infections, trauma, malformations (e.g., myelocele, meningomyelocele, tethered cord)
disorders of peripheral nerves, muscle (myopathy) and neuromuscular junctions
exciting injuries to the brain, spinal cord and peripheral nerves
altered mental higher status, encephalopathy, stupor and coma
speech and language disorders; functional symptoms, having no apparent physiological cause; and
paraneoplastic neurological syndromes.

Chronic Pain Overview: While acute pain is a normal sensation triggered in the nervous system to alert an individual to possible injury and the need to take care of the situation or issue, chronic pain is different. Chronic pain persists. Pain signals keep firing in the nervous system for weeks, months, even years. There may have been an initial mishap, e.g.: sprained back, serious infection, or there may be an ongoing cause of pain, e.g.: arthritis, cancer, ear infection, but some people suffer chronic pain in the absence of any past injury or evidence of body damage.

Many chronic pain conditions affect older adults. Common chronic pain complaints include headache, low back pain, cancer pain, arthritis pain, neurogenic pain (pain resulting from damage to the peripheral nerves or to the central nervous system itself), psychogenic pain (pain not due to past disease or injury or any visible sign of damage inside or outside the nervous system).

Medications, acupuncture, local electrical stimulation, and brain stimulation, as well as surgery, are some treatments for chronic pain. Some physicians use placebos, which in some cases has resulted in a lessening or elimination of pain. Psychotherapy, relaxation and medication therapies, biofeedback, and behavior modification may also be employed to treat chronic pain. Many people with chronic pain may be helped if they understand the causes of pain and the many and varied steps that can be taken to undo what chronic pain has instantiated.

SUMMARY

This disclosure is directed to systems and methods, including computer-implemented systems and methods, to facilitate one or more of the following: diagnosis of disease; baseline and progression of disease staging; data gathering (e.g., biochemical, physical, neurological, and cognitive data gathering), including remote data gathering; monitoring, including remote monitoring; and treatment of patients suffering from or suspected of suffering from one or more of Parkinson's disease (PD) movement disorders, neurological diseases, and chronic pain. More particularly, this disclosure is directed to web-based and Internet systems and methods for remote implementation of the same.

It is a goal of the present disclosure to provide systems and methods, including computer-implemented systems and methods, to facilitate one or more of the following: diagnosis of disease; baseline and progression of disease staging; data gathering (e.g., biochemical, physical, neurological, and cognitive data gathering), including remote data gathering; monitoring, including remote monitoring; and treatment of patients suffering from or suspected of suffering from one or more of Parkinson's disease (PD) movement disorders, neurological diseases, and chronic pain. It is an additional goal to provide web-based and Internet systems and methods for remote implementation of the same.

Another goal of the present disclosure is to provide systems and methods for providing remote data gathering, monitoring, baseline staging, and treatment of Parkinson's disease and, more particularly, to systems and methods utilizing a web based interface and communicating via the internet, a wide area network, a local area network, or any other remote communication method.

Another goal of the present disclosure is to provide systems and methods for providing remote data gathering, monitoring, baseline staging, and treatment of movement disorders and, more particularly, to systems and methods utilizing a web based interface and communicating via the internet, a wide area network, a local area network, and any other remote communication method. Movement disorders include akathisia sometimes referred to as acathisia, akinesia including akinetic mutism; coma; Angelman syndrome; ataxia including spinocerebella degredation; athetosis, bradykinesia; chorea including Sydenham's chorea and Huntington's disease; cerebral palsy; dystonia, blepharospasm; mogigraphia, sometimes referred to as writer's cramp; spasmodic torticollis; dyskinesias, including paroxysmal dyskinesias, paroxysmal kinesigenic dyskinesia, paroxysmal non-kinesigenic dyskinesia, paroxysmal exertion-induced dyskinesia, paroxysmal hypnogenic dyskinesia, and tardive dyskinesia; Fragile X-associated tremor; ataxia syndrome; geniospasm; Joubert syndrome; Machado-Joseph disease; multiple system atrophy; striatonigral degeneration; myoclonus; neuroacanthocytosis; neurodegeneration with brain iron accumulation; paroxysmal choreoathetosis disease; restless leg syndrome; spasm, including infantile spasm; stereotypic movement disorders; stereotypy; tic disorder; Tourette's syndrome; tremor; essential tremor; and Wilson's disease.

Another goal of the present disclosure is to provide systems and methods for providing remote data gathering, monitoring, baseline staging, and treatment of neurological diseases and, more particularly, to systems and methods utilizing a web based interface and communicating via the internet, a wide area network, a local area network, and any other remote communication method. Neurological diseases include Landau-Kleffner syndrome; acute disseminated encephalomyelitis; attention deficit hyperactivity disorder; Holmes-Adie syndrome; adrenoleukodystrophy; leukodystrophy; Pelizaeus-Merzbacher disease; metachromatic leukodystrophy; agenesis of the corpus callo sum; agnosia; Aicardi syndrome; neurological complications of AIDS; Alexander disease; Alpers' disease; alternating hemiplegia; amyotrophic lateral sclerosis; Von Hippel-Lindau disease; antiphospholipid syndrome; aphasia; apraxia; arachnoid cysts; arachnoiditis; chiari malformation; arteriovenous malformation; Asperger syndrome; autism and autism spectrum disorders; dysautonomia; back pain; Barth syndrome; Batten disease; myotonia; myotonia congenita; Behcet's disease; Bell's palsy; monomelic amyotrophy; meralgia paresthetica, Binswanger's disease; incontinentia pigmenti; brachial plexus injuries; orthostatic hypotension; brain and spinal tumors; tuberous sclerosis; cerebral aneurysm; traumatic brain injury; Brown-Sequard syndrome; Kennedy's disease; spinal muscular atrophy; cerebral autosomal dominant arteriopathy with sub-cortical infarcts and leukoencephalopathy; carpal tunnel syndrome; complex regional pain syndrome; cerebral cavernous malformation; spinal cord injury; central cord syndrome; central pain syndrome; central pontine myelinolysis; cephalic disorders; lipid storage diseases; Tay-Sachs disease; Niemann-Pick disease; Farber's disease; cerebellar degeneration; Wernicke-Korsakoff syndrome; Sotos syndrome; cerebral hypoxia; Charcot-Marie tooth disease; neuroacanthocytosis; chronic inflammatory demyelinating polyneuropathy; postural tachycardia syndrome; Coffin Lowry syndrome; cerebro-oculo-facio-skeletal syndrome; colpocephaly; Moebius syndrome; congenital myasthenia; congenital myopathy; corticobasal degeneration; vasculitis syndromes of the central and peripheral nervous systems; craniosynostosis; Creutzfeldt-Jakob disease; Cushing's syndrome; opsoclonus myoclonus; Dandy-Walker syndrome; subacute sclerosing panencephalitis; septo-optic dysplasia; dementia, including multi-infarct dementia, frontotemporal dementia, subcortical dementia, dementia with Lewy bodies; dentate cerebellar ataxia; dyssynergia cerebellaris; myoclonica; dermatomyositis; developmental dyspraxia; Devic's syndrome; neuromyelitis optica; diabetic neuropathy; diffuse sclerosis; Schlder's disease; Dravet syndrome; dysgraphia; dyslexia; early infantile epileptic encephalopathy; Ohtahara syndrome; encephalitis; meningitis; encephalopathy; Sturge-Weber syndrome; epilepsy; Todd's paralysis; Fahr's syndrome; familial periodic paralyses; febrile seizures; Miller Fisher syndrome; hypotonia; foot drop; Friedreich's ataxia; Gerstmann's syndrome; Gerstmann-Straussler-Scheinker disease; giant axonal neuropathy; Guillain-Barré syndrome; hemifacial spasm; hereditary neuropathies; hereditary spastic paraplegia; Refsum disease; tropical spastic paraparesis; hydrocephalus; hydromyelia; hypertonia; inclusion body myositis; infantile neuroaxonal dystrophy; inflammatory myopathies; Whipple's disease; Isaac's syndrome; Kearns-Sayre syndrome; Klippel-Trenaunay syndrome; Klüver-Bucy syndrome; Lambert-Eaton myasthenic; Wallenberg's syndrome; Leigh's disease; Lennox-Gastaut syndrome; Lesch-Nyhan syndrome; lipid proteinosis; lissencephaly; neurological sequelae of lupus; megalencephaly; Menkes disease; microcephaly; transient ischemic stroke; mitochondrial myopathies; motor neuron diseases; Moyamoya disease; multifocal motor neuropathy; multiple sclerosis; muscular dystrophy; myasthenia gravis; myopathy; thyronic myopathy; neuroleptic malignant syndrome; neuronal migration disorders; schizencephaly; neurosarcoidosis; neurotoxicity; paraneoplastic syndromes; stiff-person syndrome; Parry-Romberg syndrome; peripheral neuropathy; periventricular leukomalacia; porencephaly; post-polio syndrome; primary lateral sclerosis; tabes dorsalis; progressive multifocal leukoencephalopathy; Alpers' disease; progressive supranuclear palsy; Rasmussen's encephalitis; Rett syndrome; Sandhoff disease; shaken baby syndrome; sleep apnea; spasticity; spinal cord infarction; syncope; hydromyelia; tethered spinal cord syndrome; thoracic outlet syndrome; transverse myelitis; Troyer syndrome; and whiplash.

Another goal of the present disclosure is to provide systems and methods for providing remote data gathering, monitoring, baseline staging, and treatment of chronic pain and pain management and, more particularly, to systems and methods utilizing a web based interface and communicating via the internet, a wide area network, a local area network, and any other remote communication method.

Another goal of the present disclosure is to make life better for those with Parkinson's disease, movement disorders, neurological disease, and/or chronic pain by measuring the efficacy of various treatments to treat the disease or disorder, delay its onset, and/or prevent it from developing.

Another goal of the present disclosure is to make an early diagnosis of Parkinson's disease, movement disorders, and neurological disease, and/or chronic pain, which allows both the patient and caregivers time to make choices that maximize quality of life; select an appropriate medical team; afford a better chance of benefiting from treatment and/or participate in studies or experimental treatments which tend to focus on early stage Parkinson's disease, movement disorders, and/or neurological diseases; lessen anxieties about unknown problems; enhance safety and security by planning for diminished or impaired physical or mental capacity; and provide more time to plan for the future.

Yet another goal of the present disclosure is to remotely acquire fully validated clinical data and assessments of Parkinson's disease, movement disorders, neurological disease symptoms, and/or chronic pain patients from a greater population and cross-section of patients, at significantly lower cost with types and level of data previously unavailable to the physician or researcher, especially from a remote access location. Improved access to patients and innovative data capture will ultimately lead to improved therapies and render assistance in the search for therapies for Parkinson's disease, movement disorders, neurological diseases, and/or chronic pain.

Yet another goal of the present disclosure is to aid in differential diagnosis of Parkinson's disease, movement disorders, neurological diseases, and chronic pain from other disorders.

Yet another goal of the present disclosure is to detect memory loss of recently learned information, thereby enabling early detection of the onset of dementia related to Parkinson's disease, neurological diseases, movement disorders, and/or chronic pain.

Yet another goal of the present disclosure is to detect difficulty with performing everyday tasks such as playing simple games, dressing, cooking meals, or basic hygiene. Measuring the amount and type of difficulty with performing everyday tasks allows for discrimination between normal age related thought process degradation and Parkinson's symptoms or progression of other movement disorders, neurological diseases, and/or chronic pain. Periodic measurement of difficulty with performing everyday tasks will provide another metric for gauging the progression of the disease or disorder.

Yet another goal of the present disclosure is to detect difficulty with speech. Voice recognition will be utilized to detect the loss of memory for simple words or the use of unusual words in place of the correct word or words. By measuring the amount and type of difficulty with speech the present disclosure, one is able to discriminate between normal age related speech impairment and Parkinson's disease symptoms or other movement disorders, neurological diseases, and/or chronic pain. Periodic measurement of difficulty with speech will provide yet another metric for gauging the progression of the disease or disorder.

Yet another goal of the present disclosure is to detect difficulty with abstract thinking. One or more tests comprising a series of tasks are utilized to test abstract thinking skills which may be compared against a standard or known baseline. Periodic measurement of abstract thinking skills will provide yet another metric for gauging the progression of the disease or disorder.

Yet another goal of the present disclosure is to detect changes in personality and to distinguish this from normal changes in personality from an individual's age to symptoms related to Parkinson's disease, neurological disease, movement disorders, and/or chronic pain. Periodic measurement of personality, e.g.: by using standard assays or questionnaires, will provide yet another metric for gauging the progression of the disease or disorder.

Yet another goal of the present disclosure is to detect changes in mood or behavior which is another symptom of Parkinson's disease, other neurological diseases, movement disorders, and/or chronic pain and to distinguish this from normal changes in mood or behavior. Periodic measurement of mood or personality swings will provide yet another metric for gauging the progression of the disease or disorder.

Yet another goal of the present disclosure is to assess risk factors for developing Parkinson's disease, neurological diseases, movement disorders, and/or chronic pain, such as age, family history, genetics (both risk and deterministic genes), traumatic head injury, high blood pressure, heart disease, stroke, diabetes and high cholesterol, weight, tobacco and excess alcohol consumption, physical exercise, mental exercise, and social interactions.

Yet another goal of the present disclosure is to provide an easy to access, Health Insurance Portability and Accountability Act (HIPAA) compliant, fully comprehensive medical and psychological data and timelines for the primary care physician, neurologists, psychiatrists, and psychologists, and other authorized medical care professionals for the prophylactic treatment of Parkinson's disease, neurological diseases, movement disorders, and/or chronic pain.

Yet another goal of the present disclosure is to overcome the difficulties in recruitment of a sufficient number of Parkinson's disease, neurological disease, movement disorder, and/or chronic pain patients for clinical studies who fit acceptance criteria and expected patient compliance. By remotely collecting data in batch mode, real-time, or near real-time that would normally involve physician/patient interactions, affords a significant improvement in patient recruitment as well as the kinds and frequency of data collection possible in an investigation.

Yet another goal of the present disclosure is to remotely acquire improved and fully validated clinical data and assessments of Parkinson's disease, neurological disease, movement disorder, and/or chronic pain symptoms, from a broad population and cross-section of patients, at significantly lower cost. This data type and level of data has to date been unavailable to the physician or researcher, especially from a remote access location. This type of data capture will ultimately aid in transforming how certain types of clinical research is conducted. Improved access to patients and innovative data capture will ultimately lead to improved therapies and render assistance in the search for a cure for Parkinson's disease, neurological diseases, movement disorders, and/or chronic pain.

Another goal of the present disclosure is to overcome the traditional hurdles for the recruitment of a sufficient number of patients who fit acceptance criteria, along with patient compliance any clinical study, including those in Parkinson's disease, neurological disease, movement disorders, and/or chronic pain. In addition, the elimination or reduction in the quantity of on-site physician interactions and testing is a significant benefit of the present disclosure. Indeed, traditional on-site testing and interactions has been the only way in which Parkinson's disease patients have been assessed up until the present disclosure.

Another goal of the present disclosure is to overcome the lack of patient recruitment which can limit the amount and frequency of data collected, thereby restricting the full utility of the investigation. The ability to remotely collect data in real-time or near real-time that would normally involve physician/patient interactions will significantly improve patient recruitment as well as the kinds and frequency of data collection possible in an investigation. Assimilating and translating data under the present disclosure is designed for use by the physician or researcher and is potentially life altering for those with Parkinson's disease, neurological disease, movement disorders, and/or chronic pain, increasing the ability to diagnose and treat, assessing medication dosage and compliance, and longitudinally track the progression of Parkinson's disease, neurological disease, movement disorders, and/or chronic pain patient. This type of patient surveillance will ultimately serve to decrease morbidities associated with Parkinson's disease, neurological disease, movement disorders, and/or chronic pain, increase patient/physician contact, and will serve as an excellent research platform.

Yet another goal of the present disclosure is to assimilate and translate data remotely acquired by the present disclosure for use by the physician or researcher, will increase the ability to diagnose and treat, assessing medication dosage and compliance, and longitudinally track the progression of Parkinson's disease, neurological disease, movement disorders, and/or chronic pain patient. This type of patient surveillance will ultimately serve to decrease morbidities associated with many of these diseases and disorders, increase patient/physician contact, and will serve as an excellent research platform.

Yet another goal of the present disclosure is to provide an easily accessible "in-home" web based administration of mental status testing, including but not limited to the mini mental state examination and the "mini-cognitive" test that will allow frequent (diurnal, daily, weekly, monthly) monitoring of a patients mental state and automatically trigger warnings or alarms for patients that miss or fail their tests.

Yet another goal of the present disclosure is to provide an easily accessible "in-home" web based administration of the Unified Parkinson's Disease Rating Tests, in whole, in part, incrementally, and/or on a predefined schedule by the patient, health care provider, doctor, or clinical researcher.

Yet another goal of the present disclosure is to provide both standard and customizable tests tailored to a patient, group of patients, or clinical study that allows for the appropriate frequency, type, and duration of testing and inclusion of appropriate test elements. The customization can be performed by a health care provider, health professional, doctor, or clinical researcher as appropriate to the type and use of data required.

Yet another goal of the present disclosure is to remotely gather data with the aid on an online health care provider, health professional, doctor, or clinical researcher available through interactive audio, video text, graphics, or any other media used singly or in any combination. The interaction may be full duplex or half duplex.

Yet another goal of the present disclosure is to allow for testing that is fully self administered by the patient or health care provider, as well as providing a means to deploy "man-in-the-loop" tele-testing with real-time patient/physician interaction for special situations or increased functionality to provide maximum flexibility in the kinds of testing that can be utilized, all while preserving the autonomous remote location data collection capabilities of the system.

Yet another goal of the present disclosure is to provide systems and methods for providing remote data gathering, monitoring, baseline staging, and treatment of Parkinson's disease and, more particularly, to systems and methods utilizing a web based interface and communicating via the internet, a wide area network, a local area network, and any other remote communication method.

BRIEF DESCRIPTION OF THE DRAWINGS

The above and other goals and advantages of the present disclosure will be apparent upon consideration of the following detailed description, taken in conjunction with accompanying drawings, in which like reference characters refer to like parts throughout, and in which:

FIGS. 6a-e is a standard Unified Parkinson's disease Rating Scale.

FIGS. 7a-b is a standard Unified Parkinson's disease Rating Scale Data Form.

FIGS. 8a-g is a web implementation of the Unified Parkinson's Disease Rating Scale and associated level for use in remote data gathering, monitoring, baseline staging, and treatment of Parkinson's disease, neurological diseases, and other movement disorders, in accordance with another embodiment of the present disclosure.

FIGS. 9a-d is a representative Summary Protocol for feasibility of one embodiment of the present disclosure of a web based-assessment tool for the determination of baseline staging, data gathering and monitoring of early, middle, and late stage Parkinson's disease.

DESCRIPTION

Figure 1:
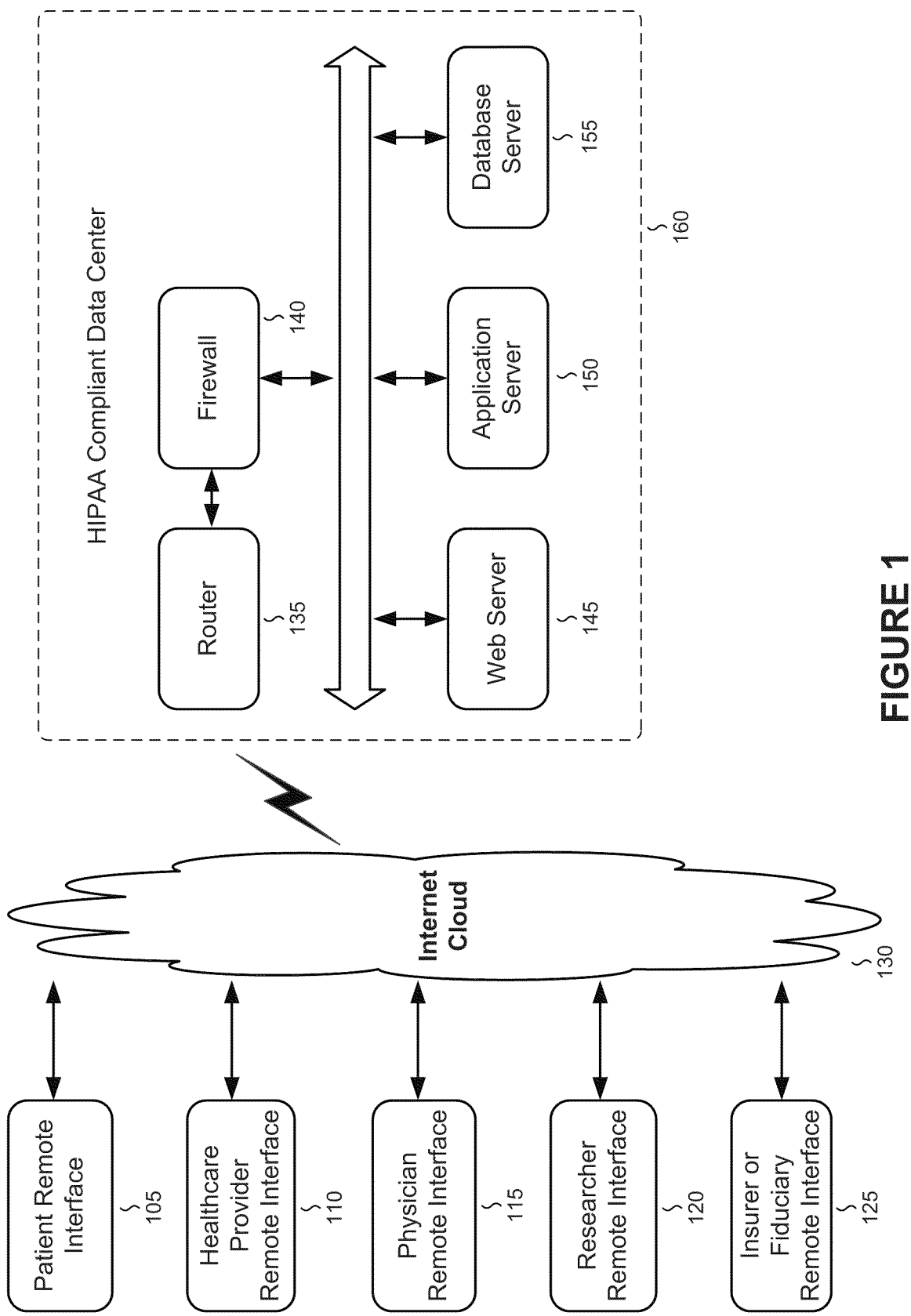
FIG. 1 is a block diagram of a system for remote data gathering, monitoring, baseline staging, and treatment of Parkinson's disease, neurological diseases, and/or other movement disorders, in accordance with one embodiment of the present disclosure.

The present disclosure is directed to systems and methods, including computer-based systems and methods for providing one or more remote data gathering, monitoring, diagnosis, baseline and progression of disease staging, and treatment methods for Parkinson's disease, neurological diseases, movement disorders, and/or chronic pain and, more particularly, to systems and methods utilizing a web based interface and communication via the internet, a wide area network, a local area network, or any other remote communication method.

In the following description, it is to be understood that system elements having equivalent or similar functionality are designated with the same reference numerals in the Figures. It is to be further understood that the present disclosure may be implemented in various forms of displays, hardware, software, firmware, networks or combinations thereof. In particular, the system modules described herein are preferably implemented in software as application programs that are executable by, e.g., a general purpose computer or any machine or device having any suitable and preferred microprocessor architecture.

Preferably, the present disclosure is implemented on computer platforms including hardware such as one or more central processing units (CPU), a random access memory (RAM), and input/output (I/O) interface(s). The computer platform may also include an operating system and microinstruction code. The various processes and functions described herein may be either part of the microinstruction code or application programs which are executed via the operating system. In addition, various other peripheral devices may be connected to one or more computer platforms, such as accelerometers; gyroscopes; magentometers; global positioning receivers and processing units; video cameras and video capture devices, such as web cameras, laser imaging radars, displays and touch input screens; speakers and other audio annunciators; microphones and other audio capture devices; capacitive contact pads and strain gauges; writing pads; touch pads; network interfaces and additional data storage devices; and printing devices.

It is to be further understood that, because some of the constituent system components described herein are preferably implemented as software modules, hardware devices, and network interconnections, the actual system connections shown in the Figures may differ depending upon the manner in which the systems are programmed or implemented. Given the teachings herein, one of ordinary skill in the related art will be able to contemplate these and similar implementations or configurations of the present disclosure.

Although illustrative embodiments have been described herein with reference to the accompanying drawings, it is to be understood that the present disclosure is not limited to those precise embodiments, and that various other changes and modifications may be affected therein by one skilled in the art without departing from the scope or spirit of the disclosure. All such changes and modifications are intended to be included within the scope of the disclosure as defined by the appended claims.

Referring now to FIG. 1, a block diagram illustrates a system for remote data gathering, monitoring, baseline staging, and treatment of Parkinson's disease, movement disorders, neurological diseases, and/or chronic pain comprised of a Remote Patient Interface 105, Health Care Provider Remote Interface 110, Physician Remote Interface 115, Researcher Remote Interface 120, and Insurer or Fiduciary Remote Interface 125, which are operatively connected to a Remote Data Center 160 via the Internet 130 or any other means of remote connection.

It should be noted that the Patient, Health Care Provider, Physician, Researcher, and Insurer or Fiduciary Remote Interfaces may transmit data to, or receive data from, the Remote Data Center by any form of data transmission or via storage media. Transmission systems include, but are not limited to wide area networks, local area networks, wireless networks, cellular telephone transmission, satellite transmission, personal area networks (Bluetooth®), telephone dial-up interfaces, analog signals or digital signals via copper wire, fiber optics, and wireless including all portions of the spectrum such as visible, infrared, ultraviolet, ultrasonic, and radio frequency. Transmission systems may also include the physical delivery of memory storage devices including memory sticks, and all other forms of non-volatile and quasi-non-volatile memory devices.

In addition, the Patient, Health Care Provider, Physician, Researcher, and Insurer or Fiduciary Remote Interfaces may transmit data to, or receive data from each other directly utilizing an appropriate of routing or addressing system via any form of data transmission. Advantageously, the information transmitted may be retained indefinitely or for some prescribed period of time by the transmitting and or receiving party for record keeping purposes and/or transmitted to the data center or another central repository of information for additional record keeping.

The remote patient interface 105 provides: a portal to the data center application server 150, performs one or more suites of tests as prescribed by the physician or healthcare provider, and securely transmits the results of the tests back to the application server 150. In one embodiment, open source PGP encryption to authenticate the identity of users and encrypt personal medical data so it cannot be stolen or duplicated by anyone else. In addition, encrypted digital signatures ensure that the data cannot be altered once it's electronically "signed". Alternate encryption and validation technologies such as coviant diplomat transaction manager or other commercially or available encryption packages may be utilized if so desired.

It should be noted that Remote Patient Interface transmitting patient information may be part of a broader multi-purpose computing or network device. For example, the Patient Remote Interface may be hosted on an iPhone®, smartphone or any other personal digital assistant (PDA) or mobile computing device, a laptop computer, a desktop computer, or any device with a user interface and program capability, such as a cable box with a remote control.

The Healthcare Provider Remote Interface 110, the Physician Remote Interface 115, the Researcher Remote Interface 120, and the Insurer or Fiduciary Remote Interface 125 each provide portals to the Data Center Application Server.

In one embodiment of the present disclosure, any computer or device with a web browser and internet access may function as a Healthcare Provider, or Insurer or Fiduciary Remote Interface.

The Physician Remote Interface 115 allows patients to be added and removed from the system along with management of passwords and access privileges. More significantly, Physician Remote Interface provides access to raw and processed data collected from patient tests and can provide various types of reports and graphs to be generated based upon a specific patient's tests results and test histories. In addition, a physician can order, prescribe, or construct any desired series of tests on a one time or periodic basis.

The Healthcare Provider Remote Interface 110 allows limited access to one or more patient's data predicated upon specified privileges. For example, the healthcare provider may only be able to see patient compliance with various tests and test schedules. In addition, it will allow the healthcare provider to administer the tests to one or more patients.

The Researcher Remote Interface 120 allows provides access to raw and processed data collected from patient tests and can provide various types of reports and graphs to be generated based upon a one or more patient tests result and test histories. In addition, a researcher can aggregate or download large quantities of data from multiple patients based upon specific profiles or selection criteria for conducting research into Parkinson's disease, neurological diseases, movement disorders, and/or chronic pain. The data may be accessed on an anonymous basis or by specific patient.

The Fiduciary or Insurer Remote Interface 125 provides for the ability to send or receive billing information, pay bills, or process insurance claims. Patient health information and test results may be restricted to tests performed and testing dates for HIPAA compliance.

The data center 160 is comprised of a means for receiving and transmitting appropriate data such as an interface to the internet 130, a means for selecting only data beneficially intended for the present disclosure such as a router 135, and optionally, one or more firewalls 140 or other devices for protection from malicious or inadvertent attacks. The data center 160 will authenticate system users and sessions (e.g.: patients, healthcare providers, physicians, researchers, fiduciaries and insurers), maintain system user profiles and user information via a web server 145 or software or hardware with equivalent functionality, administer tests via an application server 150 or software or hardware with equivalent functionality, and create a database of results from some or all patient tests via a database server 155 or software or hardware with equivalent functionality, and generate reports based upon tests or data collected on one or more patients via the application server 150. Advantageously, the data center 160 will provide for automated back-up and recovery.

Administration functions will also be available, including system maintenance, maintaining system access privileges, and collecting various types of system performance and billing/payment information.

Data center functions may be implemented in a wide variety of architectures including all functions on a single CPU running on a single operating system to complex distributed functionality in a large load balanced data center. In one embodiment of the present disclosure, the data center architecture consists of one or more of the following open source components including the Linux operating system, Apache web server, PHP scripting language, Code Igniter PHP framework, jQuery DHTML Library PostgreSQL database, and open source PGP encryption. The Linux operating system may be utilized to host the all of the applications needed to implement the data center. The data center system will be architected in a modular fashion allowing the various components to be run on a single computer or across multiple computers to provide rapid scalability.

In one embodiment of the present disclosure, all or part of the data gathering, monitoring, baseline staging, and treatment system advantageously employs a modular architecture for rapid prototyping, validation, and deployment. A scalable architecture and user platforms may rely on open source or and commercially available or proprietary software, hardware and development and maintenance tools. This facilitates the addition of new tests and enhanced technologies while expediting prototyping and deployment.

The web server 145 will serve web pages to users of the system including Patients 105, Healthcare Providers 110, Physicians 115, Researchers 120, Fiduciaries and Insurers 125 via their respective remote interfaces. Additionally, data obtained during patient tests maybe uploaded to the data center 160 via Firefox® or other web browser. The PHP scripting language in combination with the jQuery DHTML Library and the Code Igniter PHP framework will provide for interactive web pages that dynamically created utilizing information stored in the PostgreSQL database. For example, patients may see different homepages than doctors and researchers. Additionally, different patients may run through different sets of tests as prescribed. The PostgreSQL database will store at a minimum: the User Access Control List (ACL), Patient Profile, Patient Test Results, System Logging Information, Patient/Doctor Login Dates, Login IP Addresses, Logout Dates, Patient Profile Changes, and related information.

The present system may optionally incorporate Health Insurance Portability and Accountability Act (HIPAA) compliant data security for all applicable aspects of the system including data access, data mining, data transmission, and data storage. The modular architecture of the present disclosure will allow for easy upgrading to new standards in privacy as they become mandated or applicable.

Figure 2A:
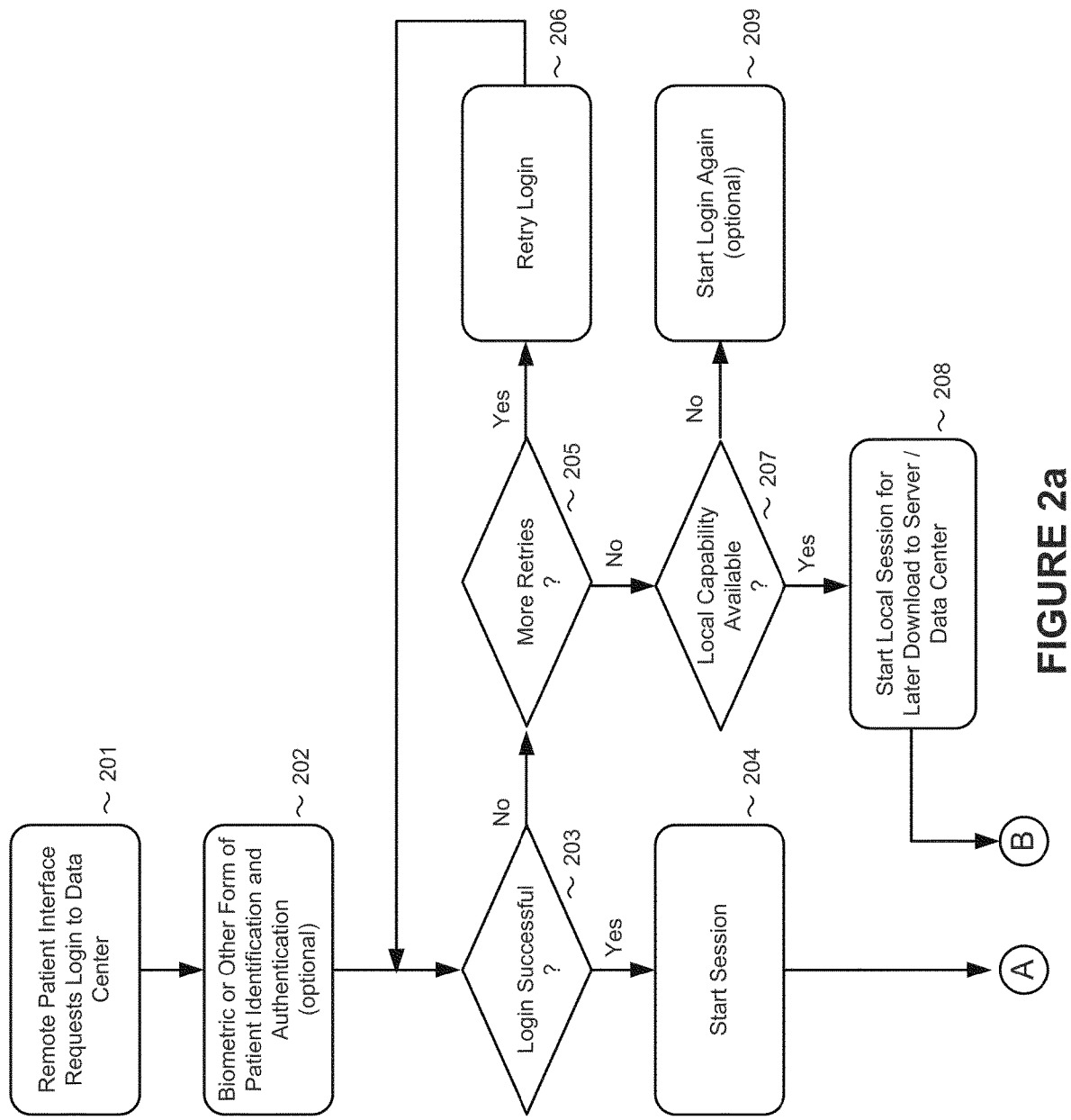
FIGS. 2a, 2b and 2c present a flow diagram of a system for remote data gathering, monitoring, baseline staging, and treatment of Parkinson's disease, neurological diseases, and other movement disorders, in accordance with another embodiment of the present disclosure.
Figure 2B:
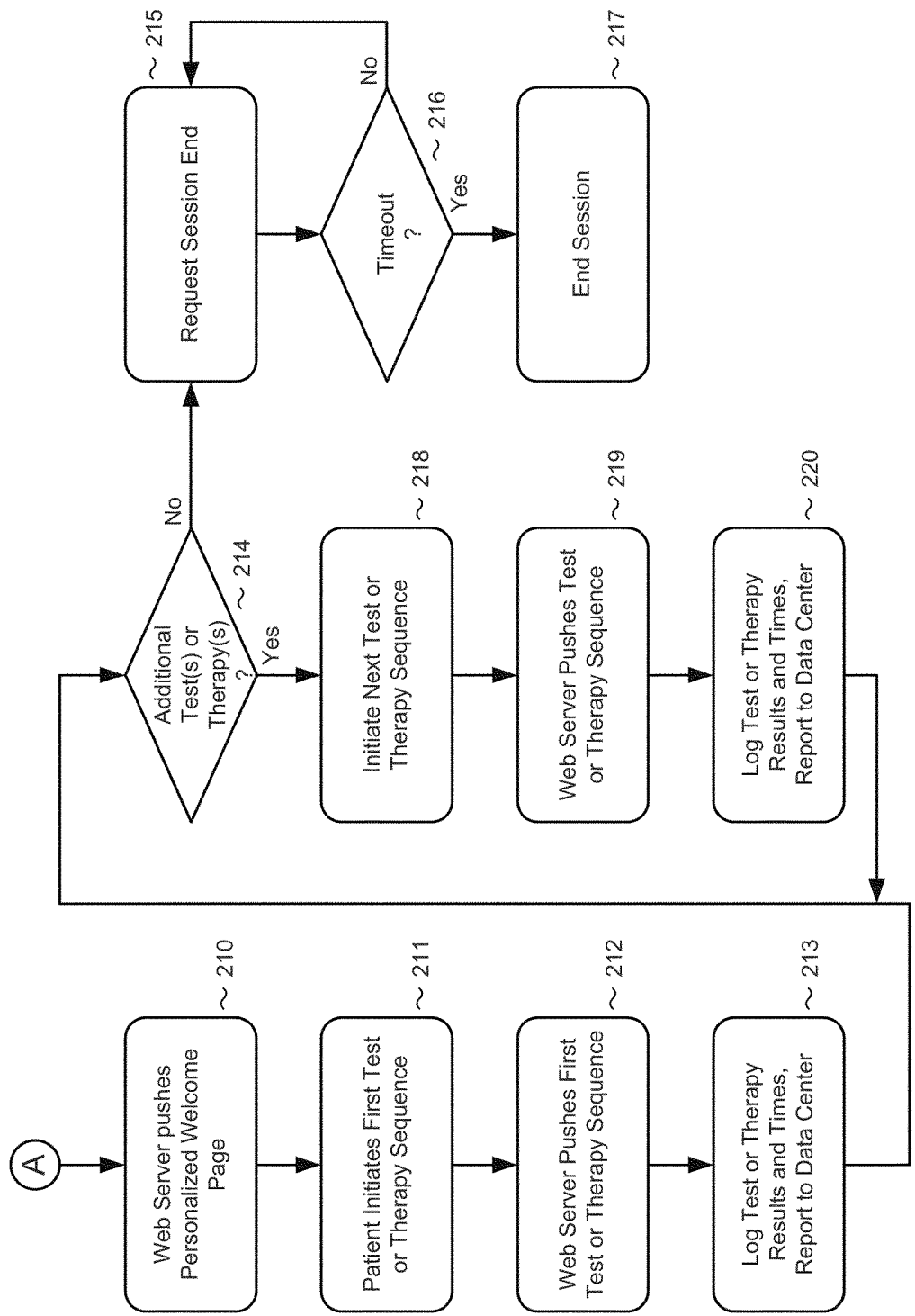
Figure 2C:
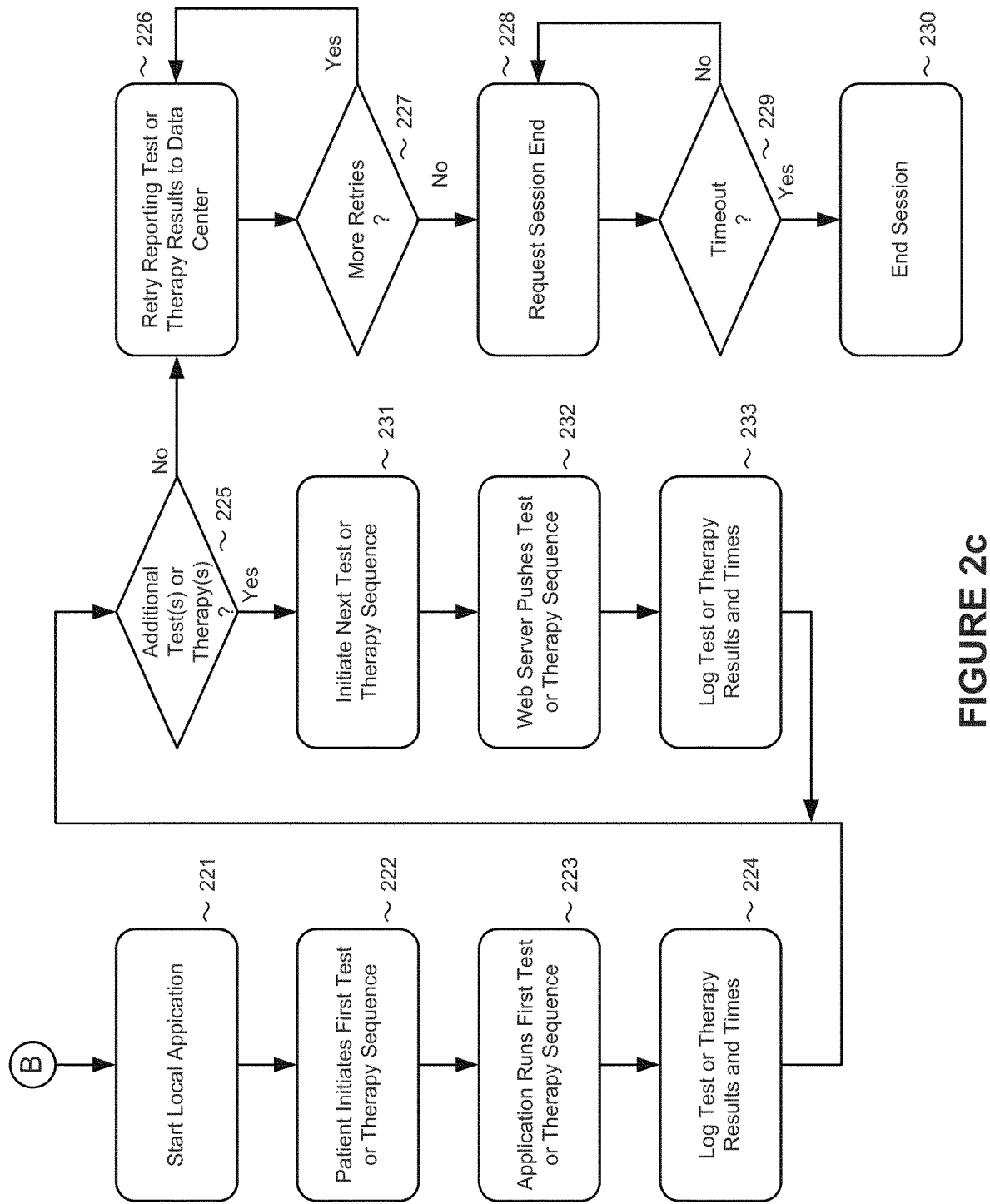

Referring now to FIGS. 2a, 2b, and 2c, a flow diagram illustrates a system for remote data gathering, monitoring, baseline staging, and treatment of Parkinson's disease, movement disorders, neurological diseases, and/or chronic pain in accordance with another embodiment of the present disclosure.

As shown in FIG. 2, a Remote Patient Interface 201 requests login to the data center. Biometric or any other form of Patient Identification 202 is optionally utilized for patient authentication. Other techniques, such as IP address and phone numbers, may also be utilized. If the login 203 is successful, the session is started 204. If the login is not successful, more retries may be attempted 205 and the login is retried 203. If no more retries are available 205, then a test is performed to see if the system can operate in local capacity 207. If local capability is available, then a local session is started for later download to the server or data center 208. If local capability is not available, then the login process can be optionally retried 209, 201.

If login is successful and a session is started 204, the web server pushes a welcome page 210, which is optionally personalized. The patient then initiates a first test sequence or therapy 211. The web server the pushes the first test or therapy sequence 212 to the patient interface. The test or therapy results and optionally times are reported back to the data center 213. A check is performed to see if there are any additional tests or therapies to be performed 214. If no additional tests or therapies are to be performed, then a session end is requested 215 and the session is ended 216. If additional tests or therapies are required 214, then the next test or therapy sequence is initiated 218. The web server then pushes the next test or therapy sequence 219 and the results are subsequently logged, optionally with times, and reported to the data center.

If login is not successful 203, then an optional test is performed to see of more retries are available 205. If more retries are available, then a login retry may be attempted 206. If more retries are not available, or if the patient wishes to operate in local mode only, a test is performed to see if local capability is available 207. If local capability is not available, then the only option available would be to restart the login process 209. If a local session is available 207, then a local session is started for later download to the server/data center 208.

If a local session is started 208, the local application that essentially performs the function of the web server and data logging in the local environment is then started 221. The local application 221 is optionally personalized. The patient then initiates a first test sequence or therapy 222. The application runs the first test or therapy sequence 223 to the patient interface. The test or therapy results, and optionally times, are logged for later reporting back to the data center 224. A check is performed to see if there are any additional tests or therapies to be performed 225. If no additional tests or therapies are to be performed, then a try is attempted to report the test or therapy results to the data center 226. Several retries may be attempted 227. If no more retries are available, the session is ended 228. If additional tests or therapies are required, then the next test or therapy sequence is initiated 231. The application then executes the next test or therapy sequence 232 and the results are subsequently logged, optionally with times 233, for later reporting to the data center.

It should be noted that it is not necessary that the Patient Remote Interface operate in an interactive web based mode. Indeed, the system could always work in the local environment and report results to the data center in batch mode.

Figure 3:
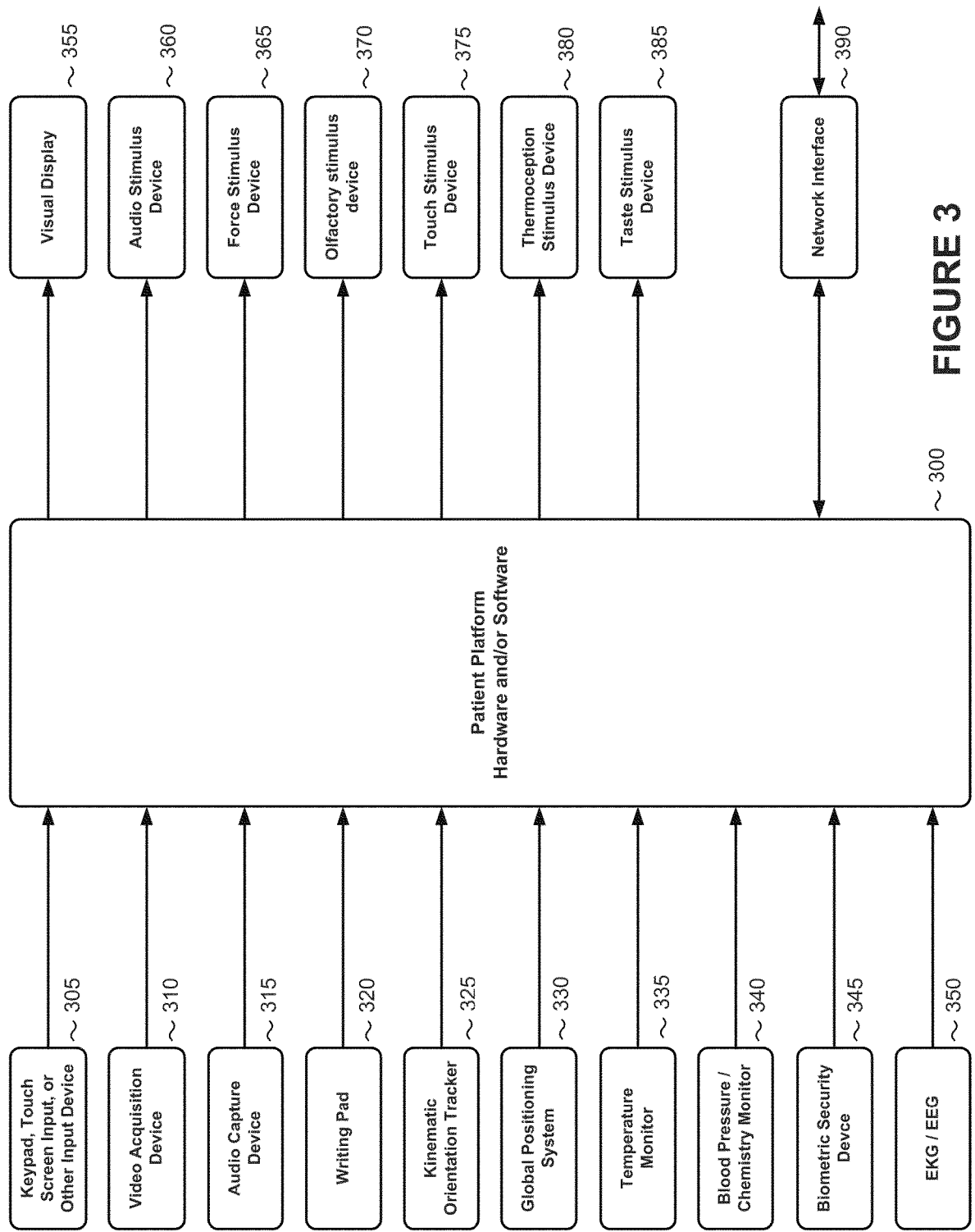
FIG. 3 is a block diagram of a Patient Remote Interface for remote data gathering, monitoring, baseline staging, and treatment of Parkinson's disease, neurological diseases, and other movement disorders, in accordance with yet another embodiment of the present disclosure.

Referring now to FIG. 3, a block diagram illustrates a Patient Remote Interface for remote data gathering, monitoring, baseline staging, and treatment of Parkinson's disease, neurological diseases, movement disorders, and/or chronic pain in accordance with yet another embodiment of the present disclosure. The Remote Patient Interface gathers data (e.g., biochemical, physical, neurological, cognitive data) via one or more means of interfacing and/or interacting with one or more patients and then transmits the acquired data in raw or processed form via any means to the data center or to one or more remote interfaces. Any known assay may be used to acquire the data gathered.

As shown the remote patient platform hardware/software device 300 interfaces with a variety of input and output devices. As shown, input devices for data acquisition from the patient may include one or more of the following: a keypad; touch screen input or other input device 305; a video acquisition device, such as a camera, webcam, or laser imaging radar 310; an audio capture device, such as a microphone, preamp, and analog to digital converter 315; a writing pad 320; a kinematic orientation tracker 325 which may be comprised of one or more gyroscopes, one or more accelerometers, a magnetometer, an optical motion/position sensing systems, a microwave motion/position sensing system, or any other mechanism, device, or stimulus sensing technology capable of sensing patient motion in any part of the patient's body. In one embodiment, a 3-axis gyro/accelerometer package, preferably with a wireless interface that acquires 3-axis attitude and acceleration information, along with pitch, roll, and yaw rates, may be utilized.

In addition, a global positioning system receiver 330 may be utilized to acquire patient location information or motion of the patient's location or any part of the body or appendage. The global positioning system may consist of one or more receivers along with various types of position augmentation devices, such as a wide area augmentation system or other form of position/motion sensing.

Temperature monitors 335 may be employed for sensing of either external or internal body temperatures. The sensing technology may be any means, including contact temperature sensors, including solid state sensors, infrared remote sensing, and temperature sensor systems, that employ active or passive scanning.

Blood pressure sensors and various forms of blood chemistry monitoring 340 may be employed, utilizing either invasive or non-invasive monitoring techniques.

Techniques utilized for blood pressure monitoring may rely on traditional cuff wraps or, more advantageously, pulse wave velocity which calculates blood pressure by measuring the pulse at two points along an artery. In addition, data from the kinematic orientation/motion sensor 325 may be employed concurrently with a pulse wave velocity blood pressure monitoring to compensate for blood pressure inaccuracies due to motion or orientation.

Electrocardiography (EKG/ECG) and/or electroencephalography (EEG) sensing 345 may be employed to gather data on cardiac and brain activity, respectively. A multitude of small portable EKG and EEG devices with USB or other data interfaces are widely available in the marketplace, A biometric or any other form of security device 350, such as a retinal scanner, voice recognition, electronic or mechanical lock and key, may be utilized for restricting access to one or more patients, care givers, doctors, clinicians, and/or other personnel.

In one embodiment of the present disclosure, the patient platform 300 may be a general purpose touchscreen computer running hosted on a Microsoft Windows Vista® operating system with the framework of the test application implemented using JavaScript® and will be hosted in a Mozilla Firefox® web browser. The JavaScript® code base will be stored and loaded from the data center's web server upon initiation of a test session by the patient. Microsoft Visual Studio C++® will be used to develop Windows® Services that will act as proxies for physical input devices. Windows® Services will be responsible for providing a robust and seamless interface to the JavaScript® application, while also handling initialization, error handling, and results reporting for their respective input devices. The JavaScript® application will communicate with the Windows® Services via a TCP/IP connection and SOAP (http://en.wikipedia.org/wiki/SOAP), an XML based communication protocol, with the data payload encrypted and authenticated by open source PGP encryption.

Output and stimulus devices include a visual display 355; an audio stimulus device 360, such as headphones or speaker system; one or more force stimulus devices 365 to test muscle strength, range of motion, and other physical properties; an olfactory stimulus device 370 for sense of smell; a touch stimulus device 375 for measuring nerve sensitivity and reflex responses; a thermoception stimulus device 380 for temperature perception testing; a taste stimulus device for taste sensitivity 385; and one or more network interfaces 390 which may be wired, wireless, cellular, infrared, microwave, or any other form of data transmission and reception, or any combination thereof.

Figure 4:
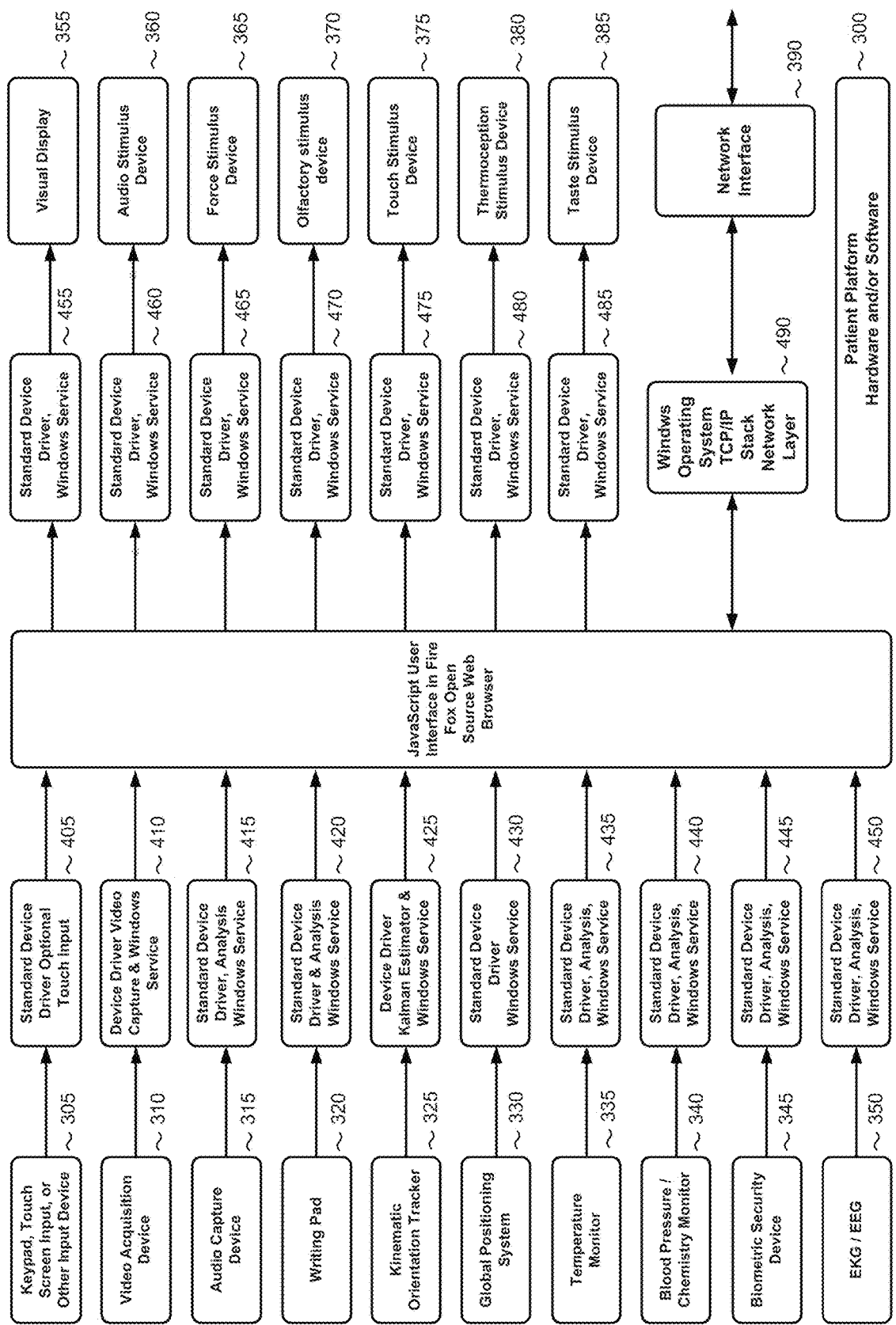
FIG. 4 is a block diagram of a Patient Remote Interface with interface drivers and web browser for remote data gathering, monitoring, baseline staging, and treatment of Parkinson's disease, neurological diseases, and other movement disorders, in accordance with yet another embodiment of the present disclosure.

FIG. 4 illustrates the interface drivers utilized to interface the various sensors and actuators in the Remote Patient Interface in one embodiment of the present disclosure. As shown, the patient platform 300 may be a general purpose touchscreen computer running hosted on a Microsoft Windows Vista® operating system with the framework of the test application implemented using JavaScript® hosted in a Mozilla Firefox® web browser. As shown, all sensor and stimulus devices may utilize standard device drivers, such as Windows® Services.

Depending upon system implementation and the desire to process data remotely, the drivers utilized may also be the previously recited standard drivers that are available from various commercial suppliers of the sensors and actuators/feedback devices or they may be fully custom drivers written to support specific sensor/feedback functions or data processing functions, or some combination thereof. In particular, high bandwidth output devices video acquisition 310, audio capture 315, and a kinematic orientation/motion tracker may have drivers or embedded applications that preprocess the data. By way of example, during a test for tremors on a limb, the data may be processed to give statistics on the frequency and magnitude of tremors rather than raw data from the gyros and accelerometers. The data processing functions may take place in the Device Driver Kalman Estimator and Windows® Service 425.

Figure 5A:
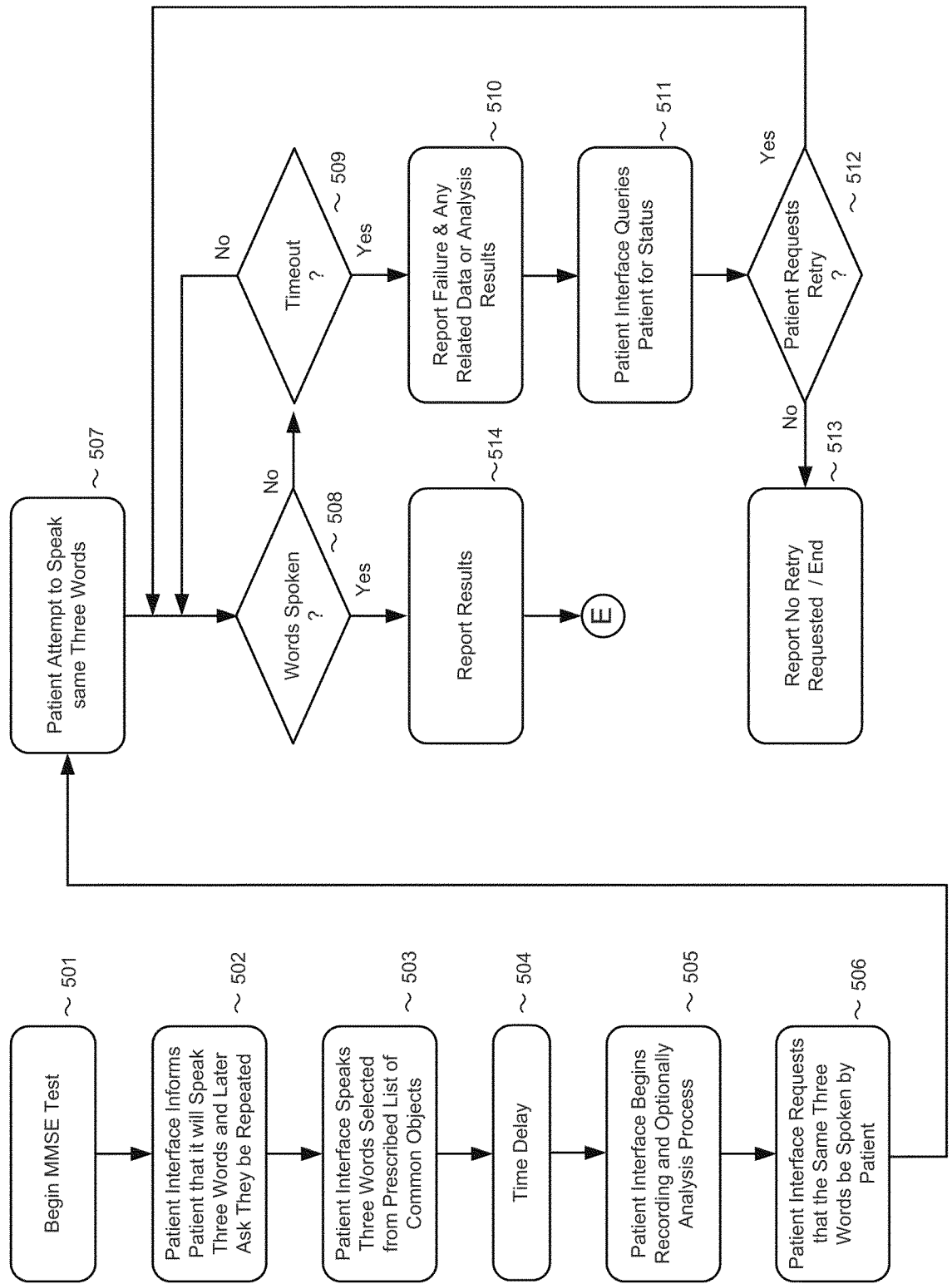
FIGS. 5a, 5b, 5c, 5d and 5e are a flow diagram of a Mini Mental State Examination for remote data gathering, monitoring, baseline staging, and treatment of Parkinson's disease, neurological diseases, and other movement disorders in accordance with another embodiment of the present disclosure.
Figure 5B:
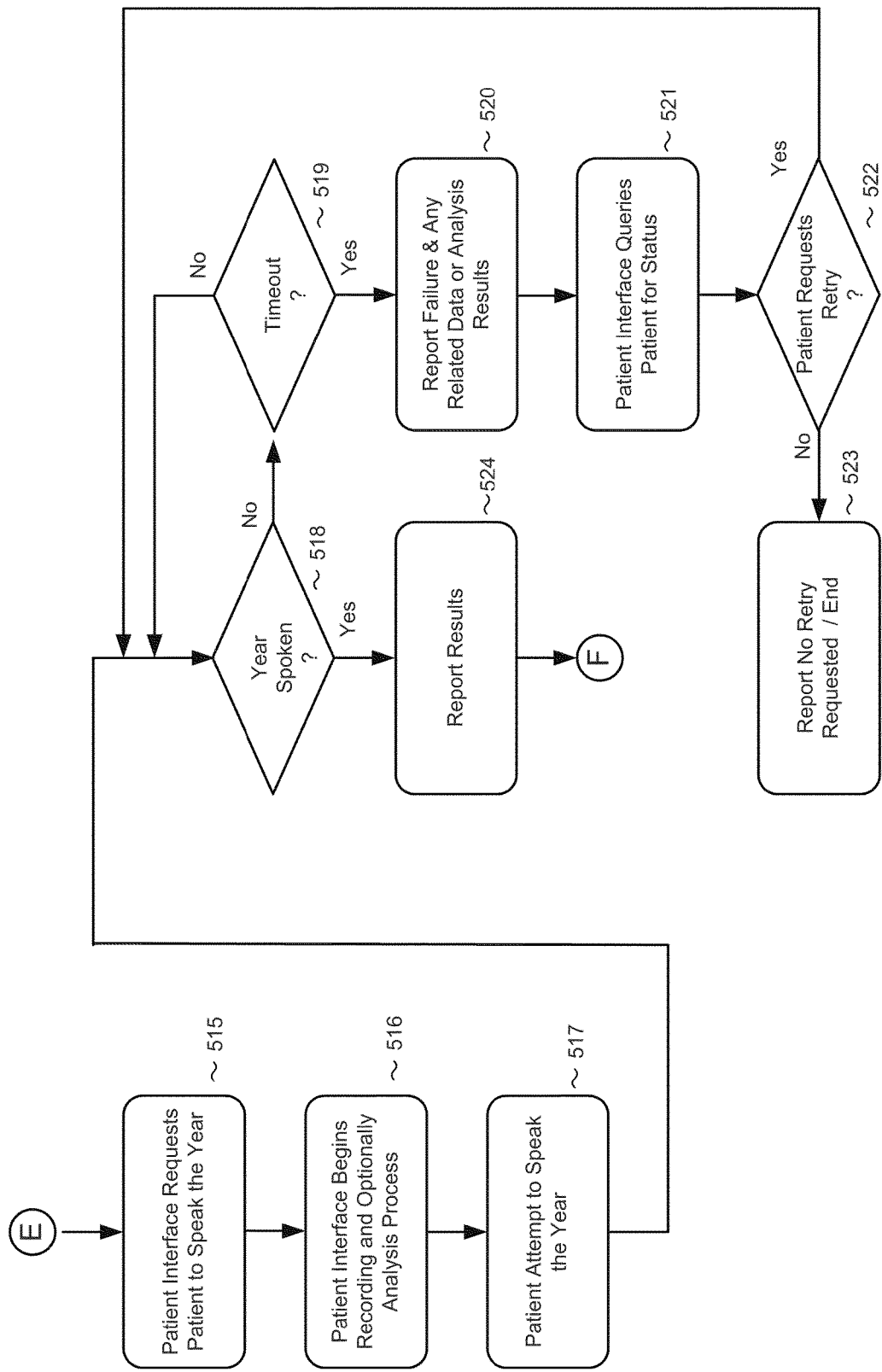
Figure 5C:
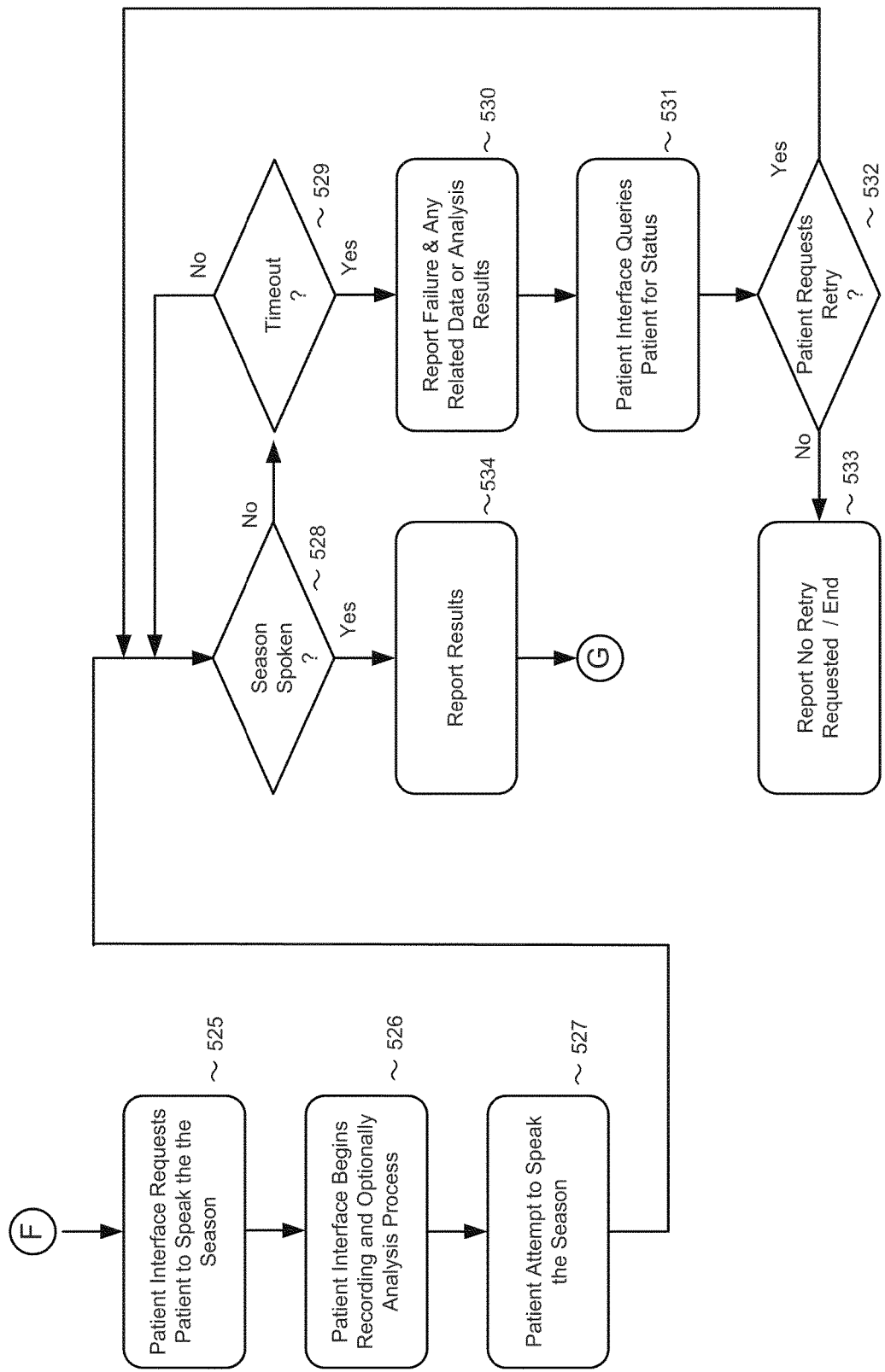
Figure 5D:
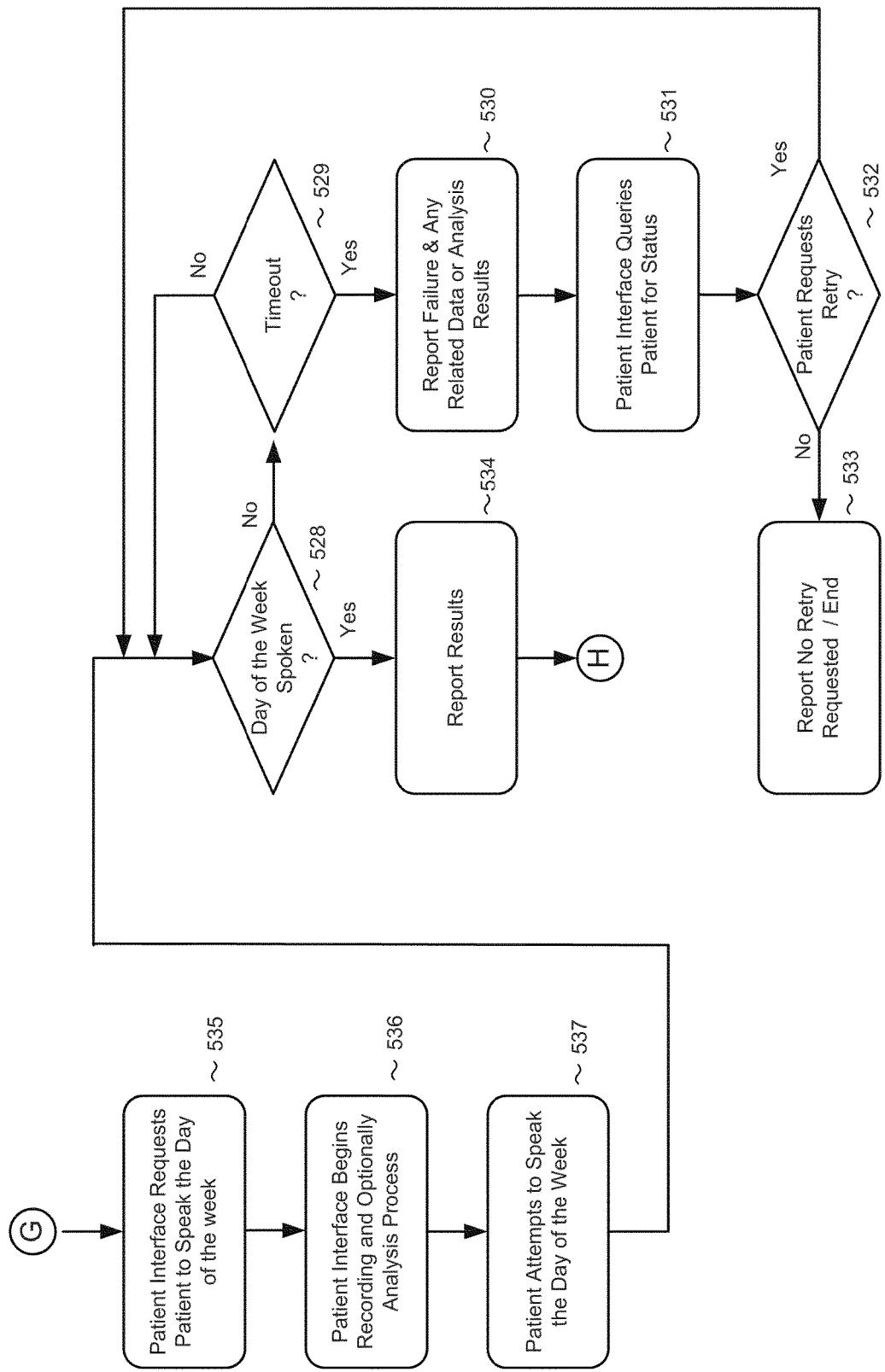
Figure 5E:
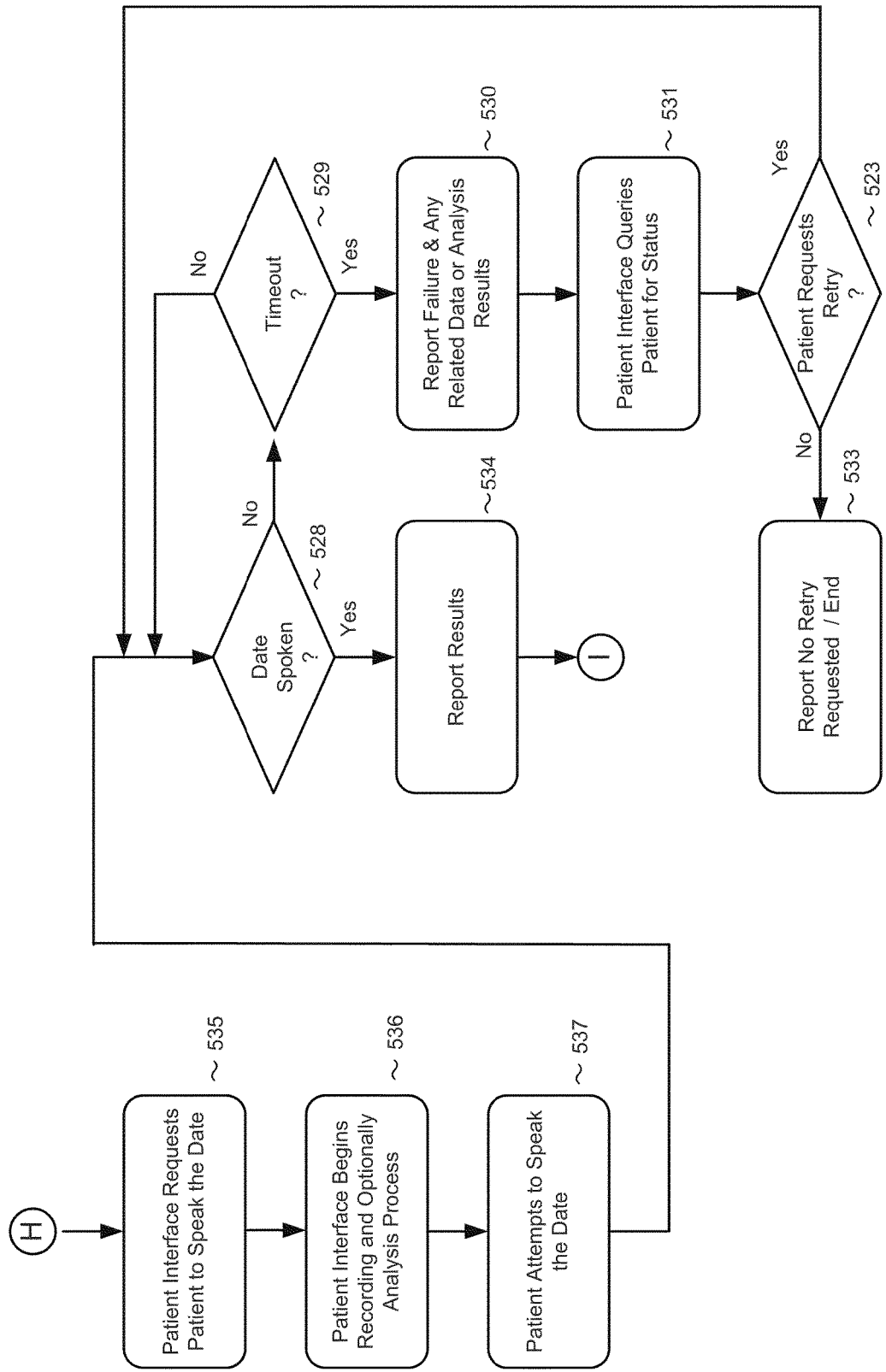

FIGS. 5a, 5b, and 5c is a flowchart of a Mini Cognition Test. A Mini Cognition Test is initiated 501 and the Patient Remote Interface speaks three words selected from a prescribed list. The list may be selected based upon a variety of factors, including patient's age and education. The patient interface begins recording and, optionally, analyzing the words which will be repeated by the patient 503. The patient interface then requests that the same three words be spoken by the patient 504. The patient then attempts to speak the same three words 505. A test is performed to see if the words are spoken 506. If yes, the results are reported or logged 511. If no, then a check is performed see if the test has timed out 507 (time limit reached). If no timeout has occurred, the words spoken test is continued 506. If there is a timeout 507, then the failure is reported or logged along with any optional analysis results 508. The patient interface may then query the patient for a status 509. If the patent requests a retry, then the system again checks for words spoken 506. If the patient does not request a retry, then no retry is logged or reported 515.

After the results have been logged or reported 511, a touchscreen, writing pad or other user interface is enabled as appropriate to acquire drawn clock data 512. The patient interface then requests that the patient draw a clock 513. The patient then attempts to draw a clock 514. A test is performed to see if the clock has been drawn 516. If "no", then a test is performed to see if a timeout has occurred 517. If a timeout has occurred, then the failure is reported along with any related data analysis and results 518. The patient interface may then query the patient for status 519. If the patent requests a retry 520, then the system again checks for the drawn clock 516. If the patient does not request a retry, then no retry is logged or reported 521. If a clock has been drawn 516, the results are logged or reported 522.

The patient interface begins recording and, optionally, analyzing the words which will be repeated by the patient 523. The patient interface then requests a repeat of the same three words that were requested earlier 524. The patient then attempts to speak the same three words 525. A test is performed to see if the words are spoken 526. If yes, the results are reported or logged 532. If no, then a check is performed see if the test has timed out 527 (time limit reached). If no timeout has occurred, the words spoken test is continued 525. If there is a timeout 527, then the failure is reported or logged along with any optional analysis results 528. The patient interface may then query the patient for a status 529. If the patent requests a retry, then the system again checks for words spoken 530. If the patient does not request a retry, then no retry is logged or reported 531.

FIGS. 6a, 6b, 6c, 6d, and 6e represent one version of the standard Unified Parkinson's disease Rating Scale which was designed to be administered in person, face to face, by a trained physician, clinician, or health care provider.

The Unified Parkinson's Disease Rating Scale is a rating scale used to follow the longitudinal course of Parkinson's disease. It is made up of the following sections: Mentation, behavior, and mood, Activities of daily living, Motor, and Complications of therapy.

These sections are to be evaluated by interview and clinical observation. Some sections require multiple grades assigned to each extremity. Clinicians and researchers alike currently use the UPDRS and the motor section in particular to follow the progression of Parkinson's disease in a patient. Following the UPDRS scores over time provides insight into the patient's disease progression. For instance, Michael J. Fox's symptoms started with a slight tremor, so his motor score would have been less than 10. For most patients, the "mentation, behavior and mood" scores increase later in the disease, but there is a subset for who those symptoms develop early on.

Diagnosis of Parkinson's disease thus presently relies on a neurological examination conducted by and review of a patient's medical history by interviewing and observing a patient in person using the Unified Parkinson's Disease Rating Scale and the patient's medical history.

Parkinson's disease may be difficult to diagnose accurately, especially in the early stages. Early signs and symptoms may be dismissed by the physician or clinician administering the tests as part of the normal aging process since nearly all of the tests presently used are subjective. The present disclosure provides a means for garnering quantitative scientific data which may be utilized to diagnose the presence of disease or disorder and differentially diagnose and track the progression of Parkinson's disease from other diseases or disorders. In addition, for many diseases or disorders, a patient may not exhibit symptoms consistently. For example, in the case of Parkinson's disease, there may be only signs with or without symmetry; there may be no bradykinesia; or there may be atypical signs, such as postural, rather than rest, tremor, mild rigidity, a lack of progression of symptoms over time, and a lack of response to normal treatments such as Levodopa. The ability to acquire data more frequently at the patient's convenience, or at specific times, or a prescribed periodic basis, or when on or off medications, or at specific times of the day or night, or when the patient is exhibiting specific symptoms will greatly aid in Parkinson's research and the diagnosis of specific patients.

FIGS. 7a and 7b are a standard scoring sheet for the Unified Parkinson's Disease Rating Scale. As shown, the results are segregated by on and off medications and the results are also summarized by best and worst for the modified Hoehn and Yahr Staging, ranging from Stage 0 (which is no signs of the disease) to Stage 5 (which is wheelchair bound or bedridden unless aging). Summary results are also provided for the Activities of Daily Living ranging from 100% completely independent (able to do chores without slowness, difficulty or impairment, essentially normal, unaware of any difficulty) to 0% (vegetative functions, such as swallowing, bladder and bowel functions, are not functioning, bedridden).

FIGS. 8a-g present a detailed test methodology which represents a modified version of the Unified Parkinson's Disease Rating Scale in accordance with one implementation of the present disclosure. As shown, the Remote Patient Interface implements various tests as prescribed by the physician or caregiver. As shown, there are three levels of use, Basic, Complex, and Comprehensive. FIGS. 8a-g are not intended to show all possibilities or indeed to implement all tests, but rather to show one representative implementation of a strata of Remote Patient Interface Testing.

It should be noted that in FIGS. 8a-g that the basic test suite includes only those tests checked under basic. The complex test suite includes both the basic test suite and those test checked under complex. Likewise, the comprehensive test suite includes the complex test suite plus those test checked under comprehensive, thus the basic, complex, and comprehensive checked tests are included under the comprehensive test suite.

In one embodiment of the present disclosure, clinical validation of a system for baseline staging, data gathering, monitoring and treatment of Parkinson's disease, an initial selection of UPDRS or another fully standardized and widely practiced test is utilized to eliminate the variability associated with a new or not widely understood Assessment Protocol while focusing clinical test efforts on technology validation and simultaneously. As shown in FIGS. 8a-g of the present disclosure, the present implementation of the UPDRS is constructed as a three level test suite which are designated as basic, complex, and comprehensive. These categories primarily reflect the organization of the questions comprising the UPDRS in terms of two factors: (1) the degree to which major data collection modalities would be needed to implement in remote testing and (2) relevance across a wide range of stages of Parkinson's disease so as to maximize the information conveyed.

The basic test module will provide the clinician and researcher a baseline measurement from which to assess changes in Parkinson's disease status, and to assist in making decisions regarding medications or treatment approaches. It consists of a number of relatively simple tests that can be performed as many times as necessary either daily or multi-times per day. The test gathers the data in both go live and subjective form as it relates to the UPDRS #'s 1, 3, 4, 5, 7, 10, 12, 13, 14, 15, 16, 18, 20, 21, 22, 25, 32, 34, 40 and 41, (representing a total of 20 tests).

The complex tests will allow the clinician and researcher to more closely examine a greater set of symptom parameters. The complex test module includes UPDRS tests from the basic test module along with those that correspond to the UPDRS #'s 6, 8, 17, 19, 22, 23, 26, 27,33 and 35 (for a total of 30 tests).

The comprehensive test incorporates all levels of the UPDRS including those of the basic and complex test modules along with those from the UPDRS corresponding to #'s 2, 9, 11, 28, 29, 30, 31, 35, 36, 37, 38, 42 (a total of 42 tests). The comprehensive test can be utilized for a remote baseline examination or an examination of one complete specific area of the body. For example, a representative clinical study will utilize a longitudinal prospective study of 30 patients over 6 months. (10 with early, 10 with middle, and 10 with late stage Parkinson's disease as determined by the Hoehn and Yahr staging).

In one embodiment of the present disclosure, availability of commercial off-the-shelf sensors and actuator is essential for rapid product development and deployment. However, in all cases the technology exists for implementing each of the 42 questions of the standard UPDRS (FIG. 6) remotely.

FIGS. 9a-d present one embodiment of a full clinical protocol with the Detailed Test Methodology shown in FIGS. 8a-c. The present test methodology employs measurements that involve both motor and non-motor aspects of the UPDRS. The choice of tests to implement in one embodiment of the clinical protocol is based on (1) relevance across a wide range of stages of Parkinson's disease and (2) the desire to validate major data collection modalities (inertial measurements, video capture, audio capture, computer based questionnaires and reaction time monitoring, walking pads, handwriting tablets) to demonstrate flexibility for integration of multiple technologies. The process of integrating various data collection modalities will also provide a basic structure on which to develop and integrate other testing modules or technologies in future efforts to expand and adapt this off-site data collection solution.

As shown in FIGS. 8a-c, a variety of testing methodologies and devices are utilized, including questionnaires with short term memory shapes, words, and colors; voice capture for physician analysis or optional automated analysis; use of commercial signature verification; gait analysis systems; accelerometers or kinematic motion and position sensing; video capture for later physician or automated analysis; force stimulation and force feedback systems; dynamometers; and automated blood pressure analyzers.

Figure 10:
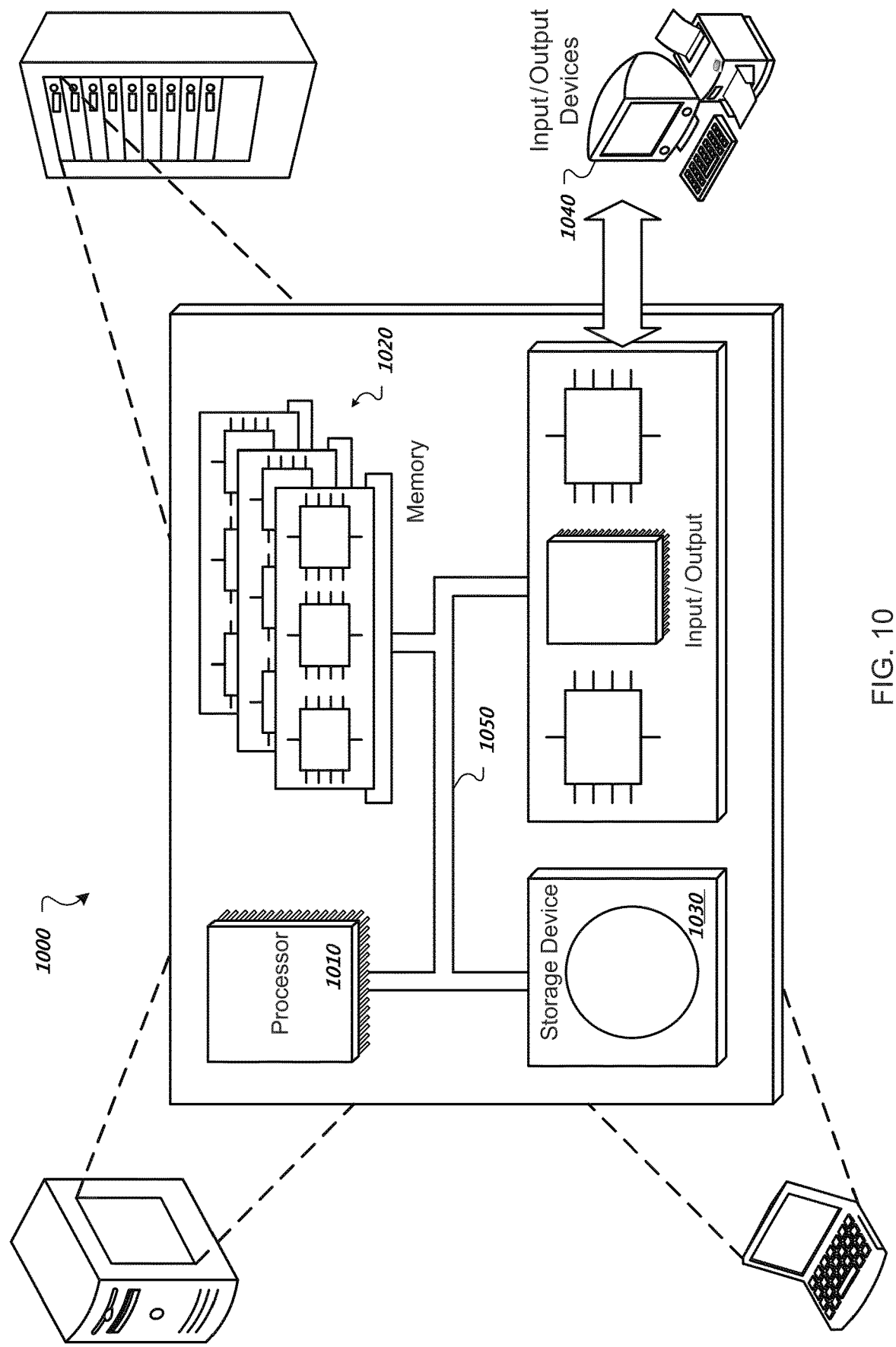
FIG. 10 is a block diagram of a computing system that can be used in connection with the data acquisition models and computer-implemented methods described in this document.

FIG. 10 is a schematic diagram of a computer system 1000. The system 1000 can be used for the operations described in association with any of the computer-implement methods described previously, according to one embodiment. The system 1000 is intended to include various forms of digital computers, such as laptops, desktops, workstations, personal digital assistants, servers, blade servers, mainframes, and other appropriate computers. The system 1000 may also include mobile devices, such as personal digital assistants, cellular telephones, smartphones, and other similar computing devices. Additionally, the system can include portable storage media, such as universal serial bus (USB) flash drives. For example, the USB flash drives may store operating systems and other applications. The USB flash drives may include input/output components, such as a wireless transmitter or USB connector that may be inserted into a USB port of another computing device.

The system 1000 includes a processor 1010, a memory 1020, a storage device 1030, and an input/output device 1040. Each of the components 1010, 1020, 1030, and 1040 are interconnected using a system bus 1050. The processor 1010 is capable of processing instructions for execution within the system 1000. The processor may be designed using any of a number of architectures. For example, the processor 1010 may be a CISC (Complex Instruction Set Computers) processor, a RISC (Reduced Instruction Set Computer) processor, or a MISC (Minimal Instruction Set Computer) processor.

In one embodiment, the processor 1010 is a single-threaded processor. In another embodiment, the processor 1010 is a multi-threaded processor. The processor 1010 is capable of processing instructions stored in the memory 1020 or on the storage device 130 to display graphical information for a user interface on the input/output device 1040.

The memory 1020 stores information within the system 1000. In one embodiment, the memory 1020 is a computer-readable medium. In one embodiment, the memory 1020 is a volatile memory unit. In another embodiment, the memory 1020 is a non-volatile memory unit.

The storage device 1030 is capable of providing mass storage for the system 1000. In one embodiment, the storage device 1030 is a computer-readable medium. In various different embodiments, the storage device 1030 may be a floppy disk device, a hard disk device, an optical disk device, or a tape device.

The input/output device 1040 provides input/output operations for the system 100. In one embodiment, the input/output device 1040 includes a keyboard and/or pointing device. In another embodiment, the input/output device 1040 includes a display unit for displaying graphical user interfaces.

The features described can be implemented in digital electronic circuitry, or in computer hardware, firmware, software, or in combinations of them. The apparatus may be implemented in a computer program product tangibly embodied in an information carrier, e.g., in a machine-readable storage device for execution by a programmable processor; and method steps can be performed by a programmable processor executing a program of instructions to perform functions of the described embodiments by operating on input data and generating output. The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features may be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features may be implemented in a computer system that includes a back-end component, such as a data server, or that includes a middleware component, such as an application server or an internet server, or that includes a front-end component, such as a client computer having a graphical user interface or an internet browser, or any combination of them. The components of the system can be connected by any form or medium of digital data communication such as a communication network. Examples of communication networks include a local area network (LAN), a wide area network (WAN), peer-to-peer networks (having ad-hoc or static members), grid computing infrastructures, and the internet.

The computer system may include clients and servers. A client and server are generally remote from each other and typically interact through a network, such as the described one. The relationship of client and server arises by virtue of computer programs running on the respective computers and having a client-server relationship to each other.

Although illustrative embodiments have been described herein with references to the accompanying drawings, it is to be understood that the present disclosure is not limited those precise embodiments, and that various other changes and modifications may be affected therein by one skilled in the art without departing from the spirit or scope of the disclosure as defined by the appended claims.

What is claimed is:

1. A system comprising:
    at least one remotely located patient device, wherein the patient device comprises a touch input screen, wherein the patient device interfaces with a data collection modality, wherein the data collection modality is at least one of a video capture device, a kinematic orientation/motion tracker, an accelerometer, a gyroscope, an attitude sensor, a global positioning system, a temperature monitor, a blood pressure monitor, a biometric security device, an electrocardiography (EKG/ECG) sensor, or an electroencephalography (EEG) sensor, and
    a data center comprising one or more servers comprising a non-transitory computer readable medium having computer program logic encoded thereon, wherein the computer program logic comprises instructions for:
    receiving patient data from the patient device, wherein the received patient data comprises motion capture data comprising motor symptoms of Parkinson's disease;
    identifying a sequence of medically related tests for monitoring Parkinson's disease based at least on the data collection modality that interfaces with the patient device, wherein the sequence of medically related tests comprises a test from a Unified Parkinson's Disease Rating Scale;
    wherein the sequence of medically related tests comprises a task to test abstract thinking skills;
    transmitting to the patient device at least one of the sequence of medically related tests for monitoring Parkinson's disease; and
    analyzing results of the at least one of the sequence of medically related tests to generate a baseline measurement that can be used to longitudinally track changes in Parkinson's disease.

2. The system of claim 1, wherein the computer program logic further comprises instructions for:
    administering the at least one of the sequence of medically related tests to a patient, wherein the results of the at least one of the sequence of medically related tests administered to the patient is received from the patient device to track a progression of Parkinson's disease; and
    optionally determining whether any additional tests should be transmitted to the patient device.

3. The system of claim 2, wherein the sequence of medically related tests comprises computer based questionnaires, and
    the results comprise monitored reaction times in response to the computer based questionnaires.

4. The system of claim 1, wherein the data center further comprises:
    a web server comprising a non-transitory computer readable medium having computer program logic encoded thereon, wherein the computer program logic comprises instructions for maintaining profiles and information of users of the system, wherein users of the system comprise at least one of a patient, a healthcare provider, a physician, a researcher, a fiduciary, or an insurer.

5. The system of claim 1, wherein the data center further comprises:
    a database server comprising a non-transitory computer readable medium having computer program logic encoded thereon, wherein the computer program logic comprises instructions for storing a database of results from an administered sequence of medically related tests.

6. The system of claim 1, wherein the data center further comprises:
    an application server comprising a non-transitory computer readable medium having computer program logic encoded thereon, wherein the computer program logic comprises instructions for transmitting the sequence of medically related tests to the patient device.

7. The system of claim 1, wherein the data center comprises a non-transitory computer readable medium having computer program logic encoded thereon, wherein the computer program logic comprises instructions for receiving the patient data in raw data format and processing the received raw data.

8. The system of claim 1, wherein the data center comprises a non-transitory computer readable medium having computer program logic encoded thereon, wherein the computer program logic comprises instructions for receiving processed patient data.

9. The system of claim 1, wherein the sequence of medically related tests comprises a cognitive test.

10. The system of claim 1, wherein the data center comprises a non-transitory computer readable medium having computer program logic encoded thereon, wherein the computer program logic comprises instructions for communicating with the patient device, a healthcare provider device, a physician device, a researcher device, or an insurer device.

11. The system of claim 1, wherein the data center comprises a non-transitory computer readable medium having computer program logic encoded thereon, wherein the computer program logic comprises instructions for receiving the patient data at a time selected based on at least one of patient preference, a prescribed periodic basis, when the patient is on or off one or more medications, at one or more specific times of day or night, or when the patient is exhibiting one or more specific symptoms.

12. The system of claim 1, wherein the patient device interfaces with the video capture device, wherein the video capture device comprises a camera, webcam, or laser imaging radar.

13. The system of claim 1, wherein the patient device interfaces with the kinematic orientation/motion tracker, wherein the kinematic orientation/motion tracker comprises one or more gyroscopes, one or more accelerometers, a magnetometer, an optical motion/position sensing system, or a microwave motion/position sensing system.

14. The system of claim 1, wherein the patient device interfaces with the kinematic orientation/motion tracker, wherein the kinematic orientation/motion tracker comprises a 3-axis gyro/accelerometer.

15. The system of claim 1, wherein the patient device interfaces with the temperature monitor, wherein the temperature monitor comprises a contact temperature sensor or an infrared remote sensor.

16. The system of claim 1, wherein the patient device interfaces with the blood pressure monitor, wherein the blood pressure monitor comprises a cuff wrap or pulse wave velocity blood pressure monitor.

17. The system of claim 1, wherein the patient device interfaces with the biometric security device, wherein the biometric security device comprises a retinal scanner or voice recognition.

18. The system of claim 1, wherein the tests from the Unified Parkinson's Disease Rating Scale consist of a subset of tests from the Unified Parkinson's Disease Rating Scale.

19. The system of claim 18, wherein the subset of the tests from the Unified Parkinson's Disease Rating Scale consists of 20 tests.

20. The system of claim 18, wherein the subset of the tests from the Unified Parkinson's Disease Rating Scale consists of 30 tests.

21. The system of claim 18, wherein the subset of the tests from the Unified Parkinson's Disease Rating Scale comprises a test to measure mentation, behavior, or mood.

22. The system of claim 18, wherein the subset of the tests from the Unified Parkinson's Disease Rating Scale comprises a test to measure activities of daily living.

23. The system of claim 18, wherein the subset of the tests from the Unified Parkinson's Disease Rating Scale comprises a test to measure motor symptoms.

24. The system of claim 18, wherein the subset of the tests from the Unified Parkinson's Disease Rating Scale comprises a test to measure complications of therapy.

25. The system of claim 1, wherein the identifying is further based on the received patient data.

26. The system of claim 1, wherein the patient device interfaces with the video capture device, wherein the video capture device comprises a camera, webcam, or laser imaging radar.

27. The system of claim 1, wherein the patient device interfaces with the kinematic orientation/motion tracker, wherein the kinematic orientation/motion tracker comprises one or more gyroscopes, one or more accelerometers, a magnetometer, an optical motion/position sensing system, or a microwave motion/position sensing system.

28. The system of claim 1, wherein the patient device interfaces with the kinematic orientation/motion tracker, wherein the kinematic orientation/motion tracker comprises a 3-axis gyro/accelerometer.

29. The system of claim 1, wherein the patient device interlaces with the temperature monitor, wherein the temperature monitor comprises a contact temperature sensor or an infrared remote sensor.

30. The system of claim 1, wherein the patient device interfaces with the blood pressure monitor, wherein the blood pressure monitor comprises a cuff wrap or pulse wave velocity blood pressure monitor.

31. The system of claim 1, wherein the patient device interfaces with the biometric security device, wherein the biometric security device comprises a retinal scanner or voice recognition.

32. A method comprising:
  receiving, at a data center comprising one or more servers, patient data from at least one remotely located patient device, wherein the patient device comprises a touch input screen, wherein the patient device interfaces with a data collection modality, wherein the data collection modality is at least one of a video capture device, a kinematic orientation/motion tracker, an accelerometer, a gyroscope, an attitude sensor, a global positioning system, a temperature monitor, a blood pressure monitor, a biometric security device, an electrocardiography (EKG/ECG) sensor, or an electroencephalography (EEG) sensor, wherein the received patient data comprises motion capture data comprising motor symptoms of Parkinson's disease;
  identifying, at the data center, a sequence of medically related tests for monitoring Parkinson's disease based at least on the data collection modality that interfaces with the patient device, wherein the sequence of medically related tests comprises a test from a Unified Parkinson's Disease Rating Scale;
  wherein the sequence of medically related tests comprises a task to test abstract thinking skills;
  transmitting, from the data center, at least one of the sequence of medically related tests for monitoring Parkinson's disease to the patient device; and
  analyzing, at the data center, results of the at least one of the sequence of medically related tests to generate a baseline measurement that can be used to longitudinally track changes in Parkinson's disease.

33. The method of claim 32, further comprising:
  analyzing, at the data center, results of each of the sequence of medically related tests, wherein each of the sequence of medically related tests is administered to a patient, wherein the results of each of the sequence of medically related tests administered to the patient are received from the patient device to track a progression of Parkinson's disease; and
  optionally determining, at the data center, whether any additional tests should be transmitted to the patient device.

34. The method of claim 33, wherein the analyzed results are used to diagnose the patient for symptoms of Parkinson's disease.

35. The method of claim 33, wherein the sequence of medically related tests comprises computer based questionnaires; and analyzing the results comprises monitoring reaction times in response to the computer based questionnaires.

36. The method of claim 32, wherein the data center further comprises:
a web server comprising a non-transitory computer readable medium having computer program logic encoded thereon, wherein the computer program logic comprises instructions for maintaining profiles and information of users of the system, wherein users of the system comprise at least one of a patient, a healthcare provider, a physician, a researcher, a fiduciary, or an insurer.

37. The method of claim 32, wherein the data center further comprises: a database server comprising a non-transitory computer readable medium having computer program logic encoded thereon, wherein the computer program logic comprises instructions for storing a database of results from an administered sequence of medically related tests.

38. The method of claim 32, wherein the data center further comprises: an application server comprising a non-transitory computer readable medium having computer program logic encoded thereon, wherein the computer program logic comprises instructions for transmitting the sequence of medically related tests to the patient device.

39. The method of claim 32, wherein receiving the patient data comprises: receiving the patient data in raw data format, and analyzing the results comprises processing the received raw data.

40. The method of claim 32, wherein receiving the patient data comprises receiving processed patient data.

41. The method of claim 32, wherein the sequence of medically related tests comprises a cognitive test.

42. The method of claim 32, further comprising receiving data from the patient device, a healthcare provider device, a physician device, a researcher device, or an insurer device.

43. The method of claim 32, further comprising:
receiving the patient data at a time selected based on at least one of patient preference, a prescribed periodic basis, when the patient is on or off one or more medications, at one or more specific times of day or night, or when the patient is exhibiting one or more specific symptoms.

44. The method of claim 32, wherein the patient device interfaces with the video capture device, wherein the video capture device comprises a camera, webcam, or laser imaging radar.

45. The method of claim 32, wherein the patient device interfaces with the kinematic orientation/motion tracker, wherein the kinematic orientation/motion tracker comprises one or more gyroscopes, one or more accelerometers, a magnetometer, an optical motion/position sensing system, or a microwave motion/position sensing system.

46. The method of claim 32, wherein the patient device interfaces with the kinematic orientation/motion tracker, wherein the kinematic orientation/motion tracker comprises a 3-axis gyro/accelerometer.

47. The method of claim 32, wherein the patient device interfaces with the temperature monitor, wherein the temperature monitor comprises a contact temperature sensor or an infrared remote sensor.

48. The method of claim 32, wherein the patient device interfaces with the blood pressure monitor, wherein the blood pressure monitor comprises a cuff wrap or pulse wave velocity blood pressure monitor.

49. The method of claim 32, wherein the patient device interfaces with the biometric security device, wherein the biometric security device comprises a retinal scanner or voice recognition.

50. The method of claim 32, wherein the tests from the Unified Parkinson's Disease Rating Scale consist of a subset of tests from the Unified Parkinson's Disease Rating Scale.

51. The method of claim 50, wherein the subset of the tests from the Unified Parkinson's Disease Rating Scale consists of 20 tests.

52. The method of claim 50, wherein the subset of the tests from the Unified Parkinson's Disease Rating Scale consists of 30 tests.

53. The method of claim 50, wherein the subset of the tests from the Unified Parkinson's Disease Rating Scale comprises a test to measure mentation, behavior, or mood.

54. The method of claim 50, wherein the subset of the tests from the Unified Parkinson's Disease Rating Scale comprises a test to measure activities of daily living.

55. The method of claim 50, wherein the subset of the tests from the Unified Parkinson's Disease Rating Scale comprises a test to measure motor symptoms.

56. The method of claim 50, wherein the subset of the tests from the Unified Parkinson's Disease Rating Scale comprises a test to measure complications of therapy.

57. The method of claim 32, wherein the identifying is further based on the received patient data.

58. The method of claim 32, wherein the patient device interfaces with the video capture device, wherein the video capture device comprises a camera, webcam, or laser imaging radar.

59. The method of claim 32, wherein the patient device interfaces with the kinematic orientation/motion tracker, wherein the kinematic orientation/motion tracker comprises one or more gyroscopes, one or more accelerometers, a magnetometer, an optical motion/position sensing system, or a microwave motion/position sensing system.

60. The method of claim 32, wherein the patient device interfaces with the kinematic orientation/motion tracker, wherein the kinematic orientation/motion tracker comprises a 3-axis gyro/accelerometer.

61. The method of claim 32, wherein the patient device interfaces with the temperature monitor, wherein the temperature monitor comprises a contact temperature sensor or an infrared remote sensor.

62. The method of claim 32, wherein the patient device interfaces with the blood pressure monitor, wherein the blood pressure monitor comprises a cuff wrap or pulse wave velocity blood pressure monitor.

63. The method of claim 32, wherein the patient device interfaces with the biometric security device, wherein the biometric security device comprises a retinal scanner or voice recognition.

64. A system comprising:
at least one remotely located patient device, wherein the patient device comprises a touch input screen,
wherein the patient device interfaces with a data collection modality, wherein the data collection modality is at least one of a video capture device, a kinematic orientation/motion tracker, an accelerometer, a gyroscope, an attitude sensor, a global positioning system, a temperature monitor, a blood pressure monitor, a biometric security device, an electrocardiography (EKG/ECG) sensor, or an electroencephalography (EEG) sensor; and
a data center comprising one or more servers comprising a non-transitory computer readable medium having computer program logic encoded thereon, wherein the
computer program logic comprises instructions for:
receiving patient data from the patient device, wherein the
received patient data comprises motion capture data
comprising motor symptoms of Parkinson's disease;
identifying a sequence of medically related tests or therapies for treating Parkinson's disease based at least on
the data collection modality that interfaces with the
patient wherein the sequence of medically related tests
comprises a test from a Unified Parkinson's Disease
Rating Scale;
wherein the sequence of medically related tests comprises
a task to test abstract thinking skills;
transmitting at least one of the sequence of medically
related tests or therapies for treating Parkinson's disease to the patient device; and
analyzing results of the at least one of the sequence of
medically related tests or therapies to generate a baseline measurement that can be used to longitudinally
track changes in Parkinson's disease.

65. The system of claim 64, wherein the computer program logic further comprises instructions for:
administering the at least one of the sequence of medically related tests or therapies to a patient, wherein the
results of the at least one of the sequence of medically
related tests or therapies administered to the patient are
received from the patient device, to track a progression
of Parkinson's disease; and
optionally determining whether any additional tests or
therapies should be transmitted to the patient device.

66. The system of claim 65, wherein the sequence of
medically related tests or therapies comprises computer
based questionnaires, and the results comprise monitored
reaction times in response to the computer based questionnaires.

67. The system of claim 64, wherein the data center
further comprises:
a web server comprising a non-transitory computer readable medium having computer program logic encoded
thereon, wherein the computer program logic comprises instructions for maintaining profiles and information of users of the system, wherein the users of the
system comprise at least one of a patient, a healthcare
provider, a physician, a researcher, a fiduciary, or an
insurer.

68. The system of claim 64, wherein the data center
further comprises:
a database server comprising a non-transitory computer
readable medium having computer program logic
encoded thereon, wherein the computer program logic
comprises instructions for storing a database of results
from an administered sequence of medically related
tests or therapies.

69. The system of claim 64, wherein the data center
further comprises:
an application server comprising a non-transitory computer readable medium having computer program logic
encoded thereon, wherein the computer program logic
comprises instructions for transmitting the sequence of
medically related tests or therapies to the patient
device.

70. The system of claim 64, wherein the data center
comprises a non-transitory computer readable medium having computer program logic encoded thereon, wherein the
computer program logic comprises instructions for receiving
the patient data in raw data format and processing the
received raw data.

71. The system of claim 64, wherein the data center
comprises a non-transitory computer readable medium having computer program logic encoded thereon, wherein the
computer program logic comprises instructions for receiving
processed patient data.

72. The system of claim 64, wherein the sequence of
medically related tests or therapies comprises a cognitive
test.

73. The system of claim 64, wherein the data center
comprises a non-transitory computer readable medium having computer program logic encoded thereon, wherein the
computer program logic comprises instructions for communicating with the patient device, a healthcare provider
device, a physician device, a researcher device, or an insurer
device.

74. The system of claim 64, wherein the data center
comprises a non-transitory computer readable medium having computer program logic encoded thereon, wherein the
computer program logic comprises instructions for receiving
the patient data at a time selected based on at least one of
patient preference, a prescribed periodic basis, when the
patient is on or off one or more medications, at one or more
specific times of day or night, or when the patient is
exhibiting one or more specific symptoms.

75. The system of claim 64, wherein the identifying is
further based on the received patient data.

76. A method comprising:
receiving, at a data center comprising one or more servers,
patient data from at least one remotely located patient
device, wherein the patient device comprises a touch
input screen, wherein the patient device interfaces with
a data collection modality, wherein the data collection
modality is at least one of a video capture device, a
kinematic orientation/motion tracker, an accelerometer,
a gyroscope, an attitude sensor, a global positioning
system, a temperature monitor, a blood pressure monitor, a biometric security device, an electrocardiography
(EKG/ECG) sensor, or an electroencephalography
(EEG) sensor, wherein the received patient data comprises motion capture data comprising motor symptoms
of Parkinson's disease;
identifying, at the data center, a sequence of medically
related tests or therapies for treating Parkinson's disease based at least on the data collection modality that
interfaces with the patient device, wherein the sequence
of medically related tests comprises a test from a
Unified Parkinson's Disease Rating Scale;
wherein the sequence of medically related tests comprises
a task to test abstract thinking skills;
transmitting, from the data center, at least one of the
sequence of medically related tests or therapies for
treating Parkinson's disease to the patient device; and
analyzing, at the data center, results of the at least one of
the sequence of medically related tests or therapies to
generate a baseline measurement that can be used to
longitudinally track changes in Parkinson's disease.

77. The method of claim 76, further comprising:
administering the at least one of the sequence of medically related tests or therapies to a patient, wherein the
results of each of the sequence of medically related
tests or therapies administered to the patient are
received from the patient device to track a progression
of Parkinson's disease; and
optionally determining, at the data center, whether any
additional tests or therapies should be transmitted to the
patient device.

78. The method of claim 77, wherein the analyzed results are used to diagnose the patient for symptoms of Parkinson's disease.

79. The method of claim 77, wherein the sequence of medically related tests or therapies comprises computer based questionnaires, and analyzing the results comprises monitoring reaction times in response to the computer based questionnaires.

80. The method of claim 76, wherein the data center comprises:
a web server comprising a non-transitory computer readable medium having computer program logic encoded thereon, wherein the computer program logic comprises instructions for maintaining profiles and information of users of the system, wherein users of the system comprise at least one of a patient, a healthcare provider, a physician, a researcher, a fiduciary, or an insurer.

81. The method of claim 76, wherein the data center further comprises: a database server comprising a non-transitory computer readable medium having computer program logic encoded thereon, wherein the computer program logic comprises instructions for storing a database of results from an administered sequence of medically related tests or therapies.

82. The method of claim 76, wherein the data center further comprises: an application server comprising a non-transitory computer readable medium having computer program logic encoded thereon, wherein the computer program logic comprises instructions for transmitting the sequence of medically related tests or therapies to the patient device.

83. The method of claim 76, wherein receiving the patient data comprises receiving the patient data in raw data format, and analyzing the results comprises processing the received raw data.

84. The method of claim 76, wherein receiving the patient data comprises receiving processed patient data.

85. The method of claim 76, wherein the sequence of medically related test or therapies comprises a cognitive test.

86. The method of claim 76, further comprising receiving data from the patient device, a healthcare provider device, a physician device, a researcher device or an insurer device.

87. The method of claim 76, further comprising:
receiving the patient data at a time selected based on at least one of patient preference, a prescribed periodic basis, when the patient is on or off one or more medications, at one or more specific times of day or night, or when the patient is exhibiting one or more specific symptoms.

88. The method of claim 76, wherein the identifying is further based on the received patient data.

89. A method comprising:
receiving, at a data center comprising one or more servers, patient data from at least one remotely located patient device, wherein the patient device comprises a touch input screen, wherein the patient device comprises voice capture capability and interfaces with a data collection modality, wherein the data collection modality comprises an accelerometer, wherein the received patient data comprises voice capture data and motion capture data, wherein the voice capture data comprises speech symptoms of Parkinson's disease and the motion capture data comprises motor symptoms of Parkinson's disease;
identifying, at the data center, a sequence of medically related tests for monitoring Parkinson's disease based at least on the data collection modality that interfaces with the patient device, wherein the sequence of medically related tests comprises a test from a Unified Parkinson's Disease Rating Scale;
wherein the sequence of medically related tests comprises a task to test abstract thinking skills;
transmitting, from the data center, at least one of the sequence of medically related tests for monitoring Parkinson's disease to the patient device; and
analyzing, at the data center, results of the at least one of the sequence of medically related tests to generate a baseline measurement that can be used to longitudinally track changes in Parkinson's disease.

90. The method of claim 89, wherein the identifying is further based on the received patient data.

* * * * *